US012279600B2

(12) United States Patent
McGrew et al.

(10) Patent No.: US 12,279,600 B2
(45) Date of Patent: Apr. 22, 2025

(54) GENETICALLY MODIFIED STERILE AVIANS AND METHOD FOR THE RECONSTITUTION THEREOF

(71) Applicant: The University Court of the University of Edinburgh, Edinburgh Lothian (GB)

(72) Inventors: Mike McGrew, Edinburgh Lothian (GB); Mark Woodcock, Edinburgh Lothian (GB)

(73) Assignee: The University Court of the University of Edinburgh, Edinburgh (GB)

( * ) Notice: Subject to any disclaimer, the term of this patent is extended or adjusted under 35 U.S.C. 154(b) by 993 days.

(21) Appl. No.: 17/282,846

(22) PCT Filed: Oct. 11, 2019

(86) PCT No.: PCT/GB2019/052895

§ 371 (c)(1),
(2) Date: Apr. 5, 2021

(87) PCT Pub. No.: WO2020/074915

PCT Pub. Date: Apr. 16, 2020

(65) Prior Publication Data

US 2021/0345592 A1 Nov. 11, 2021

(30) Foreign Application Priority Data

Oct. 12, 2018 (GB) ..................................... 1816633

(51) Int. Cl.

*A01K 67/0275* (2024.01)
*C12N 15/85* (2006.01)

(52) U.S. Cl.

CPC ...... *A01K 67/0275* (2013.01); *C12N 15/8509* (2013.01); *A01K 2217/15* (2013.01); *A01K 2217/20* (2013.01); *A01K 2217/30* (2013.01); *A01K 2227/30* (2013.01); *A01K 2267/02* (2013.01)

(58) Field of Classification Search

None
See application file for complete search history.

(56) References Cited

FOREIGN PATENT DOCUMENTS

| | | | |
|---|---|---|---|
| KR | 20120054119 | A | 5/2012 |
| RU | 2473688 | C2 | 1/2013 |
| WO | 2014193583 | A2 | 12/2014 |
| WO | 2017175745 | A1 | 10/2017 |

OTHER PUBLICATIONS

Dimitrov, Lazar, et al., "Germline Gene Editing in Chickens by Efficient CRISPR-Mediated Homologous Recombination in Primordial Germ Cells", PLoS One. vol. 11(4):e0154303 (2016).
Doran, Timothy J., et al., "Advances in genetic engineering of the avian genome: "Realising the promise"", Transgenic Res. vol. 25:307-319 (2016).
Han, Jae Yong, et al., "Primordial germ cell-mediated transgenesis and genome editing in birds", Journal of Animal Science and Biotechnology. vol. 9:19 (2018).
Han et al. "Primordial germ cell-mediated transgenesis and genome editing in birds" Journal of Animal Science and Biotechnology. 9(1):1-11 (2018).
Idoko-Akoh et al. "High fidelity CRISPR/Cas9 increases precise monoallelic and biallelic editing events in primordial germ cells" Scientific Reports. 8(1):15126 (2018).
International Search Report and Written Opinion corresponding to PCT/GB2019/052895 mailed Dec. 12, 2019 (19 pages).
Nakamura. "Poultry genetic resource conservation using primordial germ cells" Journal of Reproduction and Development. 62(5):431-437 (2016).
Smith et al. "Cell-specific ablation in the testis: what have we learned?" Andrology. 3(6):1035-1049 (2015).
Straathof et al. "An inducible caspase 9 safety switch for T-cell therapy" Blood. 105(11):4247-4254 (2005).
Taylor et al. "Efficient TALEN-mediated gene targeting of chicken primordial germ cells" Development. 144 (5):928-934 (2017).
Woodcock et al. "Gene editing in birds takes flight" Mammalian Genome. 28(7):315-323 (2017).
Zhou et al. "Generation of all-male-like sterile zebrafish by eliminating primordial germ cells at early development" Scientific Reports. 8(1):1834-1845 (2018).
Sang, Helen, "Prospects for transgenesis in the chick", Mechanisms of Development 121:1179-1186 (May 20, 2004).

*Primary Examiner* — Allison M Fox
*Assistant Examiner* — Qinhua Gu
(74) *Attorney, Agent, or Firm* — Myers Bigel, P.A.

(57) ABSTRACT

Disclosed herein transgene construct comprising (i) a first nucleotide sequence, wherein the activity of the protein encoded by said first nucleotide sequence causes death of germ cells in the presence of an exogenous induction agent and (ii) a second nucleotide sequence which targets said construct to avian germ cells, methods of using the same and a transgenic avian provided by such methods.

11 Claims, 38 Drawing Sheets

Figure 1:
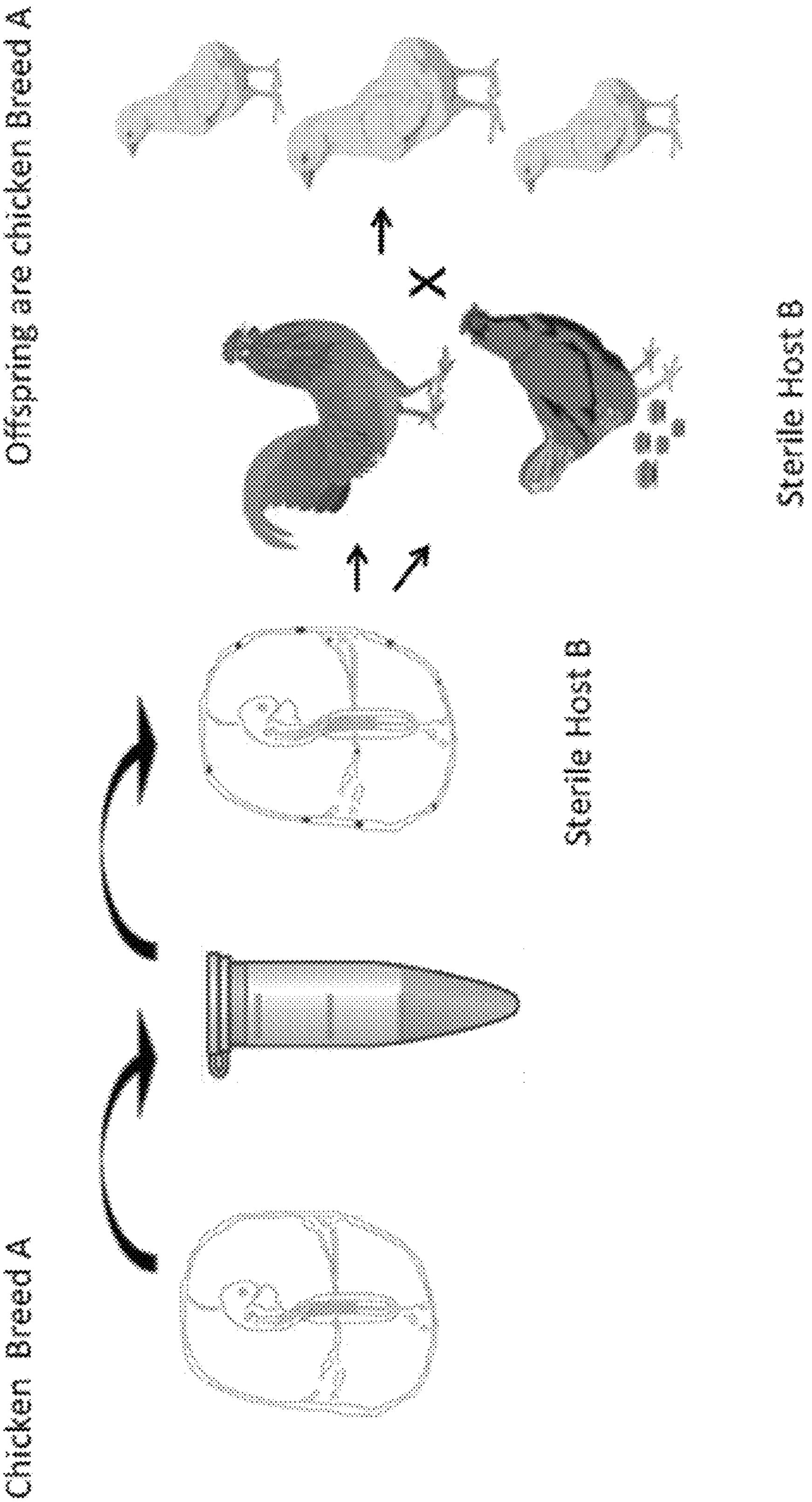

Specification includes a Sequence Listing.

Pen/strep Control
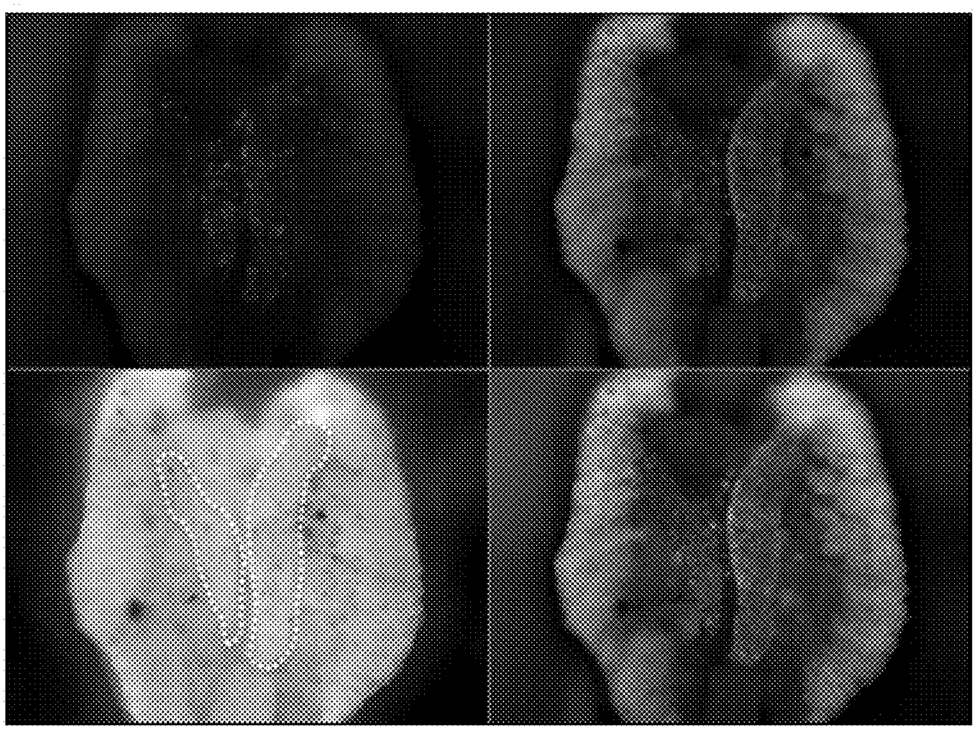
Pen/strep Control
Figure 7

DDX4

Male control embryo merge

GFP

Control

GFP

RFP aviCaspase9

GFP

RFP

Control

GFP

RFP

DDX4 merge aviCaspase

RFP

GFP merge

DDX4

Figure 13

(2a-iCaspase9-Bam H1 site mutated) – SEQ ID NO: 1

GGAtccGGAGCTACTAACTTCAGCCTGCTGAAGCAGGCTGGAGACGTGGAGGAGAACCCTGGACCT
atgctcgagggagtgcaggtggaGacTatctccccaggagacgggcgcaccttccccaagcgcggccagacctgcgtggtgcact
acaccgggatgcttgaagatggaaagaaagttgattcctcccgggacagaaacaagccctttaagtttatgctaggcaagcaggag
gtgatccgaggctgggaagaaggggttgcccagatgagtgtgggtcagagagccaaactgactatatctccagattatgcctatgg
tgccactgggcacccaggcatcatcccaccacatgccactctcgtcttcgatgtggagcttctaaaactggaatctggcggtggttcc
ggagtcgacggatttggtgatgtcggtgctcttgagagtttgaggggaaatgcagatttggcttacatcctgagcatggagccctgtg
gccactgcctcattatcaacaatgtgaacttctgccgtgagtccgggctccgcacccgcactggctccaacatcgactgtgagaagtt
gcggcgtcgcttctcctcgctgcatttcatggtggaggtgaagggcgacctgactgccaagaaaatggtgctggctttgctggagctg
gcgcGgcaggaccacggtgctctggactgctgcgtggtggtcattctctctcacggctgtcaggccagccacctgcagttcccaggg
gctgtctacggcacagatggatgccctgtgtcggtcgagaagattgtgaacatcttcaatgggaccagctgccccagcctgggaggg
aagcccaagctctttttcatccaggcctgtggtggggagcagaaagaccatgggtttgaggtggcctccacttcccctgaagacgag
tcccctggcagtaaccccgagccagatgccaccccgttccaggaaggtttgaggaccttcgaccagctggacgccatatctagtttg
cccacacccagtgacatctttgtgtcctactctactttcccaggttttgtttcctggagggaccccaagagtggctcctggtacgttgag
accctggacgacatctttgagcagtgggctcactctgaagacctgcagtccctcctgcttagggtcgctaatgctgtttcggtgaaag
ggatttataaacagatgcctggttgctttaatttcctccggaaaaaacttttctttaaaacatcagtcgactatccgtacgacgtacca
gactacgcactcgacctcgacGGAtcc

Figure 14 (2a-aviCaspase9) SEQ ID NO: 2

AGGGATCCGGAGCTACTAACTTCAGCCTGCTGAAGCAGGCTGGAGACGTGGAGGAGAACCCTGGA
CCTATGCTCGAGGGAGTGCAGGTGGAGACTATCTCCCCAGGAGACGGGCGCACCTTCCCCAAGCGC
GGCCAGACCTGCGTGGTGCACTACACCGGGATGCTTGAAGATGGAAAGAAAGTTGATTCCTCCCGG
GACAGAAACAAGCCCTTTAAGTTTATGCTTGGCAAGCAGGAGGTGATCCGAGGCTGGGAAGAAGG
GGTTGCCCAGATGAGTGTGGGTCAGAGAGCCAAACTGACTATATCTCCAGATTATGCCTATGGTGCC
ACTGGGCACCCAGGCATCATCCCACCACATGCCACTCTCGTCTTCGATGTGGAGCTTCTAAAACTGG
AATCTGGCGGTGGTTCCGGAGTCGACGGTGTCTCTGTGAATTGCAGACCAGCTAGGATGCATGCTA
GTGCATGCCAGGTGTACCAGCTGCGAGCAGACCCTTGTGGGCACTGCCTGATCTTCAACAATGTCAG
CTTCAGCAGAGACTCTGATCTGTCGACTCGAGCTGGCTCTGACATAGACTGTGAGAAGCTGGAGAA
GCGTTTCAGGTCCCTGTGCTTCCACGTCCGGACCCTGCGGAACCTCAAAGCTCAGGAAATTGATGTG
GAGCTGCGGAAGCTGGCGCGGCTCGACCACAGTGCCCTGGACTGCTGCCTCGTGGTCATCCTCTCCC
ATGGTTGCCAGACAAGCCATATTCAGTTTCCCGGAGGGATTTATGGAACAGATGGCAAAATCATTCC
AATCGAAAGGATTGTGAACTATTTCAATGGGTCCCAGTGCCCGAGTTTGAGAGGAAAACCCAAACTC
TTCTTCATCCAGGCCTGTGGAGGAGAACAAAAGGACCAAGGATTTGAGGTGGATTGTGAATCACCC
CAAGATGAAACTTGCCGACGTTCCATAGAGTCGGATGCGATTCCTTTCCAGGCTCCATCAGGGAATG
AGGACGAGCCAGACGCCGTCGCCAGTTTGCCCACTCCTGGTGACATCTTGGTGTCCTATTCAACTTTT
CCAGGTTTTGTGTCCTGGAGGGACAAGGTGAGTGGCTCGTGGTACGTGGAAACCTTGGACAGCGTA
CTGGAACATTACGCCCGTTCTGAAGACCTGCTTACCATGCTACTTCGGGTGTCAGACATCGTATCCAC
CAAGGGGAGGTACAAGCAGATCCCGGGCTGTTTCAACTTCCTTCGTAAAAAATTCTTCTTCCTGTGC
AAGGTCGACTATCCGTACGACGTACCAGACTACGCACTCGACGGATCCAA

Figure 15 (Leftarm-GFP-2a-Nitroreductase-T2a-Right arm) SEQ ID NO: 3 tttttttctttgagatgagtatcttattgcagctctgtgcataccccttgaaaatccgtaggtgatgtatttatgttgactgaaaatggag
tcattcaaaaattgatgacttcttccttttctctttttaatctcgaaacctgttctcagattcctttatcagaacaaaaagcacggctgca
tgtttttcaccgttcacacgactgtgtttagccagcgtatctaaatgcataacatgatttgccataacttgagcctgccataatcagag
cctcattttgaaagctgtcatggtctgaaacatagcatgggtaagatgattttcaccttgatgatgcatgtttaactcatttcaacgag
aggtcaaatccatccaaaaatgctaaatctatcaaccagttttcatgttcaagttctggcacaaattttcgttctgactccatacgtga
ttagatttcattttgcaaatcatgaaaactattgccaaaacatacaattttaagtcagcagttttactgcccaaatttgcacaagcaca
tgtaacgtgacagacaaaaacccactggacagagacaaaatactgggtttggccagtatggtttggctaagccacgtttttcagggc
aagaattgcctcaccttttttttatattggaatcaaattctcaagtgtaacagcctggcgccatctcagctgccattaagtagcatgtgc
tgcaacaagatgtctaccacacactctgctctgggtggtgggggcacaccagtgtggacggcaaccatgacacaagcatagagtct
tggcagaggtccattgggtgcatttatagtggttcacactggggggttatcacagaatcatggaggttggaaggtacctccgggggt
catcaaatccaaccacttgacaaagcaggttccctaaagtagattgctcaagaacagtcacagcactgctgctcacagaaaatctct
agttggtaaggttacctttttttttgttgtcgctcccagttaaaccaaggtgggaacacatccttttcatagttgtattgtagggatgttt
atagctattgctagggaaaactgaacagcgtgcaaggaagtcagcactgacacagctttcccacgtgagagagctatttcaaagca
agatcagcacatatcccaatctgtacttcctcaaacacagcccaaaaccgatagcaaggccaagcagcagcactgctccttcaagg
aaactgctgcataatctgaatttcagacggcaggaggaaacaaggcagcagactgatgacctaccaccctgagtctcagctacatg
cgatccgagccactccaactctgcttcctgcagcccttccttcacgctcatcttttgcaccttaggcactcttataattcaagtactttgt
ggctttgggatatttgaagagcttggtcagttagtcacaagtctggccacgtgctatcatattagtttgaaaagcaatggagacacca
tctgctgatgctcaaagtggttacaaccaaaacacaaaaaagcagagctgtgggaagaattcaacattttgattatgcaagaagct
agtcccagccttgaaatccaccatctgcatcatgaaagacctaagtagttaaagccacagcagacatacagcttctatttccttacct
tcttcatcattaactacaggtcttggaagatttttgctgggaaaaagcttttattgcaagaactgtaatttattaacagggaaacatga
aataaatgtgtaaattctcctgcactcccactgtcattaaaaacggctttaagaaagagtattcagtaactgcctgcattgtgttgtga
ctttctactctgtgacacacagccttctgggcaaagcacatattctgccatgcatgtgggtcgtgccttggaaaatgggaacccacat
tcactgagggcctcttgatgagctttccccttgagaacagcgaggtctcatggatatcttctcttctccaagccaaataagcccagatc
cctcagctttccttcatggagaggctccagccctctgatcatgcctgcagcccttctctggacctgctccagcagccccacacgctcct
catgctgggaccccagatctgcacatggtattgcacatggggcctcacaacggcagagctgagagggacaattccctccctcagcct
ttaattctgcacgtacttaattttgtctgtatttttttttgcaatagaatagcctgcatgctagttgctgtgtcgcacagctgaattcacta
ggttcctgtgaaacaaagggcaatcccacagccactgtagcacgtgaggagccacacaggtgctctaattcctacaggacaggcct
agggacagagcggccctaggactgccctcccgcacctcctagcttcaccttttgcccgcgatctttaagtaccctgaagcataaaca
gggaaagcgccgcccgcagcctcaccctgcttcccgcccaacgcggcaccgcccaggccgcagccgcccactaagagcactagcg
ccaccttctcaccccacccccaccacgcgttcctagcggccctgagagctgctgcgcatgcgccgcctgacgattcgccctcccattg
gctggcggtcgaagcacggcgggggcacgcggtggcggctatataaggcgtctcggaagacggcgccatgctatttggagcggag
agtgaaagttacagttcctggtgctggtagggagtgtggcgcggagcggagcgctgcggctcatcggaaccacaatggagccatag
cagagccgggcgtgggggcaagggcagtgcgtgctggggagggctccgtcgcgtggccacgtcgcgagagccgtcgggatggtgg
cgtcagggcggggggtgctgctaacgtgctcctggtcctgcaggtgggctgctggcattcgccatggtgagcaagggcgaggagct
gttcaccggggtggtgcccatcctggtcgagctggacggcgacgtaaacggccacaagttcagcgtgtccggcgagggcgagggc
gatgccacctacggcaagctgaccctgaagttcatctgcaccaccggcaagctgcccgtgccctggcccaccctcgtgaccaccctg
acctacggcgtgcagtgcttcagccgctaccccgaccacatgaagcagcacgacttcttcaagtccgccatgcccgaaggctacgtc
caggagcgcaccatcttcttcaaggacgacggcaactacaagacccgcgccgaggtgaagttcgagggcgacaccctggtgaacc
gcatcgagctgaagggcatcgacttcaaggaggacggcaacatcctggggcacaagctggagtacaactacaacagccacaacg
tctatatcatggccgacaagcagaagaacggcatcaaggtgaacttcaagatccgccacaacatcgaggacggcagcgtgcagct

Figure 15 Cont'd cgccgaccactaccagcagaacacccccatcggcgacggccccgtgctgctgcccgacaaccactacctgagcacccagtccgccc
tgagcaaagaccccaacgagaagcgcgatcacatggtcctgctggagttcgtgaccgccgccgggatcactctcggcatggacga
gctgtacaagGGAtccGGAGCTACTAACTTCAGCCTGCTGAAGCAGGCTGGAGACGTGGAGGAGAACC
CTGGACCTATGGATATCATCAGCGTGGCCCTGAAGAGACACAGCACCAAGGCCTTCGATGCCAGCA
AGAAGCTGACCCCCGAGCAGGCCGAGCAGATCAAGACCCTGCTGCAGTACAGCCCCAGCAGCCAGA
ACAGCCAGCCCTGGCACTTCATCGTGGCCAGCACCGAGGAAGGCAAGGCCAGAGTGGCCAAGAGC
GCCGCCGGCAACTACGTGTTCAGCGAGAGAAAGATGCTGGATGCCAGCCACGTGGTGGTGTTCTGC
GCCAAGACCGCtATGGATGATGTGTGGCTGAAGCTGGTGGTGGATCAGGAGGATGCCGATGGCAG
ATTCGCCACCCCCGAGGCCAAGGCCGCCAACGATAAGGGCAGAAAGTTCACCGCCGATATGCACAG
AAAGGATCTGCACGATGATGCCGAGTGGATGGCCAAGCAGGTGTACCTGAACGTGGGCAACTTCCT
GCTCGGCGTGGCCGCCCTGGGCCTGGATGCCGTGCCCATCGAGGGCTTCGATGCCGCCATCCTGGA
TGCCGAGTTCGGCCTGAAGGAGAAGGGCTACACCAGCCTGGTGGTGGTGCCCGTGGGCCACCACA
GCGTGGAGGATTTCAACGCCACCCTCCCCAAGAGCAGACTGCCCCAGAACATCACCCTGACCGAGG
TGGGAtccGGAGAGGGCAGAGGAAGTCTGCTAACATGCGGTGACGTCGAGGAGAATCCTGGACCTA
TGGAGGAGGAtTGGGAtACcGAaCTcGAGCAGGAGGCGGCAGCGGCTTCCCAGGGGCGTTCTGAGG
AGCAGGCGTGGATGGTGAGCTGTGTCCAGGGGAGGGCGGTGCGGCAGGGAGCGGGGCACTGGG
ATGGCCCGGTCTGGGAAGGGGAGGCCGAGAGGCCTTCGCAGTGCTTCCTGCAGCTCCCCGAGCAGT
GCGAAGAAGGAGGTGCCGGGCTCTGCTGTGGGAGCCGAAGGCACGGAGCTGCCTGGGGAGGGAA
TGGCTGTGTGCCTGAGGTGCCAGAGACCGGCAAGGGCTGTACAGAGAGGCAACGGTTTTGTGTAC
AAATCATTTGTATGGGAAACCACAAAATCTTGAAGCTTTATTACATGGCAGCGAAATACTTTGGTGT
GAAGTAAAGGATAAGATAGAGGAGTGTAATGAGAGACAGCTAAATAATATTTTACTACTTGTGGGA
TGAGTGAATATCAGGAGGAACTGCTGTAAATTTCAGGAGGACCTGTTGTGAATCTTCAGTAGTTGGC
GCCGCTCTTACACATCTTACAGATGCCCCTTGAGCAAAGGGGGATAAGGAGAGATGAACGGGTTAT
CCAAACAGGTGATGAGCTAAAAGTACAGTTGCCTAAAGAAGTAGTAGCATGTGCTATCAGAATGAT
AATTTTGTTAGTTTGGGGTTAGTTTCCTGTAGTGGTAGATAGCCACAACAAGAAAACCGCTTAAGTTT
TTGTAAAACAAAAAAAGCACGATCCAGAAGTAAAAAATATGGGTAGTTTTTTTTGATGTTCCTCTCTC
ACCTGGTGCTTTGGCATACTAATATGTGTCTAATTGTATTAAACAGGAGAAATTTAAACCTAGGCTTT
GCTGGAAATAAAATGTTACAATGCTACAATGTGAAAAGTAGGTGCTATTCTGAACTGTTTTGGGTGG
AGTATCTGAATCTTTGAATAATTTAAGAGGGACTGACATATTTAAAATACTTAAGGATAATCTGTAGC
CATGCTGTAAAAGAACAACAGAAATGCAGTTGGGAAGGTGATGGAAATAGTTTTATTCATGTTACTG
GTGGTCTGAAACCTTTCTAAGCTTAAACTGTAGAAAAAAATTGCTTCAAAAGATTGCACTATTACTTT
GGGCGACAAATGTTTTTAATTGGTTTTAAGTGTTTGTTAGCAAAGTGAAGTTGATGCCACCATAAGT
CTGACAGGAGGCAAGATAAACTTGTCTTCATACTGCTTGTGTATAACTTGGTTTTGATGACATTTGTG
TGTGAACATTATGCACTTCAGTGTAGCGAAGTTTAAGAAACTTTGAACAGAATAACTTGAAAGAGTG
TGCACATGGGTGCAGAAGTCACTTTATTTCAGTTGGGAGACTTAGCACCTAAATGCACTGTTAGTTC
ACATACACTTTGCTTGGCCTGAAGGTAACATTGTGATGTCGCTTTTTTTCCCTGTAGGCTAACTCTGG
CAGACCAAACAGCCCATCCCTCCGCTTCTCCAGCAGACCAAGCAGCCCCTTGTCTGG

Figure 16 (Left arm-2a-aviCaspase9-T2a-GFP-Right arm) SEQ ID NO: 4

CTTCGTGGCTTGGTGAAGAGATCTTCTGACCTCTTCATCACCCCCTAGAATTAAGGCTGTAATCATCA
TTTCAGCCATTGCTTAATCCACTATAATTTCTGCATGATTTCAGAAGGCTATCTTGCTTCCTTGAAACT
AATAATACCTAGTTTGTAGTGTTTAGGGATGTGTAAAATGTGTTTATGTCAAGATTTTAGTTAGTCTG
ATAAGAATTGTGGAAGAATTGCAGCTACTAAAAAGGCAGACTGGGTAGCACTTCCCACCTTACTCAG
ATTTAGGAGTCTCAAGACATGTAGATGGGTGAAATTTATTATTCTTTTCTCTGCTTGCTTTTCTGGAAA
GCTACCTCTATTTGGCCAGCAGTTGGCTCTGAATTCCTTTCTTTAAAGGAGACCTGACTGCTCTCCTGT
CTGCCTCTTACACAGCTGTACTGGTGTGTCACTGATAGAAACGTTTACCTTGAAAGTGACAAGTGGG
GGCGTTGATACCCATTAACAACATTAAAGGGAAAATTTCAGGAAACAAGAAAACTGAGAGGAGTTC
AGAATGAAATGTAAGCCCTGTGACAGACTCACACTGATGGTAGTAGGGTAACTGATGGAGATGCAT
CTATAACAATTCTAACTTTTATTTCAGAAGTCTGTGGACAGGAGCATACAAACAGTAGTATCTTGTCT
GTTTAACCCTGAAAACCGTCTGAGGAACACCTTTGTATCACAAGAAGACTACTTCAGGGTATGTAGT
GAAAGCAAAACTAAATCTCTAAAACCAGCTGATCTTAACTTTGTTCATATACAGGATGCCATGAAGA
CAAAGGTTTATCTGTACTTGCTTGAGATTTTACTTTTTGTATGTGCATTGAGATGAATGACTGGTTAG
CTCTCAGTTGGTTAATACTCAATGAAAATTGCAGAAATTGAGTTCAGTGGATTTAAGTGCATTGATAC
AAGGCTGCATAAGAACTGCTGAGCAGTCAGCTATTGGATATTTAGAGCTAATCATCCCTCAGGAGCA
ATCTGCTGAAAGGTAAGCAGATTGCATCTTGTAAACGAGAGAGCAGAGTTAAACGTTTGTGGTCTTT
GCTCCACTTAAGTACCCACAGTGGATGTCTATCTGTACTTTTGGTTAAAAAATAGATAATTTCTACAA
CAGACTGTAGTTAGGTCAGTACCTGGTCATCAGGTATTAATGGAAAGCTTTTTGCTGTGCATTCAATC
TTCATAGAGGTCTGCTTTCCAATTACATTCTCTTTGTTTTAAGTATAACTTTGAAACTCAAATATAAAA
GCCTGCTACTTTTTTTTGTTCTAAAAAGACAGATGTGGACTAGGCACCTGTACTGTGAAACCAGAATA
GAGAAGCTGTTGGGCAGATTTGAAGAGGATTGAGTAATATAGAGAATGTCTTGAGATATTTGTGAA
GCTTTTATTGCTTTGTTGCAATTGTTGTCTAGAAACATGGGCTTTTTCTGTTTTTTCTCCTATTCCAGGA
GAGGAGGGCGCATCACTTCAGAAAAGGAAGAGCAGTGCTCAAAAGTGTTGGATCCGGAGCTACTA
ACTTCAGCCTGCTGAAGCAGGCTGGAGACGTGGAGGAGAACCCTGGACCTATGCTCGAGGGAGTG
CAGGTGGAGACTATCTCCCCAGGAGACGGGCGCACCTTCCCCAAGCGCGGCCAGACCTGCGTGGTG
CACTACACCGGGATGCTTGAAGATGGAAAGAAAGTTGATTCCTCCCGGGACAGAAACAAGCCCTTT
AAGTTTATGCTTGGCAAGCAGGAGGTGATCCGAGGCTGGGAAGAAGGGGTTGCCCAGATGAGTGT
GGGTCAGAGAGCCAAACTGACTATATCTCCAGATTATGCCTATGGTGCCACTGGGCACCCAGGCATC
ATCCCACCACATGCCACTCTCGTCTTCGATGTGGAGCTTCTAAAACTGGAATCTGGCGGTGGTTCCG
GAGTCGACGGTGTCTCTGTGAATTGCAGACCAGCTAGGATGCATGCTAGTGCATGCCAGGTGTACC
AGCTGCGAGCAGACCCTTGTGGGCACTGCCTGATCTTCAACAATGTCAGCTTCAGCAGAGACTCTGA
TCTGTCGACTCGAGCTGGCTCTGACATAGACTGTGAGAAGCTGGAGAAGCGTTTCAGGTCCCTGTGC
TTCCACGTCCGGACCCTGCGGAACCTCAAAGCTCAGGAAATTGATGTGGAGCTGCGGAAGCTGGCG
CGGCTCGACCACAGTGCCCTGGACTGCTGCCTCGTGGTCATCCTCTCCCATGGTTGCCAGACAAGCC
ATATTCAGTTTCCCGGAGGGATTTATGGAACAGATGGCAAAATCATTCCAATCGAAAGGATTGTGAA
CTATTTCAATGGGTCCCAGTGCCCGAGTTTGAGAGGAAAACCCAAACTCTTCTTCATCCAGGCCTGT
GGAGGAGAACAAAAGGACCAAGGATTTGAGGTGGATTGTGAATCACCCCAAGATGAAACTTGCCG
ACGTTCCATAGAGTCGGATGCGATTCCTTTCCAGGCTCCATCAGGGAATGAGGACGAGCCAGACGC
CGTCGCCAGTTTGCCCACTCCTGGTGACATCTTGGTGTCCTATTCAACTTTTCCAGGTTTTGTGTCCTG
GAGGGACAAGGTGAGTGGCTCGTGGTACGTGGAAACCTTGGACAGCGTACTGGAACATTACGCCC

Figure 16 Cont'd

GTTCTGAAGACCTGCTTACCATGCTACTTCGGGTGTCAGACATCGTATCCACCAAGGGGAGGTACAA
GCAGATCCCGGGCTGTTTCAACTTCCTTCGTAAAAAATTCTTCTTCCTGTGCAAGGTCGACTATCCGT
ACGACGTACCAGACTACGCACTCGACGGAtccGGAGAGGGCAGAGGAAGTCTGCTAACATGCGGTG
ACGTCGAGGAGAATCCTGGACCTatggtgagcaagggcgaggagctgttcaccggggtggtgcccatcctggtcgagct
ggacggcgacgtaaacggccacaagttcagcgtgtccggcgagggcgagggcgatgccacctacggcaagctgaccctgaagttc
atctgcaccaccggcaagctgcccgtgccctggcccaccctcgtgaccaccctgacctacggcgtgcagtgcttcagccgctacccc
gaccacatgaagcagcacgacttcttcaagtccgccatgcccgaaggctacgtccaggagcgcaccatcttcttcaaggacgacgg
caactacaagacccgcgccgaggtgaagttcgagggcgacaccctggtgaaccgcatcgagctgaagggcatcgacttcaaggag
gacggcaacatcctggggcacaagctggagtacaactacaacagccacaacgtctatatcatggccgacaagcagaagaacggc
atcaaggtgaacttcaagatccgccacaacatcgaggacggcagcgtgcagctcgccgaccactaccagcagaacacccccatcg
gcgacggccccgtgctgctgcccgacaaccactacctgagcacccagtccgccctgagcaaagaccccaacgagaagcgcgatca
catggtcctgctggagttcgtgaccgccgccgggatcactctcggcatggacgagctgtacaagTGATGAACAAAGACTTT
GAAGTACATAAATGTATTACTTTGATGTTaaTACAGTTCAGTTTAGTAAGATGTGTAGTAAAAAGTGT
AACCTTGTTCAAAAAGTTGCTTCAAGTTGATGTTTGTGTTCTGTTTTACCTGTTCCAGAATAGCTATTT
TTGCTTGAGAAGTTTGAAGTTGTAAGAGTTGAAATATTTCCAGGTTTTATTACTAGCTTGCATGCTTT
TCCTGCTAACTAACTGAAATGCTAATCTTAAGGAATTTATATGGGGAAGGGGAAAAAAGAAAAACA
CTTTGTTTGGTACGTGTGGATTTTCTTCTGAGCTTTAAGGTACAGTTTGTTGCATGTTAAAATTTAGTT
CTTATTAAACCACAACTTTAAGTTACTAACGTCAACCAGTTACCTCTTGCAGTTCAAAAGTTGAAGCA
GTTCCTTGTCCAAGATGGAGTATTTTAAAACTGAGCTCTTAATCAGTGGAACAGAAGACGTCACGGT
GTAACTCAACTGAAGCCCTTTAAGTCCCGGTTCTCTTTAGACTACCTAATCAATGTCTTTGTTTGCTAA
CGACAGTTTATCTATGTGAATCCTAAAATTCCTATATGTAACTTAAGATGCAAGAATGTAATTAGTTA
CATTGGCTGCTCAGTGGAGTATGACTTTTTTTTTTACTGGATTAATTTTAGCAATACCTGTATCTTAAA
ATTGTGAGAAAATACTGCATTTAAAATATGCCTAACTTTGTGATGCAATATGTTAATCAAAGAATACA
TGTAAGCATATTTTAATAATAATTATGTAGATTTTAGTCATGTATTTTGAAACAATTAAAATTTTTAAT
TTTGACTTACCTTCCCAGTGTGAGTGACATCCTAATATAATACTTCTAAATCTTAAGCTGCTTTGAGAA
AGGCATGCAGCGTATTTATTGAAGGAATTGAAGATTTCTTACCCTACATAAGAATTCCAGTTAGGAC
AAGTTTATAGCAACAAACTTTCACATTTGCTGTTAGTTCTACCTGCGATTTTGAAGGAGTACAACTGA
GAACAGCACTCAGTCTTGTATGTGTGTTGGGTCCTAGTCTGATTCATTTTTCTTATTACTACCCTTATA
CCTCAGTCTCCAAGTAAAAAAGGAAATAACTCCTCCTTTGTAGACGTGTATATGTGAATGAATAGAA
TGGCATGTCCCACTTCAAATGTCTAGAAGTAGATGTTGGTGAAACATGCAATAAGAGCTGAGTTGCT
CTGTACCTGGATAGTGGGCTGTAAGATGCAGCACAGGAGTGTCCCAGGACTGTTGTTCAGGAGTAG
GAGTCAGGGGAGGGAGGCAGGGCTTGGGGGATAGCAATAATAGTTGGTGCCGTTCTCCATAAAAT
TACTCAGAAGCAATGTTCTGGCAGCATAAATCGACCTAAAGTTGTTAACTTTTTCTCTGCTCAGACCG
TTCCCTAGCACTAAAGATGCTGTGTCCTTAAGTGTGTTTCCATACTATCCATCACCATGTTTTTCCCAA
CCTATTGCTTTAATAGTATTG

Figure 17 (Left arm-2a-iCaspase9-T2a-GFP-Right arm) SEQ ID NO: 5

CTTCGTGGCTTGGTGAAGAGATCTTCTGACCTCTTCATCACCCCCTAGAATTAAGGCTGTAATCATCATTTCAG
CCATTGCTTAATCCACTATAATTTCTGCATGATTTCAGAAGGCTATCTTGCTTCCTTGAAACTAATAATACCTAG
TTTGTAGTGTTTAGGGATGTGTAAAATGTGTTTATGTCAAGATTTTAGTTAGTCTGATAAGAATTGTGGAAGA
ATTGCAGCTACTAAAAAGGCAGACTGGGTAGCACTTCCCACCTTACTCAGATTTAGGAGTCTCAAGACATGTA
GATGGGTGAAATTTATTATTCTTTTCTCTGCTTGCTTTTCTGGAAAGCTACCTCTATTTGGCCAGCAGTTGGCTC
TGAATTCCTTTCTTTAAAGGAGACCTGACTGCTCTCCTGTCTGCCTCTTACACAGCTGTACTGGTGTGTCACTGA
TAGAAACGTTTACCTTGAAAGTGACAAGTGGGGGCGTTGATACCCATTAACAACATTAAAGGGAAAATTTCAG
GAAACAAGAAAACTGAGAGGAGTTCAGAATGAAATGTAAGCCCTGTGACAGACTCACACTGATGGTAGTAGG
GTAACTGATGGAGATGCATCTATAACAATTCTAACTTTTATTTCAGAAGTCTGTGGACAGGAGCATACAAACA
GTAGTATCTTGTCTGTTTAACCCTGAAAACCGTCTGAGGAACACCTTTGTATCACAAGAAGACTACTTCAGGGT
ATGTAGTGAAAGCAAAACTAAATCTCTAAAACCAGCTGATCTTAACTTTGTTCATATACAGGATGCCATGAAG
ACAAAGGTTTATCTGTACTTGCTTGAGATTTTACTTTTTGTATGTGCATTGAGATGAATGACTGGTTAGCTCTCA
GTTGGTTAATACTCAATGAAAATTGCAGAAATTGAGTTCAGTGGATTTAAGTGCATTGATACAAGGCTGCATA
AGAACTGCTGAGCAGTCAGCTATTGGATATTTAGAGCTAATCATCCCTCAGGAGCAATCTGCTGAAAGGTAAG
CAGATTGCATCTTGTAAACGAGAGAGCAGAGTTAAACGTTTGTGGTCTTTGCTCCACTTAAGTACCCACAGTG
GATGTCTATCTGTACTTTTGGTTAAAAAATAGATAATTTCTACAACAGACTGTAGTTAGGTCAGTACCTGGTCA
TCAGGTATTAATGGAAAGCTTTTTGCTGTGCATTCAATCTTCATAGAGGTCTGCTTTCCAATTACATTCTCTTTG
TTTTAAGTATAACTTTGAAACTCAAATATAAAAGCCTGCTACTTTTTTTTGTTCTAAAAAGACAGATGTGGACTA
GGCACCTGTACTGTGAAACCAGAATAGAGAAGCTGTTGGGCAGATTTGAAGAGGATTGAGTAATATAGAGAA
TGTCTTGAGATATTTGTGAAGCTTTTATTGCTTTGTTGCAATTGTTGTCTAGAAACATGGGCTTTTTCTGTTTTTT
CTCCTATTCCAGGAGAGGAGGGCGCATCACTTCAGAAAAGGAAGAGCAGTGCTCAAAAGTGTTGGAtccGGA
GCTACTAACTTCAGCCTGCTGAAGCAGGCTGGAGACGTGGAGGAGAACCCTGGACCTatgctcgagggagtgcagg
tggaGacTatctccccaggagacgggcgcaccttccccaagcgcggccagacctgcgtggtgcactacaccgggatgcttgaagatggaaag
aaagttgattcctcccgggacagaaacaagccctttaagtttatgctaggcaagcaggaggtgatccgaggctgggaagaaggggttgcccag
atgagtgtgggtcagagagccaaactgactatatctccagattatgcctatggtgccactgggcacccaggcatcatcccaccacatgccactct
cgtcttcgatgtggagcttctaaaactggaatctggcggtggttccggagtcgacggatttggtgatgtcggtgctcttgagagtttgaggggaaa
tgcagatttggcttacatcctgagcatggagccctgtggccactgcctcattatcaacaatgtgaacttctgccgtgagtccgggctccgcacccg
cactggctccaacatcgactgtgagaagttgcggcgtcgcttctcctcgctgcatttcatggtggaggtgaagggcgacctgactgccaagaaaa
tggtgctggctttgctggagctggcgcGgcaggaccacggtgctctggactgctgcgtggtggtcattctctctcacggctgtcaggccagccacc
tgcagttcccaggggctgtctacggcacagatggatgccctgtgtcggtcgagaagattgtgaacatcttcaatgggaccagctgccccagcctg
ggagggaagcccaagctctttttcatccaggcctgtggtggggagcagaaagaccatgggtttgaggtggcctccacttcccctgaagacgagtc
ccctggcagtaaccccgagccagatgccaccccgttccaggaaggtttgaggaccttcgaccagctggacgccatatctagtttgcccacaccca
gtgacatctttgtgtcctactctactttcccaggttttgtttcctggagggaccccaagagtggctcctggtacgttgagaccctggacgacatcttt
gagcagtgggctcactctgaagacctgcagtccctcctgcttagggtcgctaatgctgtttcggtgaaagggatttataaacagatgcctggttgc
tttaatttcctccggaaaaaacttttctttaaaacatcagtcgactatccgtacgacgtaccagactacgcactcgacctcgacGGAtccGGAG
AGGGCAGAGGAAGTCTGCTAACATGCGGTGACGTCGAGGAGAATCCTGGACCTatggtgagcaagggcgaggagct
gttcaccggggtggtgcccatcctggtcgagctggacggcgacgtaaacggccacaagttcagcgtgtccggcgagggcgagggcgatgccac
ctacggcaagctgaccctgaagttcatctgcaccaccggcaagctgcccgtgccctggcccaccctcgtgaccaccctgacctacggcgtgcagt
gcttcagccgctaccccgaccacatgaagcagcacgacttcttcaagtccgccatgcccgaaggctacgtccaggagcgcaccatcttcttcaag
gacgacggcaactacaagacccgcgccgaggtgaagttcgagggcgacaccctggtgaaccgcatcgagctgaagggcatcgacttcaagga
ggacggcaacatcctggggcacaagctggagtacaactacaacagccacaacgtctatatcatggccgacaagcagaagaacggcatcaagg
tgaacttcaagatccgccacaacatcgaggacggcagcgtgcagctcgccgaccactaccagcagaacacccccatcggcgacggccccgtgc
tgctgcccgacaaccactacctgagcacccagtccgccctgagcaaagaccccaacgagaagcgcgatcacatggtcctgctggagttcgtgac
cgccgccgggatcactctcggcatggacgagctgtacaagTGATGAACAAAGACTTTGAAGTACATAAATGTATTACTTTGA

Figure 17 Cont'd

TGTTaaTACAGTTCAGTTTAGTAAGATGTGTAGTAAAAAGTGTAACCTTGTTCAAAAAGTTGCTTCAAGTTGAT
GTTTGTGTTCTGTTTTACCTGTTCCAGAATAGCTATTTTTGCTTGAGAAGTTTGAAGTTGTAAGAGTTGAAATAT
TTCCAGGTTTTATTACTAGCTTGCATGCTTTTCCTGCTAACTAACTGAAATGCTAATCTTAAGGAATTTATATGG
GGAAGGGGAAAAAAGAAAAACACTTTGTTTGGTACGTGTGGATTTTCTTCTGAGCTTTAAGGTACAGTTTGTT
GCATGTTAAAATTTAGTTCTTATTAAACCACAACTTTAAGTTACTAACGTCAACCAGTTACCTCTTGCAGTTCAA
AAGTTGAAGCAGTTCCTTGTCCAAGATGGAGTATTTTAAAACTGAGCTCTTAATCAGTGGAACAGAAGACGTC
ACGGTGTAACTCAACTGAAGCCCTTTAAGTCCCGGTTCTCTTTAGACTACCTAATCAATGTCTTTGTTTGCTAAC
GACAGTTTATCTATGTGAATCCTAAAATTCCTATATGTAACTTAAGATGCAAGAATGTAATTAGTTACATTGGC
TGCTCAGTGGAGTATGACTTTTTTTTTTACTGGATTAATTTTAGCAATACCTGTATCTTAAAATTGTGAGAAAAT
ACTGCATTTAAAATATGCCTAACTTTGTGATGCAATATGTTAATCAAAGAATACATGTAAGCATATTTTAATAAT
AATTATGTAGATTTTAGTCATGTATTTTGAAACAATTAAAATTTTTAATTTTGACTTACCTTCCCAGTGTGAGTG
ACATCCTAATATAATACTTCTAAATCTTAAGCTGCTTTGAGAAAGGCATGCAGCGTATTTATTGAAGGAATTGA
AGATTTCTTACCCTACATAAGAATTCCAGTTAGGACAAGTTTATAGCAACAAACTTTCACATTTGCTGTTAGTTC
TACCTGCGATTTTGAAGGAGTACAACTGAGAACAGCACTCAGTCTTGTATGTGTGTTGGGTCCTAGTCTGATTC
ATTTTTCTTATTACTACCCTTATACCTCAGTCTCCAAGTAAAAAAGGAAATAACTCCTCCTTTGTAGACGTGTAT
ATGTGAATGAATAGAATGGCATGTCCCACTTCAAATGTCTAGAAGTAGATGTTGGTGAAACATGCAATAAGA
GCTGAGTTGCTCTGTACCTGGATAGTGGGCTGTAAGATGCAGCACAGGAGTGTCCCAGGACTGTTGTTCAGG
AGTAGGAGTCAGGGGAGGGAGGCAGGGCTTGGGGGATAGCAATAATAGTTGGTGCCGTTCTCCATAAAATT
ACTCAGAAGCAATGTTCTGGCAGCATAAATCGACCTAAAGTTGTTAACTTTTTCTCTGCTCAGACCGTTCCCTA
GCACTAAAGATGCTGTGTCCTTAAGTGTGTTTCCATACTATCCATCACCATGTTTTTCCCAACCTATTGCTTTAAT
AGTATTG

Figure 18 (Left arm-GFP-2a-iCaspase9-T2a-Right arm) SEQ ID NO: 6 tttttttctttgagatgagtatcttattgcagctctgtgcataccccttgaaaatccgtaggtgatgtatttatgttgactgaaaatggag
tcattcaaaaattgatgacttcttccttttctctttttaatctcgaaacctgttctcagattcctttatcagaacaaaaagcacggctgca
tgtttttcaccgttcacacgactgtgtttagccagcgtatctaaatgcataacatgatttgccataacttgagcctgccataatcagag
cctcattttgaaagctgtcatggtctgaaacatagcatgggtaagatgattttcaccttgatgatgcatgtttaactcatttcaacgag
aggtcaaatccatccaaaaatgctaaatctatcaaccagttttcatgttcaagttctggcacaaattttcgttctgactccatacgtga
ttagatttcattttgcaaatcatgaaaactattgccaaaacatacaattttaagtcagcagttttactgcccaaatttgcacaagcaca
tgtaacgtgacagacaaaaacccactggacagagacaaaatactgggtttggccagtatggtttggctaagccacgtttttcagggc
aagaattgcctcaccttttttttatattggaatcaaattctcaagtgtaacagcctggcgccatctcagctgccattaagtagcatgtgc
tgcaacaagatgtctaccacacactctgctctgggtggtgggggcacaccagtgtggacggcaaccatgacacaagcatagagtct
tggcagaggtccattgggtgcatttatagtggttcacactggggggttatcacagaatcatggaggttggaaggtacctccgggggt
catcaaatccaaccacttgacaaagcaggttccctaaagtagattgctcaagaacagtcacagcactgctgctcacagaaaatctct
agttggtaaggttaccttttttttttgttgtcgctcccagttaaaccaaggtgggaacacatccttttcatagttgtattgtagggatgttt
atagctattgctagggaaaactgaacagcgtgcaaggaagtcagcactgacacagctttcccacgtgagagagctatttcaaagca
agatcagcacatatcccaatctgtacttcctcaaacacagcccaaaaccgatagcaaggccaagcagcagcactgctccttcaagg
aaactgctgcataatctgaatttcagacggcaggaggaaacaaggcagcagactgatgacctaccaccctgagtctcagctacatg
cgatccgagccactccaactctgcttcctgcagcccttccttcacgctcatcttttgcaccttaggcactcttataattcaagtactttgt
ggctttgggatatttgaagagcttggtcagttagtcacaagtctggccacgtgctatcatattagtttgaaaagcaatggagacacca
tctgctgatgctcaaagtggttacaaccaaaacacaaaaaagcagagctgtgggaagaattcaacattttgattatgcaagaagct
agtcccagccttgaaatccaccatctgcatcatgaaagacctaagtagttaaagccacagcagacatacagcttctatttccttacct
tcttcatcattaactacaggtcttggaagatttttgctgggaaaaagcttttattgcaagaactgtaatttattaacagggaaacatga
aataaatgtgtaaattctcctgcactcccactgtcattaaaaacggctttaagaaagagtattcagtaactgcctgcattgtgttgtga
ctttctactctgtgacacacagccttctgggcaaagcacatattctgccatgcatgtgggtcgtgccttggaaaatgggaacccacat
tcactgagggcctcttgatgagctttccccttgagaacagcgaggtctcatggatatcttctcttctccaagccaaataagcccagatc
cctcagctttccttcatggagaggctccagccctctgatcatgcctgcagcccttctctggacctgctccagcagccccacacgctcct
catgctgggaccccagatctgcacatggtattgcacatggggcctcacaacggcagagctgagagggacaattccctccctcagcct
ttaattctgcacgtacttaattttgtctgtattttttttgcaatagaatagcctgcatgctagttgctgtgtcgcacagctgaattcacta
ggttcctgtgaaacaaagggcaatcccacagccactgtagcacgtgaggagccacacaggtgctctaattcctacaggacaggcct
agggacagagcggccctaggactgccctcccgcacctcctagcttcaccttttgcccgcgatctttaagtaccctgaagcataaaca
gggaaagcgccgcccgcagcctcaccctgcttcccgcccaacgcggcaccgcccaggccgcagccgccccactaagagcactagcg
ccaccttctcaccccacccccaccacgcgttcctagcggccctgagagctgctgcgcatgcgccgcctgacgattcgccctcccattg
gctggcggtcgaagcacggcgggggcacgcggtggcggctatataaggcgtctcggaagacggcgccatgctatttggagcggag
agtgaaagttacagttcctggtgctggtagggagtgtggcgcggagcggagcgctgcggctcatcggaaccacaatggagccatag
cagagccgggcgtgggggcaagggcagtgcgtgctggggagggctccgtcgcgtggccacgtcgcgagagccgtcgggatggtgg
cgtcagggcggggggtgctgctaacgtgctcctggtcctgcaggtggctgctggcattcgccatggtgagcaagggcgaggagct
gttcaccggggtggtgcccatcctggtcgagctggacggcgacgtaaacggccacaagttcagcgtgtccggcgagggcgagggc
gatgccacctacggcaagctgaccctgaagttcatctgcaccaccggcaagctgcccgtgccctggcccaccctcgtgaccaccctg
acctacggcgtgcagtgcttcagccgctaccccgaccacatgaagcagcacgacttcttcaagtccgccatgcccgaaggctacgtc
caggagcgcaccatcttcttcaaggacgacggcaactacaagacccgcgccgaggtgaagttcgagggcgacaccctggtgaacc
gcatcgagctgaagggcatcgacttcaaggaggacggcaacatcctggggcacaagctggagtacaactacaacagccacaacg
tctatatcatggccgacaagcagaagaacggcatcaaggtgaacttcaagatccgccacaacatcgaggacggcagcgtgcagct
cgccgaccactaccagcagaacacccccatcggcgacggccccgtgctgctgcccgacaaccactacctgagcacccagtccgccc
tgagcaaagaccccaacgagaagcgcgatcacatggtcctgctggagttcgtgaccgccgccgggatcactctcggcatggacga
gctgtacaagGGAtccGGAGCTACTAACTTCAGCCTGCTGAAGCAGGCTGGAGACGTGGAGGAGAACC
CTGGACCTatgctcgagggagtgcaggtggaGacTatctccccaggagacgggcgcaccttccccaagcgcggccagacctgc

Figure 18 Cont'd gtggtgcactacaccgggatgcttgaagatggaaagaaagttgattcctcccgggacagaaacaagccctttaagtttatgctaggc
aagcaggaggtgatccgaggctgggaagaaggggttgcccagatgagtgtgggtcagagagccaaactgactatatctccagatt
atgcctatggtgccactgggcacccaggcatcatcccaccacatgccactctcgtcttcgatgtggagcttctaaaactggaatctgg
cggtggatccggagtcgacggatttggtgatgtcggtgctcttgagagtttgaggggaaatgcagatttggcttacatcctgagcatg
gagccctgtggccactgcctcattatcaacaatgtgaacttctgccgtgagtccgggctccgcacccgcactggctccaacatcgact
gtgagaagttgcggcgtcgcttctcctcgctgcatttcatggtggaggtgaagggcgacctgactgccaagaaaatggtgctggcttt
gctggagctggcgcGgcaggaccacggtgctctggactgctgcgtggtggtcattctctctcacggctgtcaggccagccacctgca
gttcccaggggctgtctacggcacagatggatgccctgtgtcggtcgagaagattgtgaacatcttcaatgggaccagctgccccag
cctgggagggaagcccaagctctttttcatccaggcctgtggtggggagcagaaagaccatgggtttgaggtggcctccacttcccc
tgaagacgagtcccctggcagtaaccccgagccagatgccaccccgttccaggaaggtttgaggaccttcgaccagctggacgcca
tatctagtttgcccacacccagtgacatctttgtgtcctactctactttcccaggttttgtttcctggagggaccccaagagtggctcctg
gtacgttgagaccctggacgacatctttgagcagtgggctcactctgaagacctgcagtccctcctgcttagggtcgctaatgctgttt
cggtgaaagggatttataaacagatgcctggttgctttaatttcctccggaaaaaacttttctttaaaacatcagtcgactatccgtac
gacgtaccagactacgcactcgacctcgacGGAtccGGAGAGGGCAGAGGAAGTCTGCTAACATGCGGTGACG
TCGAGGAGAATCCTGGACCTATGGAGGAGGAtTGGGAtACcGAaCTcGAGCAGGAGGCGGCAGCGG
CTTCCCAGGGGCGTTCTGAGGAGCAGGCGTGGATGGTGAGCTGTGTCCAGGGGAGGGCGGTGCGG
CAGGGAGCGGGGCACTGGGATGGCCCGGTCTGGGAAGGGGAGGCCGAGAGGCCTTCGCAGTGCT
TCCTGCAGCTCCCCGAGCAGTGCGAAGAAGGAGGTGCCGGGCTCTGCTGTGGGAGCCGAAGGCAC
GGAGCTGCCTGGGGAGGGAATGGCTGTGTGCCTGAGGTGCCAGAGACCGGCAAGGGCTGTACAG
AGAGGCAACGGTTTTGTGTACAAATCATTTGTATGGGAAACCACAAAATCTTGAAGCTTTATTACAT
GGCAGCGAAATACTTTGGTGTGAAGTAAAGGATAAGATAGAGGAGTGTAATGAGAGACAGCTAAA
TAATATTTTACTACTTGTGGGATGAGTGAATATCAGGAGGAACTGCTGTAAATTTCAGGAGGACCTG
TTGTGAATCTTCAGTAGTTGGCGCCGCTCTTACACATCTTACAGATGCCCCTTGAGCAAAGGGGGAT
AAGGAGAGATGAACGGGTTATCCAAACAGGTGATGAGCTAAAAGTACAGTTGCCTAAAGAAGTAG
TAGCATGTGCTATCAGAATGATAATTTTTGTTAGTTTGGGGTTAGTTTCCTGTAGTGGTAGATAGCCAC
AACAAGAAAACCGCTTAAGTTTTTGTAAAACAAAAAAAGCACGATCCAGAAGTAAAAAATATGGGT
AGTTTTTTTTGATGTTCCTCTCTCACCTGGTGCTTTGGCATACTAATATGTGTCTAATTGTATTAAACA
GGAGAAATTTAAACCTAGGCTTTGCTGGAAATAAAATGTTACAATGCTACAATGTGAAAAGTAGGT
GCTATTCTGAACTGTTTTGGGTGGAGTATCTGAATCTTTGAATAATTTAAGAGGGACTGACATATTTA
AAATACTTAAGGATAATCTGTAGCCATGCTGTAAAAGAACAACAGAAATGCAGTTGGGAAGGTGAT
GGAAATAGTTTTATTCATGTTACTGGTGGTCTGAAACCTTTCTAAGCTTAAACTGTAGAAAAAAATTG
CTTCAAAAGATTGCACTATTACTTTGGGCGACAAATGTTTTTAATTGGTTTTAAGTGTTTGTTAGCAA
AGTGAAGTTGATGCCACCATAAGTCTGACAGGAGGCAAGATAAACTTGTCTTCATACTGCTTGTGTA
TAACTTGGTTTTGATGACATTTGTGTGTGAACATTATGCACTTCAGTGTAGCGAAGTTTAAGAAACTT
TGAACAGAATAACTTGAAAGAGTGTGCACATGGGTGCAGAAGTCACTTTATTTCAGTTGGGAGACTT
AGCACCTAAATGCACTGTTAGTTCACATACACTTTGCTTGGCCTGAAGGTAACATTGTGATGTCGCTT
TTTTTCCCTGTAGGCTAACTCTGGCAGACCAAACAGCCCATCCCTCCGCTTCTCCAGCAGACCAAGCA
GCCCCTTGTCTGG

| Amino Acid | M | D | I | I | S | V | A | L | K | R | H | S | T | K | A | F | D |
|---|---|---|---|---|---|---|---|---|---|---|---|---|---|---|---|---|---|
| E.Coli Ntr | ATG | GAT | ATC | ATT | TCT | GTC | GCC | TTA | AAG | CGT | CAT | TCC | ACT | AAG | GCA | TTT | GAT |
| Chicken Opt | --- | --- | --- | --C | AGC | --G | --- | C-G | --- | A-A | --C | AG- | --C | --- | --C | --C | --- |

| Amino Acid | A | S | K | K | L | T | P | E | Q | A | E | Q | I | K | T | L | L |
|---|---|---|---|---|---|---|---|---|---|---|---|---|---|---|---|---|---|
| E.Coli Ntr | GCC | AGC | AAA | AAA | CTT | ACC | CCG | GAA | CAG | GCC | GAG | CAG | ATC | AAA | ACG | CTA | CTG |
| Chicken Opt | --- | --- | --G | --- | --G | --- | --C | --G | --- | --- | --- | --- | --- | --G | --C | --G | --- |

| Amino Acid | Q | Y | S | P | S | S | T | N | S | Q | P | W | H | F | I | V | A |
|---|---|---|---|---|---|---|---|---|---|---|---|---|---|---|---|---|---|
| E.Coli Ntr | CAA | TAC | AGC | CCA | TCC | AGC | ACC | AAC | TCC | CAG | CCG | TGG | CAT | TTT | ATT | GTT | GCC |
| Chicken Opt | --G | --- | --- | --C | AG- | --- | --- | --- | AG- | --- | --C | --- | --C | --C | --C | --G | --- |

| Amino Acid | S | T | E | E | G | K | A | R | V | A | K | S | A | A | G | N | Y |
|---|---|---|---|---|---|---|---|---|---|---|---|---|---|---|---|---|---|
| E.Coli Ntr | AGC | ACG | GAA | GAA | GGT | AAA | GCG | CGT | GTT | GCC | AAA | TCC | GCT | GCC | GGT | AAT | TAC |
| Chicken Opt | --- | --C | --G | --- | --C | --G | --C | A-A | --G | --- | --G | AG- | --C | --- | --C | --C | --- |

| Amino Acid | V | F | N | E | R | K | M | L | D | A | S | H | V | V | V | F | C |
|---|---|---|---|---|---|---|---|---|---|---|---|---|---|---|---|---|---|
| E.Coli Ntr | GTG | TTC | AAC | GAG | CGT | AAA | ATG | CTT | GAT | GCC | TCG | CAC | GTC | GTG | GTG | TTC | TGT |
| Chicken Opt | --- | --- | --- | --- | A-A | --G | --- | --G | --- | --- | AGC | --- | --G | --- | --- | --- | --C |

Figure 19A

| Amino Acid | A | K | T | A | M | D | D | V | W | L | K | L | V | V | D | Q | E |
|---|---|---|---|---|---|---|---|---|---|---|---|---|---|---|---|---|---|
| E.Coli Ntr | GCA | AAA | ACC | GCG | ATG | GAC | GAT | GTC | TGG | CTG | AAG | CTG | GTT | GTT | GAC | CAG | GAA |
| Chicken Opt | --C | --G | --- | --C | --- | --T | --- | --G | --- | --- | --- | G-- | --G | -A- | C-G | --- | --G |

| Amino Acid | D | A | D | G | R | F | A | T | P | E | A | K | A | A | N | D | K |
|---|---|---|---|---|---|---|---|---|---|---|---|---|---|---|---|---|---|
| E.Coli Ntr | GAT | GCC | GAT | GGC | CGC | TT T | GCC | ACG | CCG | GAA | GCG | AAA | GCC | GCG | AAC | GAT | AAA |
| Chicken Opt | --- | --- | --- | --- | A-A | --C | --- | --C | --C | --G | --C | --G | --- | --C | --- | --- | --G |

| Amino Acid | G | R | K | F | F | A | D | M | H | R | K | D | L | H | D | D | A |
|---|---|---|---|---|---|---|---|---|---|---|---|---|---|---|---|---|---|
| E.Coli Ntr | GGT | CGC | AAG | TTC | TTC | GCT | GAT | ATG | CAC | CGT | AAA | GAT | CTG | CAT | GAT | GAT | GCA |
| Chicken Opt | --C | A-A | --- | --- | --- | --C | --- | --- | --- | A-A | --G | --- | --- | --C | --- | --- | --C |

| Amino Acid | E | W | M | A | K | Q | V | Y | L | N | V | G | N | F | L | L | G |
|---|---|---|---|---|---|---|---|---|---|---|---|---|---|---|---|---|---|
| E.Coli Ntr | GAG | TGG | ATG | GCA | AAA | CAG | GTT | TA T | CTC | AAC | GTC | GGT | AAC | TT C | CTG | CTC | GGC |
| Chicken Opt | --- | --- | --- | --C | --G | --- | --G | --C | --G | --- | --G | --C | --- | --- | --- | --- | --- |

| Amino Acid | V | A | A | L | G | L | D | A | V | P | I | E | G | F | D | A | A |
|---|---|---|---|---|---|---|---|---|---|---|---|---|---|---|---|---|---|
| E.Coli Ntr | GTG | GCG | GCT | CTG | GGT | CTG | GAC | GCG | GTA | CCC | ATC | GAA | GGT | TT T | GAC | GCC | GCC |
| Chicken Opt | --- | --C | --C | --- | --C | --- | --T | --C | --G | --- | --- | --G | --C | --C | --T | --- | --- |

Figure 19B

| Amino Acid | I | L | D | A | E | F | G | L | K | E | K | G | Y | T | S | L | V |
|---|---|---|---|---|---|---|---|---|---|---|---|---|---|---|---|---|---|
| E.Coli Ntr | ATC | CTC | GAT | GCA | GAA | TTT | GGT | CTG | AAA | GAG | AAA | GGC | TAC | ACC | AGT | CTG | GTG |
| Chicken Opt | --- | --G | --- | --C | --G | --C | --C | --- | --G | --- | --G | --- | --- | --- | --C | --- | --- |

| Amino Acid | | V | V | P | V | G | H | H | S | V | E | D | F | N | A | T | L | P |
|---|---|---|---|---|---|---|---|---|---|---|---|---|---|---|---|---|---|---|
| E.Coli Ntr | | GTT | GTT | CCG | GTA | GGT | CAT | CAC | AGC | GTT | GAA | GAT | TTT | AAC | GCT | ACG | CTG | CCG |
| Chicken Opt | | --G | --G | --C | --G | --C | --C | --- | --- | --G | --G | --- | --C | --- | --C | --C | --C | --C |

| Amino Acid | K | S | R | L | P | Q | N | I | T | L | T | E | V | * |
|---|---|---|---|---|---|---|---|---|---|---|---|---|---|---|
| E.Coli Ntr | AAA | TCT | CGT | CTG | CCG | CAA | AAC | ATC | ACC | TTA | ACC | GAA | GTG | TAA |
| Chicken Opt | --G | AGC | A-A | --- | --C | --G | --- | --- | --- | G-G | --- | --G | --- | -G- |

Figure 19C

| *Gene* | PGCs | EGKX | ESC | Non-pluri |
|---|---|---|---|---|
| ***DAZL*** | 76371.21 | 720.2398 | 530.0013 | 34.21324 |
| *GASZ* | 8639.847 | 246.7869 | 203.9233 | 6.402586 |
| *DMRTB1* | 8677.622 | 79.0355 | 63.32094 | 8.482617 |
| *TDRD9* | 12636.25 | 299.1649 | 167.5263 | 60.6653 |
| ***RNF17*** | 16936.69 | 301.4385 | 105.7011 | 24.44505 |
| *TDRD5* | 1973.104 | 127.1841 | 74.78851 | 7.138669 |
| ***TUBA1B,TUBA1C*** | 21375.99 | 50.52952 | 38.89003 | 79.64034 |
| *SMC1B* | 590.2944 | 14.23563 | 5.983081 | 4.788909 |
| *ADAD1* | 3943.651 | 153.2249 | 136.1151 | 70.10129 |
| *DDX43* | 3988.183 | 42.21711 | 28.91822 | 25.21776 |
| *DMRT1* | 879.4701 | 59.75056 | 99.21943 | 10.70041 |
| *SLC38A11* | 1668.314 | 146.6464 | 45.87029 | 9.203512 |
| *PNLDC1* | 6364.124 | 111.4112 | 164.0361 | 103.1999 |
| *TDRD15* | 3929.14 | 203.6151 | 69.80261 | 24.25653 |
| *SUB1L1* | 694.1263 | 28.4978 | 11.96616 | 27.12091 |
| ***DDX4*** | 27426.86 | 1287.443 | 587.3391 | 98.06619 |
| *FKBP6* | 3625.805 | 60.0719 | 50.3576 | 89.92549 |
| *ZNF541* | 2283.049 | 119.5138 | 177.4981 | 191.5858 |
| ***STK31*** | 16248.82 | 155.344 | 90.24481 | 252.978 |
| ***FDFT1*** | 54036.77 | 2170.061 | 2147.926 | 2896.83 |
| *KCNH7* | 3448.285 | 88.26523 | 4.985901 | 36.52859 |
| *TEX14* | 5239.466 | 221.1618 | 116.1715 | 388.9234 |
| *KCNU1* | 525.8504 | 38.58582 | 3.988721 | 16.71491 |
| *GTSF1* | 13376.22 | 1104.093 | 1403.033 | 629.0127 |
| *GNG10* | 6338.832 | 390.3887 | 400.3678 | 556.5592 |
| *AGBL4* | 2731.956 | 242.3925 | 32.90695 | 122.2269 |
| *FSIP1* | 571.5997 | 36.93096 | 10.96898 | 39.48513 |
| ***gga-mir-6611*** | 16610.91 | 870.5166 | 75.2871 | 802.5542 |
| *DNAH12* | 6920.019 | 629.816 | 307.6301 | 677.8306 |
| *MOV10L1* | 15132.2 | 475.3432 | 152.5686 | 759.5825 |
| *ST8SIA2* | 3387.322 | 148.868 | 115.1743 | 223.8055 |
| *SOX21* | 1658.313 | 105.1437 | 229.85 | 117.8102 |
| *ELAVL4* | 23820.55 | 768.6101 | 631.7136 | 2015.512 |

Figure 20

| Chicken surrogate host line | Number of embryos | Number of embryos GFP+ (%) | Number of embryos with black skin |
|---|---|---|---|
| Dazl-aviCaspase9 | 26 | 2 (7.7) | 24 |
| Dazl-iCaspase9 | 56 | 0 (0) | 51 |

GENETICALLY MODIFIED STERILE AVIANS AND METHOD FOR THE RECONSTITUTION THEREOF

FIELD OF THE INVENTION

The present invention relates to methods of generating genetically modified and/or wildtype birds, for example chickens, from reproductive cells, and birds produced using such methods.

BACKGROUND TO THE INVENTION

The production of bird breeds from isolated reproductive cells is at present a largely inefficient and difficult process. A particular problem associated with the generation of genetically modified birds is the stable transmission of the reproductive cells containing the genetic modification into the offspring of the birds and subsequent generations of such birds. In particular, when using conventional methods, germ cell transmission is particularly inefficient, as a result of competition in the formation of functional gametes between the donor germ cells, which may or may not be genetically modified, and the endogenous germ cells.

Although diploid germ cells can be transplanted from one bird into a host bird, the proportion of offspring produced from the subsequently formed gametes is variable, with some or all of the offspring being formed from gametes derived from the endogenous (host bird) germ cells (Nakamura et al (2010) *Reprod Fert Dev* 22(8): 1237-1246; Song et al (2014) *Biol Reprod* 90(1): 15). Endogenous (host) germ cells can be destroyed using irradiation or chemotherapeutic reagents such as busulphan but these toxic reagents can also kill the animal as well as the endogenous germ cells. Tagami used chemical treatment to generate sterile surrogate host chickens (Nakamura et al (2010) Biol Reprod 83(1):130-7). The inventors and Nakamura used gamma irradiation to kill endogenous germ cells (MacDonald et al (2010) Plos One 5(11): e15518; Nakamura et al, (2012) *J Reprod Dev* 58(4): 432-437). However, although the number of offspring produced from the donor germ cells was increased after treatment, not all the offspring were derived from the donor germ cells and the treatment killed many of the host chickens.

Sterile mammals and fish transgenic lines have been made that express a gene product (Nitroreductase, Ntr) in the germ cells that will kill the germ cells in the presence of a prodrug. The iC9 (induced caspase9) gene has been used to kill stem cells in humans and mice and to kill endothelial cells in transgenic mice. Such techniques would not be expected to be directly transferable to birds, given the different results obtained using germ cell modification techniques when applied to mammals and birds. For example, the inventors' previous work has produced a female chicken with no germ cells through a genetic mutation in the DDX4 gene through gene editing technology. (Taylor et al., Development 2017). The inventors did not expect the female chicken to be sterile as while male mammals with a mutant Ddx4 gene are sterile, female mammals with a mutant Ddx4 have normal fertility. Germ cell modification techniques may thus have very different effects in mammals than in birds. Sterility also depends on when the endogenous reproductive cells die during development. In birds, the DDX4 sterile females contain the reproductive cells up to hatching which can compete with donor germ cells injected into the gene modified host embryo.

SUMMARY OF THE INVENTION

The present invention addresses many of the problems of the prior art. The inventors have surprisingly shown that by employing genetic engineering to express a recombinant protein in the germ cells that will selectively kill the host germ cells on demand, for example on exposure to a particular pro-drug or inducer, without killing other cells in the host chicken, highly efficient integration of donor germ cells may be achieved. Germplasm (reproductive cells) from different bird species can be transferred to this host bird and the genetics of the offspring will be derived from the transferred material (FIG. 1)

Whilst sterile mammals and fish transgenic lines have been made that expression gene product, differences in protein activity and function in bird and mammalian species and differences in gene function and activity between bird and mammalian species means that it would not be expected that techniques utilised in mammals and fish would be transferrable to birds and cell modification techniques may thus have very different effects in birds than in mammals. Sterility also depends on when the endogenous reproductive cells die during development (temporal nature of gene or protein activity). Many different loci must be assayed in birds to determine if they will expression the transgene at the appropriate developmental stage, i.e. if the germ cells can be 100% ablated during embryonic development.

Accordingly, a first aspect of the present invention provides a transgenic avian comprising a transgene in the germ cells of said avian, wherein the activity of the protein encoded by said transgene is inducible via an exogenous inducing agent and the activity of said protein, when induced, causes death of said germ cells.

A second aspect of the invention provides a transgene construct comprising (i) a first nucleotide sequence, wherein the activity of the protein encoded by said first nucleotide sequence causes death of germ cells in the presence of an exogenous induction agent and (ii) a second nucleotide sequence which targets said construct to avian germ cells.

A third aspect provides method of modifying the germplasm of an avian, said method comprising administering a transgene construct into a fertilised egg of said avian and incubating said egg, wherein said transgene construct is the transgene construct of the second aspect of the invention and wherein said transgene construct is integrated into germ cells of said embryo.

A fourth aspect of the invention provides a transgenic avian comprising the transgene construct of the second aspect of the invention or produced by the method according to the third aspect of the invention.

In the invention, the avian may be any suitable bird. For example, the avian may be of the order galliformes, aseriformes, passeriformes, gruiformes, Struthioniformes, rheiformes, casuariformes, apyerygiformes, otidiformes, columbiformes, sphenisciformes, cathartiformes, accipitriformes, strigiformes, psittaciformes, charadriiformes or falconiformes. Suitably, the avian is a chicken, turkey, duck, goose, quail, pheasant, grouse, guinea fowl, pigeon, ostrich, emu, song bird, parrot, finch, sparrow, penguin, or falcon. In one embodiment, the avian is a chicken.

In the invention, the transgene construct of and for use in the invention is targeted to germ cells. In one embodiment, the germ cells are primordial germ cells. In another embodiment, the germ cells are adult germ cells. Preferably, said construct is targeted to a locus of the avian genome which is preferentially expressed in primordial germ cells or germ cells in the gonad of the embryo or in the testes and ovary of the adult bird. Preferably, the locus is expressed only in primordial germ cells or germ cells in the gonad of the embryo or the adult bird. In one embodiment, the transgene construct is targeted to one of the following loci that, in a bird, are only expressed in reproductive cells: DAZL, DDX4, DMRT1, MIR383, TDRD15, TDRD5, FKB6, GASZ, DMRTB1, TDRD9, GTSF1, MOV10L1, STK31, RNF17, FDFT1, GNG10, DDX43, KCNH7, SOX21 TUBA1B, or PNLDC1. In another embodiment, said construct is targeted to one or more of the following RNA encoding genes: MSTRG.9846 (2:40789480-40848190), MSTRG.10457(2:71880785-71991485), MSTRG.17017 (3: 85453009-85462029). Suitably the transgene construct is targeted to one of the following loci DAZL, RNF17, TUBA1B, TUBA1C, STK31, FDFT1, gga-mir-6611. Advantageously, the transgene is targeted to loci that are most highly expressed in chicken PGCs. Advantageously, the transgene is targeted to loci that are most highly expressed in the particular avian PGCs, for example goose, duck or the like.

Figure 21:
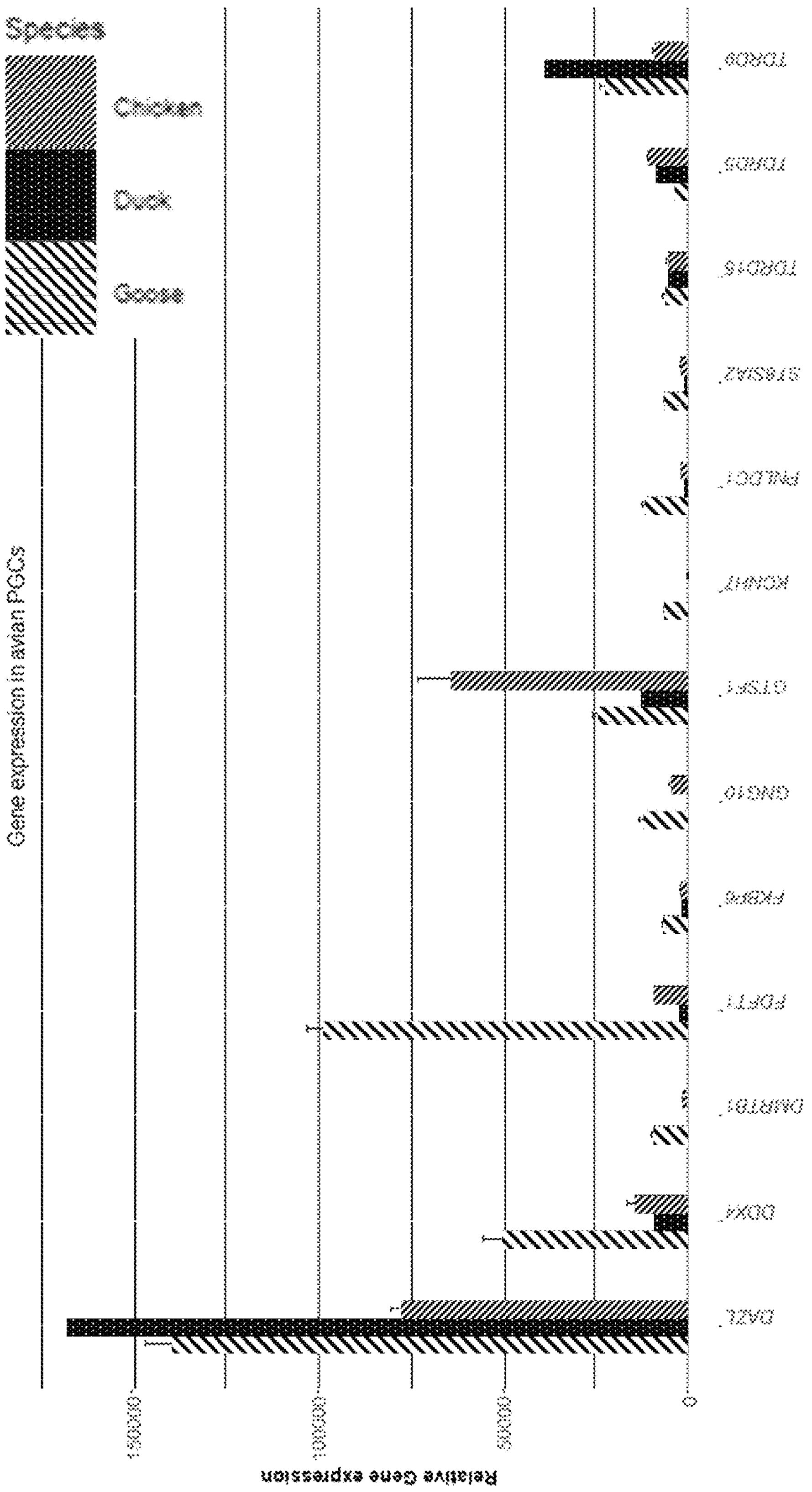

Comparison of the RNA transcriptome of primordial germ cells between avian species determined genes that are expressed at high levels in germ cells of most bird species. This analysis discovered DAZL as highest in most bird species, GTSF1 is second highest for goose, and TDRD9 is second highest for duck germ cells. Thus, different genomic locations may function better in particular birds species. FIG. 21 shows expression levels in Chicken, Duck and Goose respectively.

Suitably the transgene is targeted to loci that expressed at the correct time in growth and reproductive cycle of the avians to allow development of the avian and the reproductive system of the avian but minimise competition of donor and host reproductive cells. For example, in embodiments the inventors determined that due to the temporal nature of expression provided, the DDX4 sterile females contained reproductive cells up to hatch which can compete with donor germ cells. The germ cells only died post-hatch. As will be appreciated the ability to allow expression until exogenous agent is applied, to modulate expression through the provision of the exogenous agent and the ability to consider the temporal nature of the expression may provide a more advantageous system that a simple knock out of reproductive gene in the host.

Suitably the cell death ablation gene and the locus to which it is targeted may be selected to ablate the germ cells during embryonic development as required.

Cell death ablation transgene must be sufficiently active to ablate the majority of the germ cells during embryonic development. DDX4 may be selected as a second choice to dazl as a locus in chickens. As will be appreciated, providing a cell ablation transgene with increased apoptosis activity could overcome the deficiency of ablation indicated using nitroreductase. For example, enhanced activity of iCaspase9 would allow use of the DDX4 locus. As will be appreciated by those skilled in the art, a screening assay may be used to identify amino acid changes in proteins which provide for ablation or potential ablation (Caspase9 or nitroreductase or any other cell death inducing gene) and the screen used to make such proteins sufficiently active or more active to provide ablation of germ cells at functionally useful levels/ with increased efficiency. Subsequently, such proteins could be introduced into any of the listed germ cell specific loci.

In embodiments, the caspase 9 gene, (mammalian amino acid version or a chickenised amino acid version(aviCaspase9) was found to be particularly advantageous to confer ablation of host cells. As noted in the examples, aviCaspase9 was determined not to ablate all germ cells when provided in the cell culture when introduced into the DDX4 locus of the chicken cell.

Figure 23A:
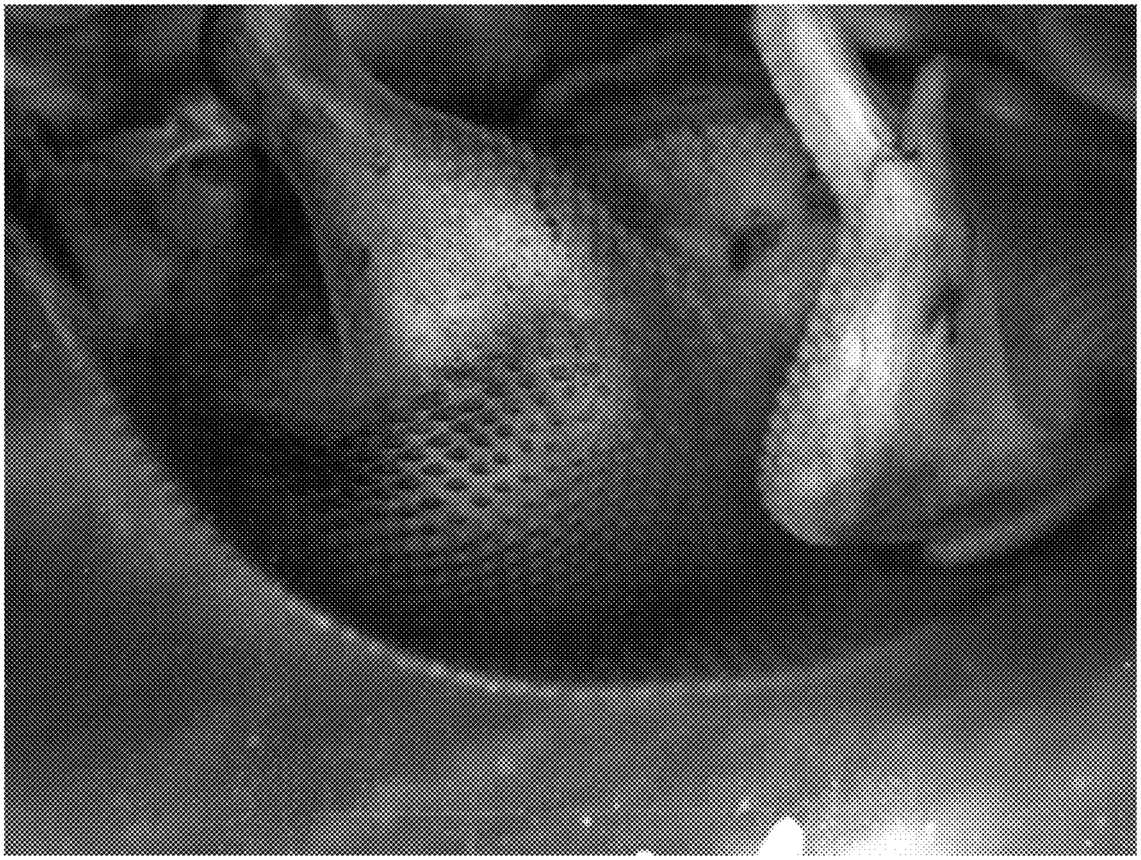
Figure 23B:

Suitably a mammalian amino acid caspase 9 transgene may be provided to ablate germ cells when targeted at the DAZL locus. Suitably ablation provides for substantially produce pure donor offspring, for example greater than 75%, greater than 80%, greater than 85%, greater than 90%, greater than 95%, greater than 97%, greater than 99%, 100%. Suitably iCaspase9 may be utilised in chicken for sterile ablation. The iCaspase9 gene was determined to provide complete sterile ablation in the chicken for (FIG. 23).

In a particular embodiment the transgene can be a cDNA targeted to the avian DAZL locus, in particular the c-terminal end of the avian DAZL locus. The inventors have determined that not only is DAZL expressed at high levels in the primordial germ cells and thus allows selective ablation of cells, it also provides sufficient expression of toxic protein to provide ablation. Moreover, the inventors have determined that in addition to the expression level provided by a loci, the timing of expression (temporal nature of expression) is important. DAZL is expressed at an early stage in primordial germ cells in the avian embryo. The temporal expression of DAZL is therefore also advantageous for it to be used in expression of toxic proteins or apoptosis inducing proteins. Suitably iCaspase9 under control of DAZL is particularly advantageous. For example, the inventors determined iCaspase9 transgene functions well in the DAZL locus of chicken.

The expression level provided the construct and the timing of expression is considered to be important when considering expression of toxic proteins or apoptosis inducing proteins (e.g. caspase) in contrast to the use of knockouts where disruption of a loci may be sufficient. The degree of ablation produced by the transgene can be altered by the genetic location of the transgene, for example inserted at the 5' end of a gene or inserted at the 3' end of a gene, or as an independent transgene whose expression is driven by the regulatory regions of genes only expressed in the reproductive cells of birds.

As described herein, the transgene construct of and for use in the invention comprises a first nucleotide sequence, the protein expressed from which causes death of germ cells in the presence of an exogenous induction agent. In some embodiments the transgene encodes a protein the activity or expression of which is inducible via an exogenous inducing agent, wherein the expressed protein causes death of said germ cells in the presence of an exogenous inducing agent.

Suitably the transgene may comprise a portion that encodes an inducible dimerization domain and an apoptosis inducing domain. Suitably the inducible dimerization domain may be a chemically inducible dimerization domain. In the presence of a dimerization inducing agent, for example a dimerization inducing chemical compound, the expressed protein dimerises causing apoptosis of the endogenous germ cells.

In the invention, any suitable apoptosis inducing domain may be used. In one embodiment, the apoptosis inducing domain comprises or consists of a caspase gene encoding a caspase protein. Such caspase proteins are caspase 2, 3, 4, 6, 7, 8, 9 or 10. Such caspase protein can contain mammalian or avian or other vertebrate amino acid sequences. In one embodiment, the caspase is caspase 9.

Accordingly, suitably an inducible caspase9 (iC9) gene may be expressed in the germ cells of an avian, for example a chicken. When exposed to a chemically induced dimerization (CID) drug, the Capase9 will dimerise and be activated and will then cause the germ cells containing the dimerised Caspase9 to apoptose.

Suitably expression of said caspase gene may be induced by application of a dimerization agent via the dimerization domain that induces dimerization. Suitable dimerization agents which may be used with the invention include AP20187 ligand (molecule B/B, Takara) or chemical variations of this product FK1012, AP1501, AP1903.

In one such embodiment, the transgene is a cDNA encoding the FKBP12 dimerisation domain and a caspase 9 gene targeted to a genetic locus selected from DAZL or DDX4, particularly DAZL or DDX4 in chicken.

In another embodiment, said transgene may encode a dimerisation domain fused to an apoptosis inducing domain, e.g. a caspase gene that would lead to dimerisation of the encoded protein after the delivery of a dimerisation stability drug. For example, the transgene may encode a stabilisable polypeptide linker (SPL) attached to a caspase molecule. Addition of a compound like Asunaprevir and Telaprevir would stabilise the dimerisation domain of the caspase molecules leading to the activation of the caspase molecule and activation of cell death (Jacobs et al (2018) *Nature Methods* 15: 523-526)

In an alternative embodiment, the transgene can encode an enzyme that converts prodrugs into cytotoxic metabolites. In such an example a prodrug (which acts as the exogenous inducing agent) can be provided to the endogenous germ cells and expression of the transgene, for example a cDNA encoding a bacterial nitroreductase gene, can provide an enzyme which converts the prodrug into a cytotoxic metabolite.

In such a system, any suitable enzyme and prodrug activated by said enzyme may be used. For example, where the enzyme is nitroreductase, the prodrug may be CB1954 or metronidazole.

In one such embodiment, the transgene is a cDNA encoding the nitroreductase gene targeted to a genetic locus selected from DAZL or DDX4, particularly DAZL or DDX4 in chicken.

In one embodiment, the transgene construct of and for use in the invention comprises cDNA and a 2A or an IRES sequence such that the recombinant protein is expressed at equal levels to the endogenous gene. For example a 2A peptide sequence may be linked to the cDNA so that the recombinant protein is expressed at equal levels to the endogenous gene.

In one embodiment, a nucleotide sequence from a locus that, in a bird, is only expressed in germ cells or reproductive cells (examples of such loci, including DAZL and DDX4 are given above), wherein said nucleotide sequence comprises the regulatory regions and the first exon up to the first coding methionine, is linked to the cDNA. This region of DNA can be introduced into the bird in any suitable way that will express the recombinant protein specifically in the germ cells, for example in a transposon.

Examples of DAZL AND DDX4 repair templates of and for use in the invention are shown in FIGS. 15, 16, 17 and 18. Such repair templates constitute further independent aspects of the invention.

In the methods of the invention, any suitable means may be employed to target the transgene construct to germ cells. Suitably, a CRISPR based system, such as a CRISPR/cas system or CRISPR/cfp based system may be used to target the transgene to the germ cells. In such a system, a guide RNA may target the construct to the germ cells.

According to a further aspect of the present invention, there is provided a kit comprising a transgenic construct of the second aspect of the invention and a site-specific nuclease, such as Cas9, to target the construct to a genetic locus transcribed specifically in germ cells.

In an alternative embodiment to a CRISPR based system for targeting the transgene construct to germ cells, a transposon based system may be used to target the transgene construct to germ cells. In such a system targeting may be achieved by incorporating within a transposon (i) regulatory regions from a gene preferentially expressed, preferably exclusively expressed, in germ cells together with (ii) said first nucleotide sequence. For example, such a transposon could comprise regulatory regions from DDX4 or DAZL, a caspase 9 gene and a dimerization domain (suitably DAZL and icaspase9). The first nucleotide sequence would be expected to be expressed only in germ cells. Thus, on application of the exogenous inducing agent, only germ cells would be expected to be killed.

The transgene construct of the second aspect of the invention may be used to modify the germplasm of an avian. By targeting the transgene construct to germ cells and administering the induction agent, the transgene is activated such that it may selectively kill the endogenous germ cells. Suitably the activation of the transgene of the germ cells causes the germ cell number to be reduced by at least 10%, at least 20%, at least 30%, at least 50%, at least 70%, at least 90%, up to 100% from normal values. Suitably, the process provides an avian that lacks endogenous reproductive cells.

Suitably the transgene when induced may be expressed in the presence of the exogenous inducing agent at a level sufficient to cause the germ cells to die when cultured in vitro.

After or during the killing of endogenous germ cells via, e.g. activation of the protein encoded from an apoptosis inducing domain or the conversion by an enzyme encoded from the transgene of a prodrug into a cytotoxic metabolite, an avian lacking germ cells (host bird) may be provided with cells (transplanted cells), for example germ cells from another avian of the same or different avian species, such that the host bird produces offspring with the genetics of the transplanted cells. Suitably the process may comprise the step of transplanting germ cells from a donor avian into the surrogate avian.

Suitably induction of activity of a protein encoded from the transgene may be stopped prior to transplantation of the donor cells.

Suitably the transplanted cells from the donor avian may be derived from frozen cells.

As will be appreciated, germ cells transplanted into a surrogate host from a donor avian will have an increased chance to compete with endogenous germ cells that were present in the surrogate host due to the effect of the transgene.

Suitably the transplanted cells may be gene-edited reproductive cells. Suitably the gene-edited reproductive cells may be from the same or a different avian species as that of the host avian.

Suitably the process may comprise the step of providing an avian with a genome of the transplanted cells. Suitably the surrogate host avian may be used to produce a plurality, for example a flock, of gene edited avians from gene edited reproductive cells from that avian species or from another avian species.

In one aspect of the invention there is provided a method of producing a surrogate host avian, said method comprising inserting a transgene construct into fertilised eggs of an avian and incubating said eggs to hatching, wherein said transgene construct is integrated into germ cells of said embryo and the protein expressed from which transgene construct causes death of said germ cells in the presence of an exogenous inducing agent. The method enables said transgene construct to be integrated not only into the germ cells of said embryo but also the germ cells of all offspring produced subsequently from the bird resulting from said embryo.

Suitably the method may further comprise treating the surrogate host produced with the exogenous inducing agent to cause death of said endogenous germ cells. Suitably the method further comprises transplanting exogenous reproductive cells into said surrogate host.

Suitably the method further comprises crossing male and female offspring from one or more of said surrogate host avian to produce offspring avians with germ cells having the genetic characteristics of the transplanted germ cells. Detection of offspring from the transplanted germ cells can be identified by standard genomic sequencing techniques.

The surrogate host bird can be used for the transplantation of cells, in particular, germ cells from other avian species. The germ cells may be primordial germ cells, embryonic germ cells, gonocytes. The germ cells may be transplanted via transplantation of adult testes or ovaries. The surrogate host bird produces offspring with the genetics of the transplanted cells.

The surrogate host bird may be used to revive bird species from frozen genetic material stored in the form of reproductive cells. The revived bird species will have a genome of that of the frozen reproductive cells.

Embodiments of the present invention will now be described, by way of example only, with reference to the accompanying figures in which:

FIG. 1 Diagram of germ cell transplantation into sterile host.

Figure 2:
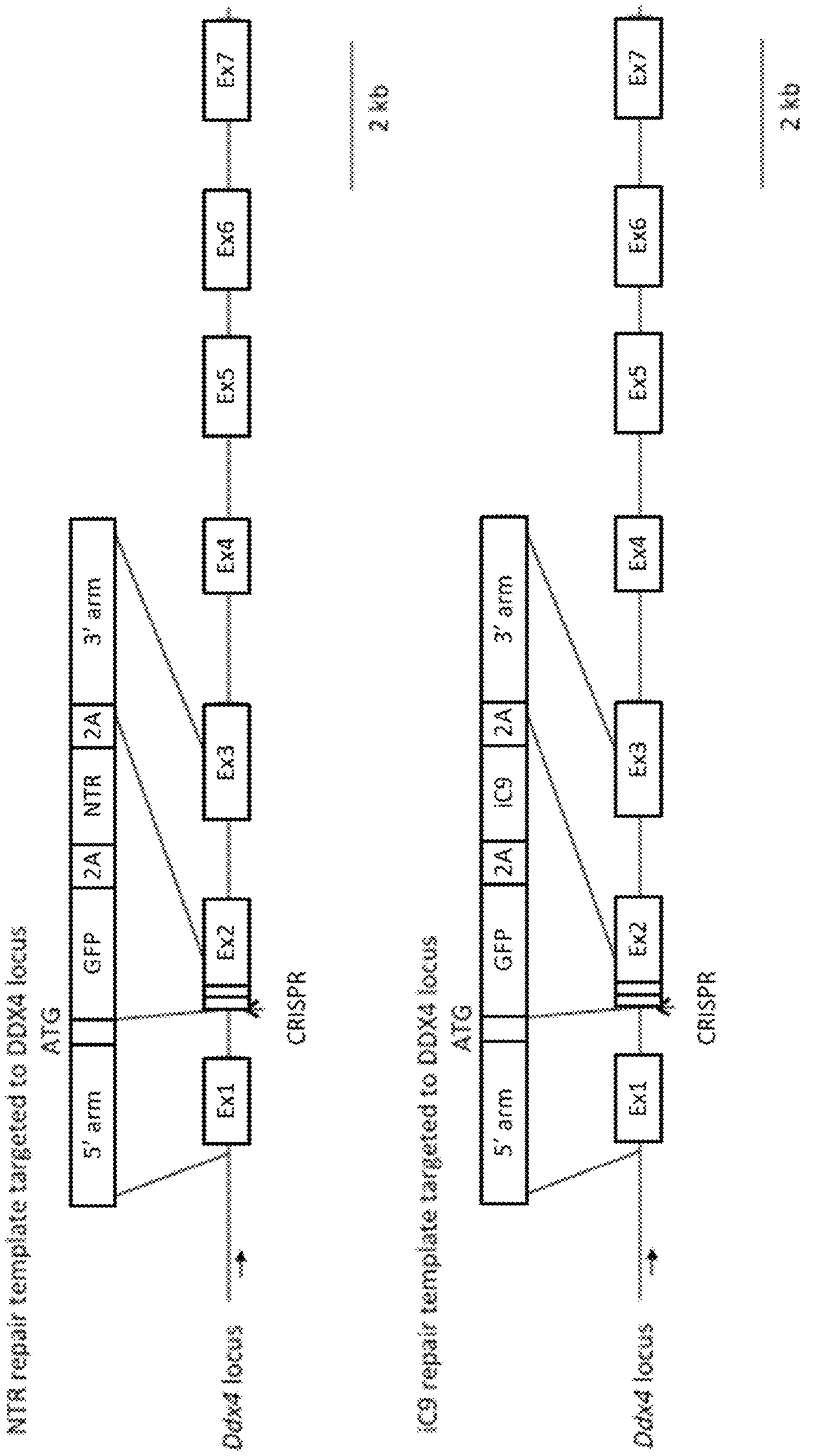

FIG. 2 Schematic showing targeting of NTR and iCaspase9 (iC9) to the DDX4 locus. NTR repair template targeted to DDX4 locus and ic9 repair template targeted to DDX4 locus.

Figure 3:
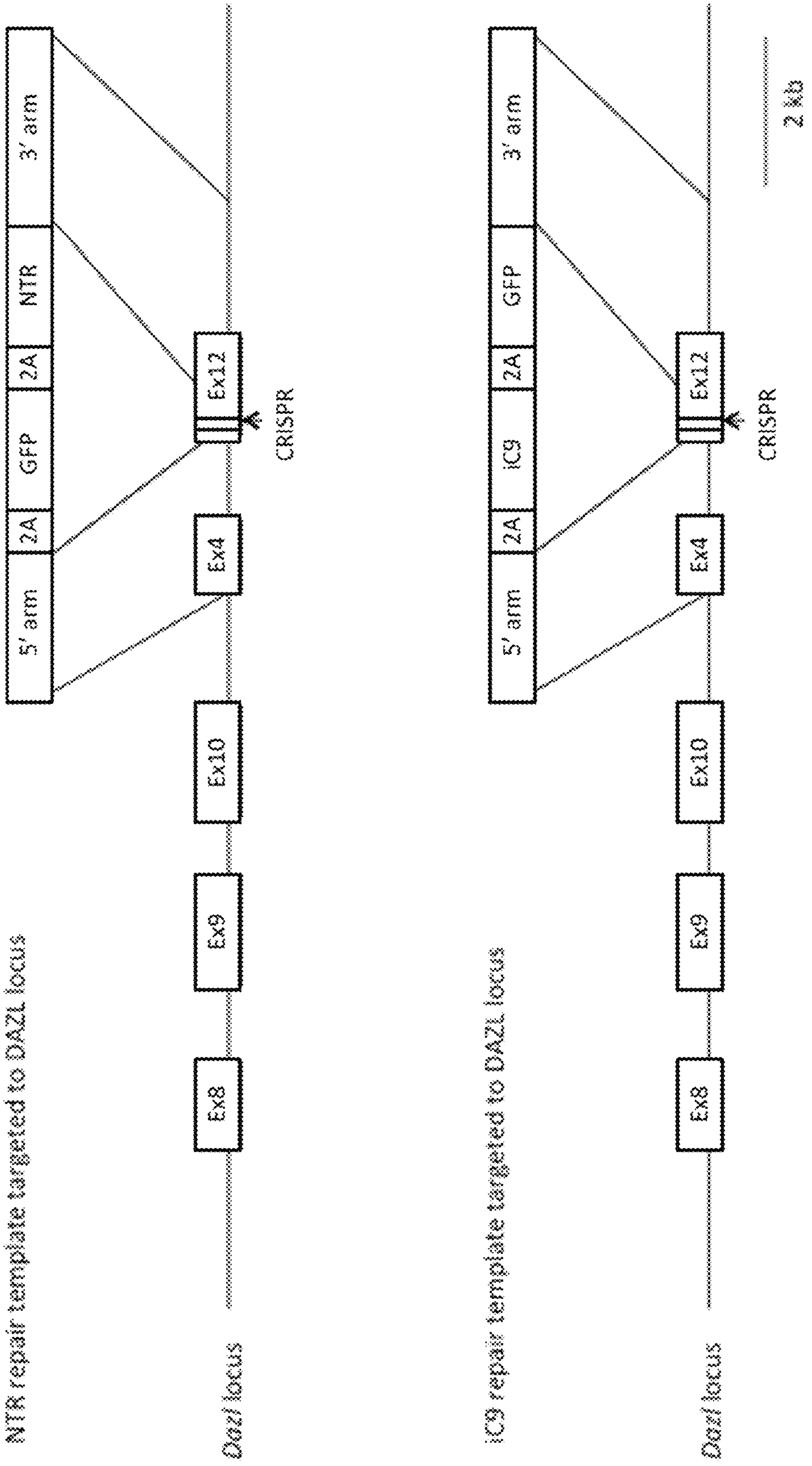

FIG. 3 Schematic showing targeting of NTR and iCaspase9 (iC9) to the DAZL locus. NTR repair template targeted to DAZL locus and ic9 repair template targeted to DAZL locus.

Figure 4:
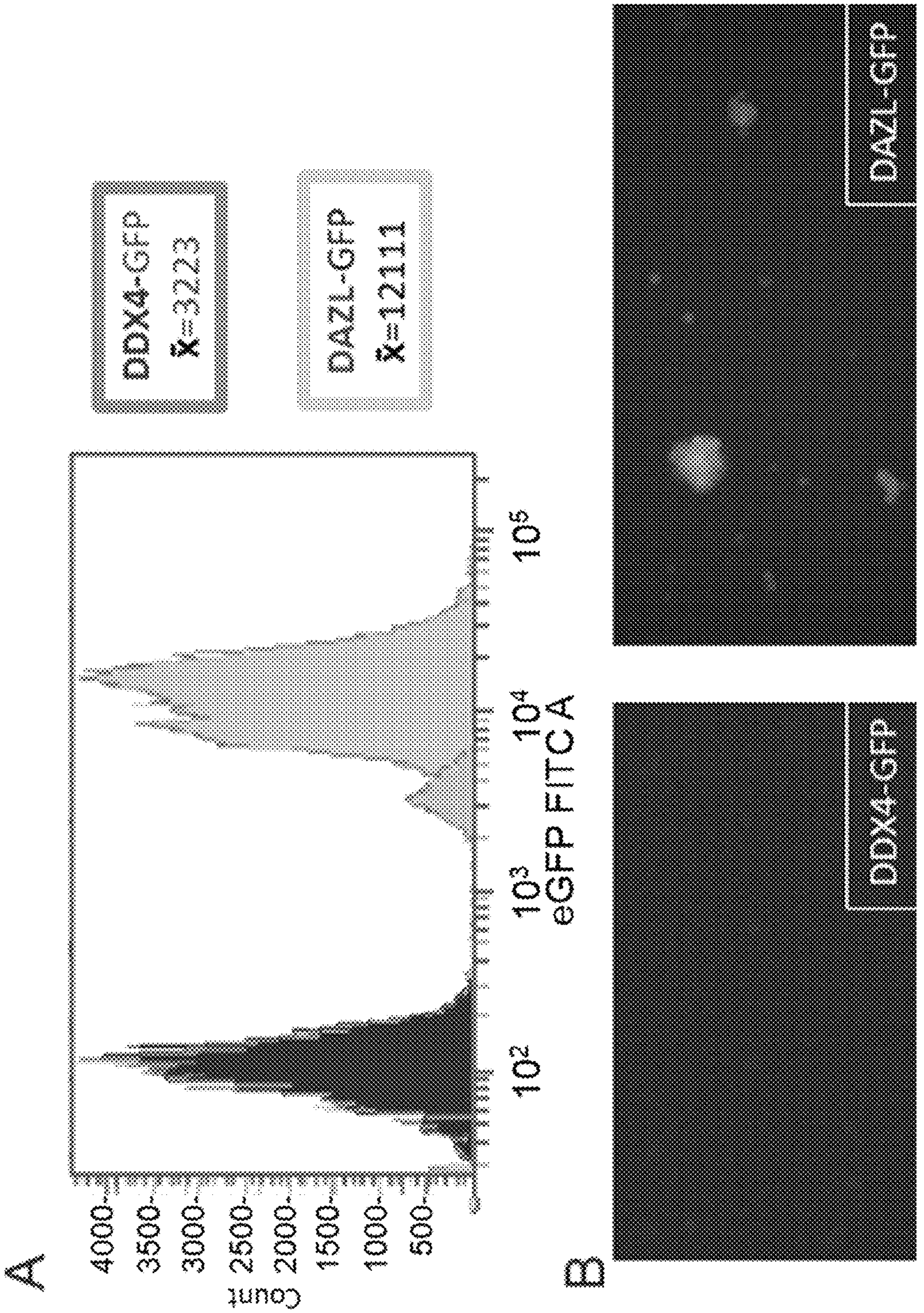

FIG. 4 PGCs targeted to the DAZL locus express ~4× the amount of GFP as cells targeted to the DDX4 locus. PGCs containing GFP targeted to the Dazl locus express 3.8 times higher GFP fluorescence than PGCs containing GFP targeted to the Ddx4 locus. A. Flow cytometry analysis of GFP fluorescence B. Micrograph of Targeted PGCs.

Figure 5:
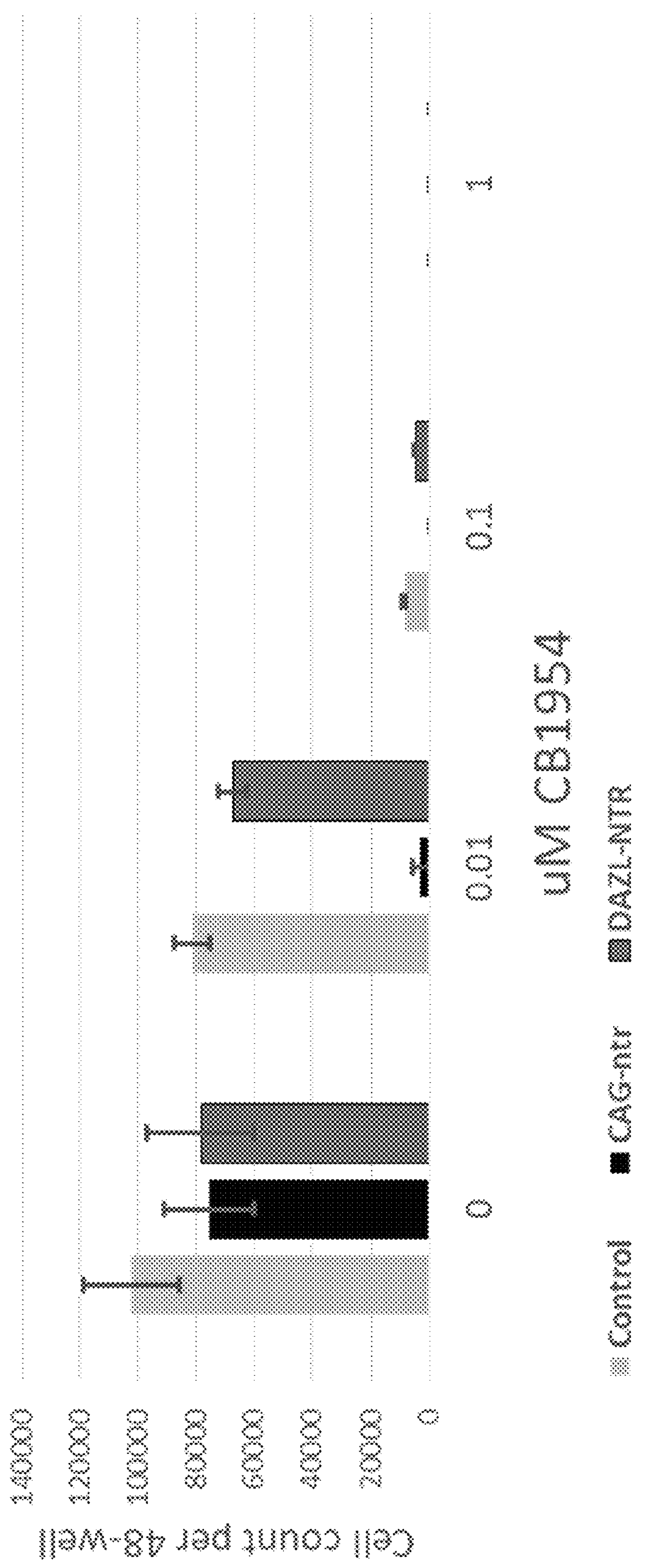

FIG. 5 500 PGCs (Control, CAG-NTR or Dazl-NTR) were cultured in the presence or absence of the nitroreductase pro-drug CB1954 (n=2 for each concentration of pro-drug). After 10 days the total cell number was counted for each well. N=6 for each data point, from three independent experiments.

Figure 6:
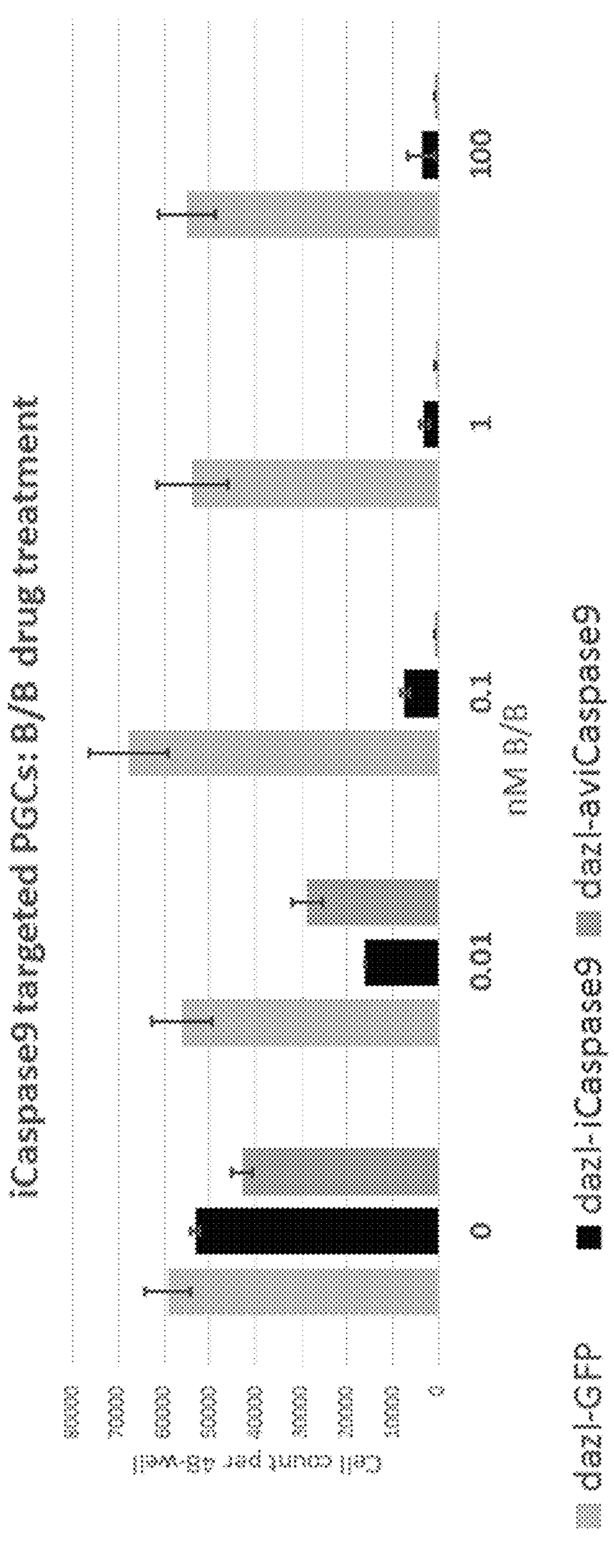

FIG. 6 500 PGCs (dazl-GFP, dazl-human-Caspase or dazl-chicken-Caspase) were cultured in the presence or absence of the dimerization molecule B/B. After 10 days the total cell number was counted for each well. N=6 for each data point, from three independent experiments.

FIG. 7 B/B treatment ablates injected DAZL-iCasp9 targeted PGCs. Stage HH 16 embryos were injected with 3500 PGCs transfected with CRISPR reagents to insert an inducible caspase gene and GFP at the dazl locus, and 3500 PGCs transfected with a transposon to insert a cassette for TdTomato expression randomly in the genome. After injection, embryos were dosed with 50 μl of 1× Pen/Strep with or without 25 nM of the dimeriser drug B/B. At 8 days of development, gonads were dissected and viewed under fluorescence. Images are representative of three independent injections for each treatment.

Figure 8:
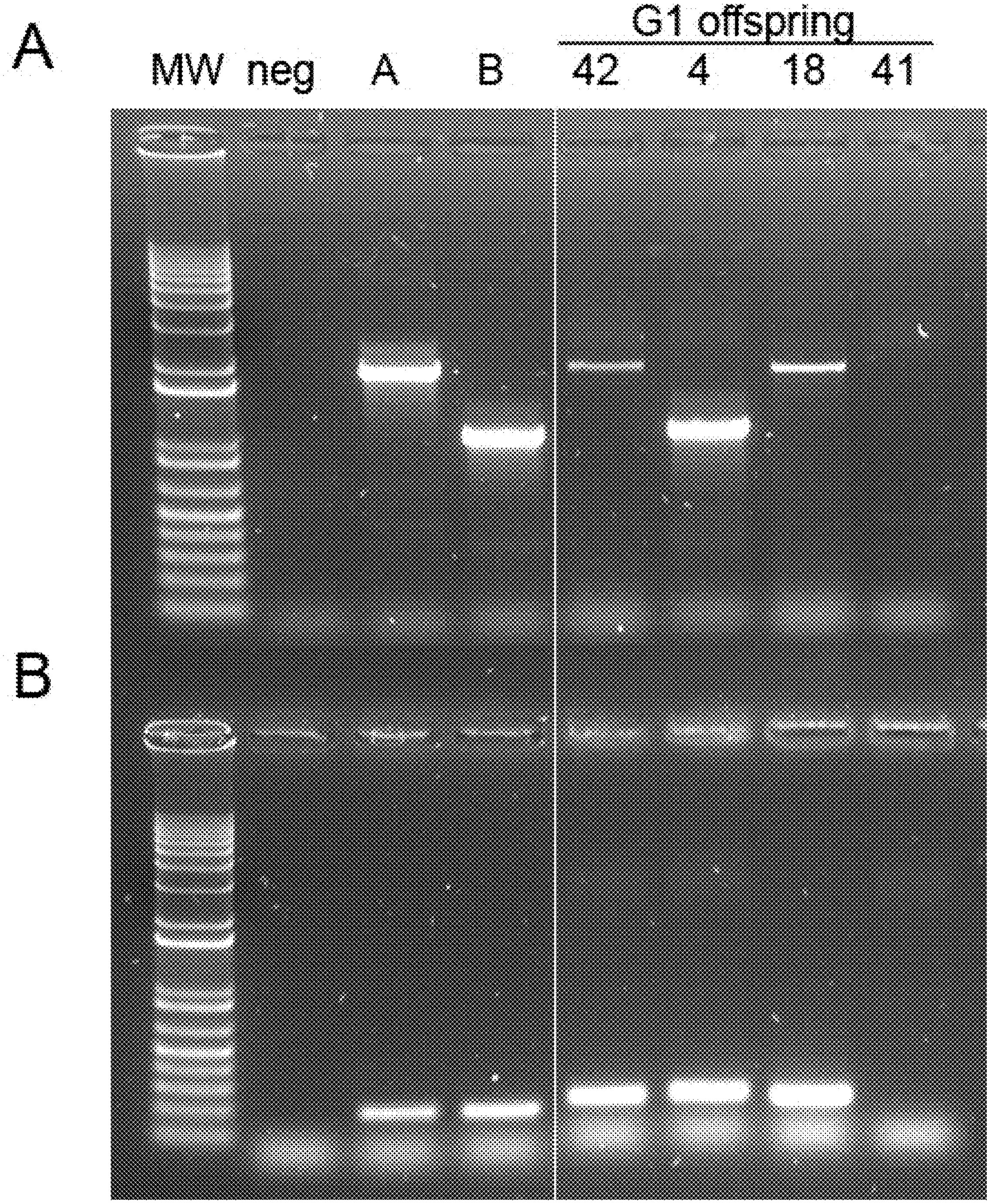

FIG. 8 Seven iCaspase9 and aviCaspase9 targeted G1 offspring

DAZL icaspase9, Dazl aviCaspase9 (chicken) were injected into fertile eggs from DDX4 heterozygote males crossed to female wildtype chicken. 3000 PGCs were injected into windowed stage 16 HH embryos and the eggs were sealed and incubated to hatching. Breeding of these founder chicken has generated seven transgenic G1 offspring containing the targeted transgene. Positive offspring shown here are numbers 42, 4, 18. A. PCR with Caspase9-specific primers; MW, molecular weight markers, A, Targeted PGCs containing aviCaspase9, B, Targeted PGCs containing iCaspase9. B. PCR with primers specific for GFP.

Figure 9:
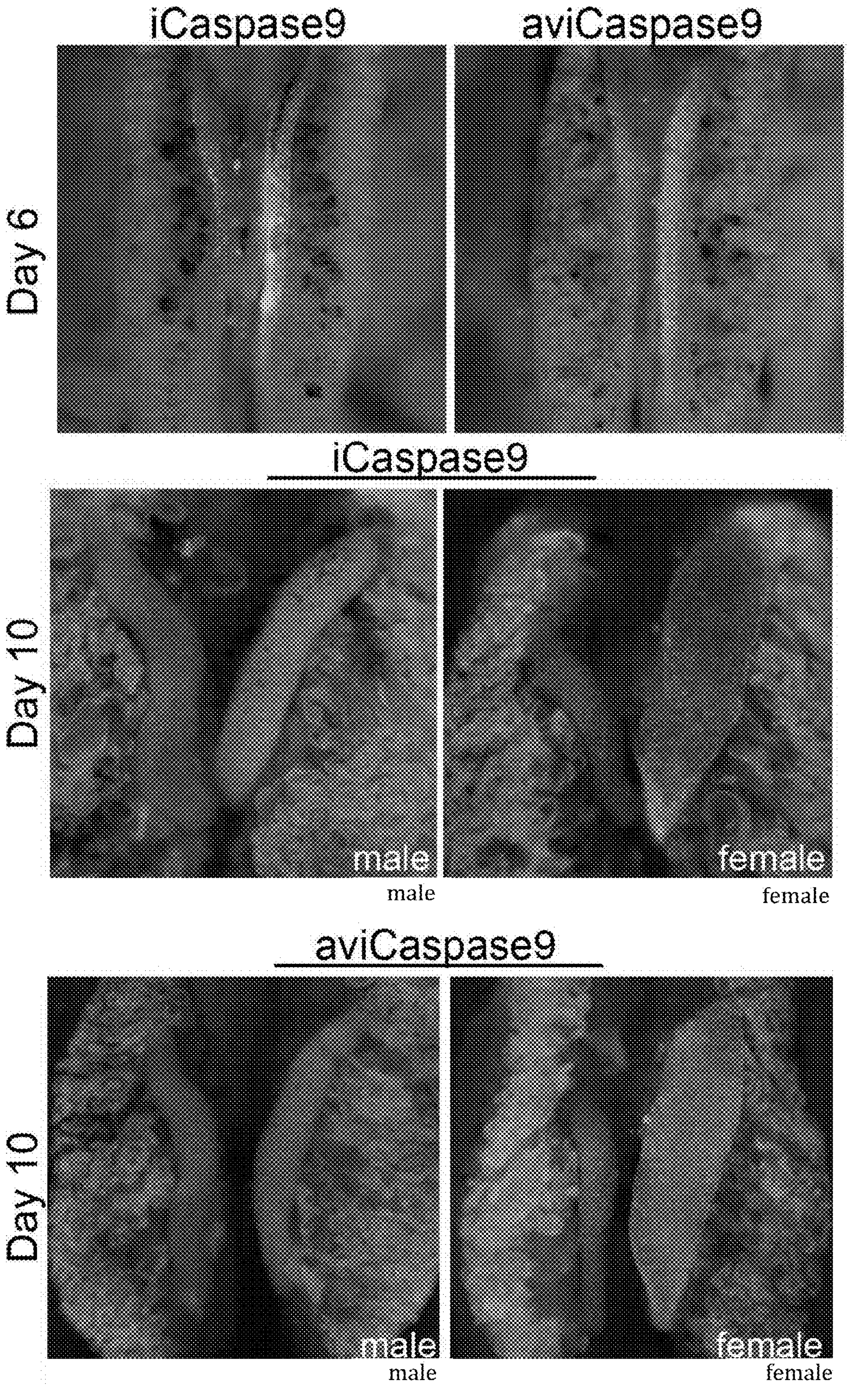
Figure 10A:
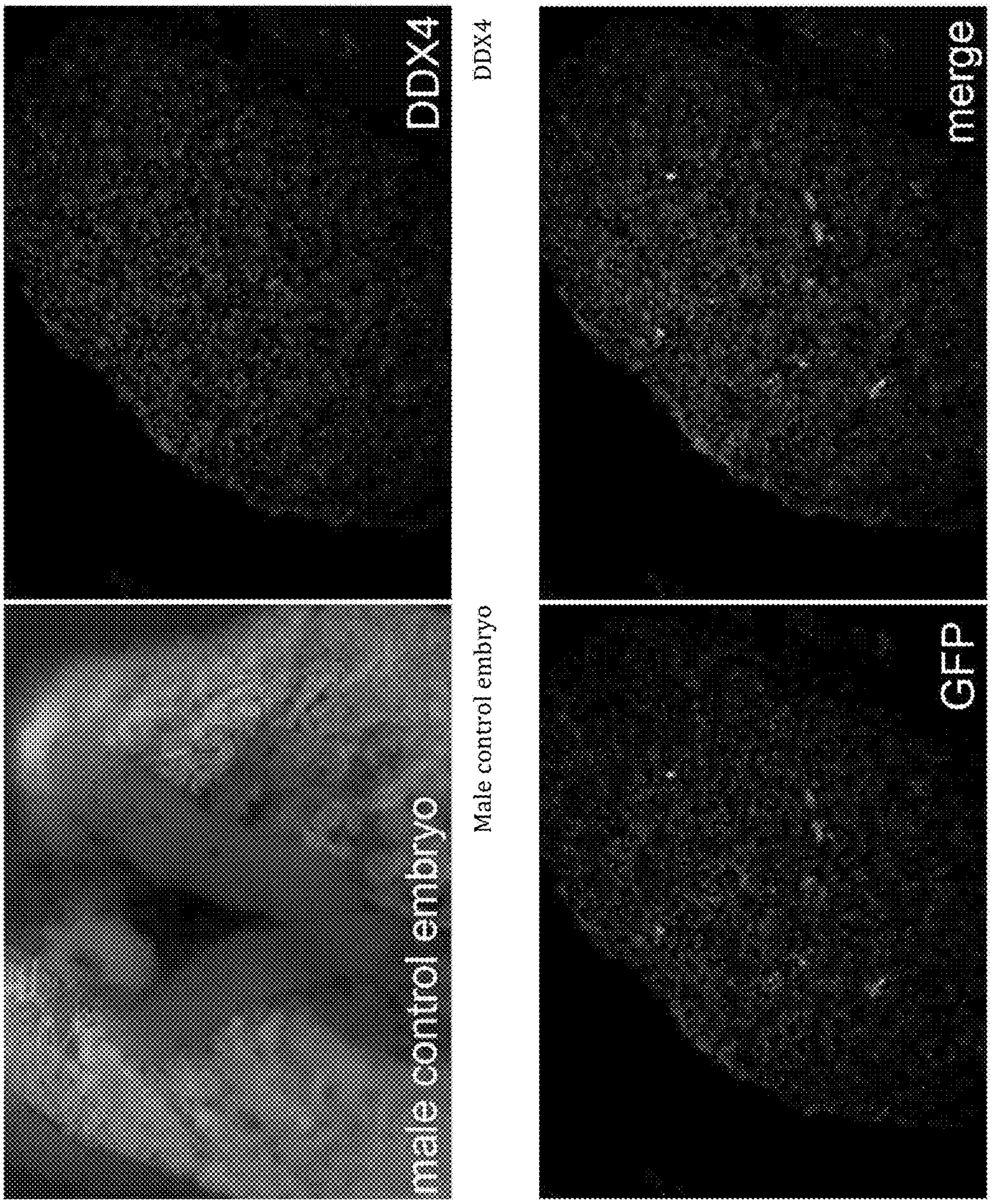
Figure 10B:
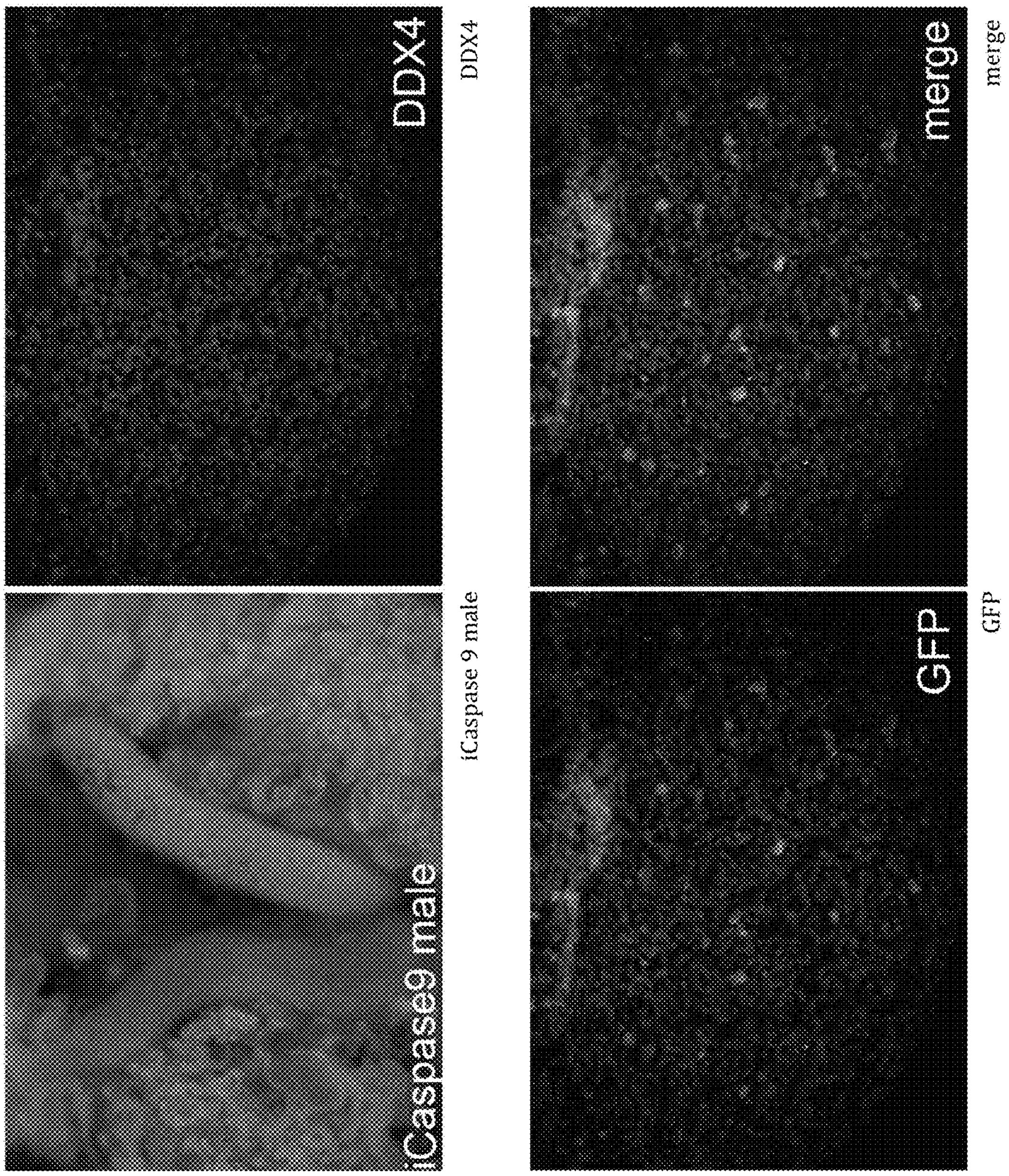
Figure 10C:
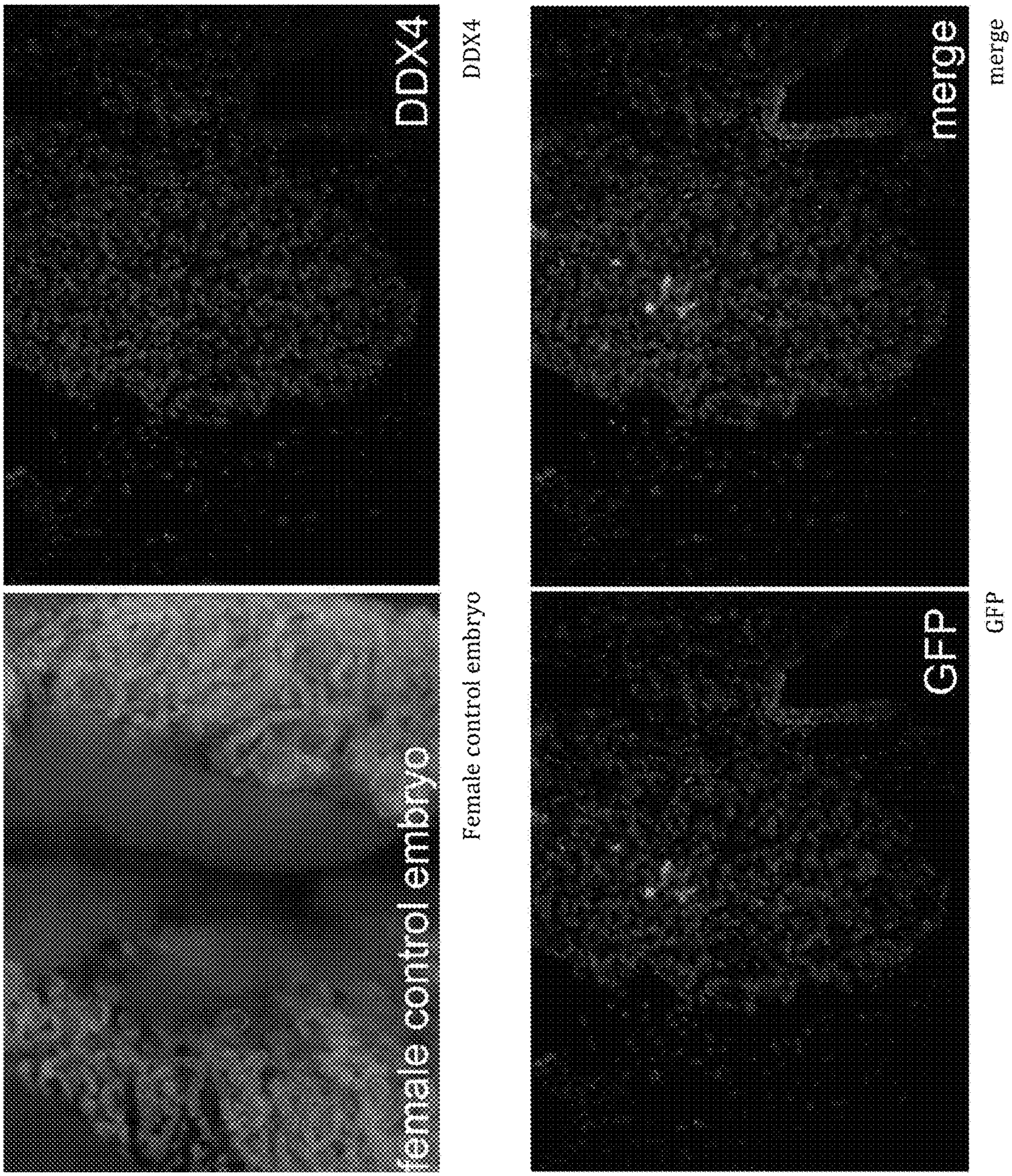
Figure 10D:
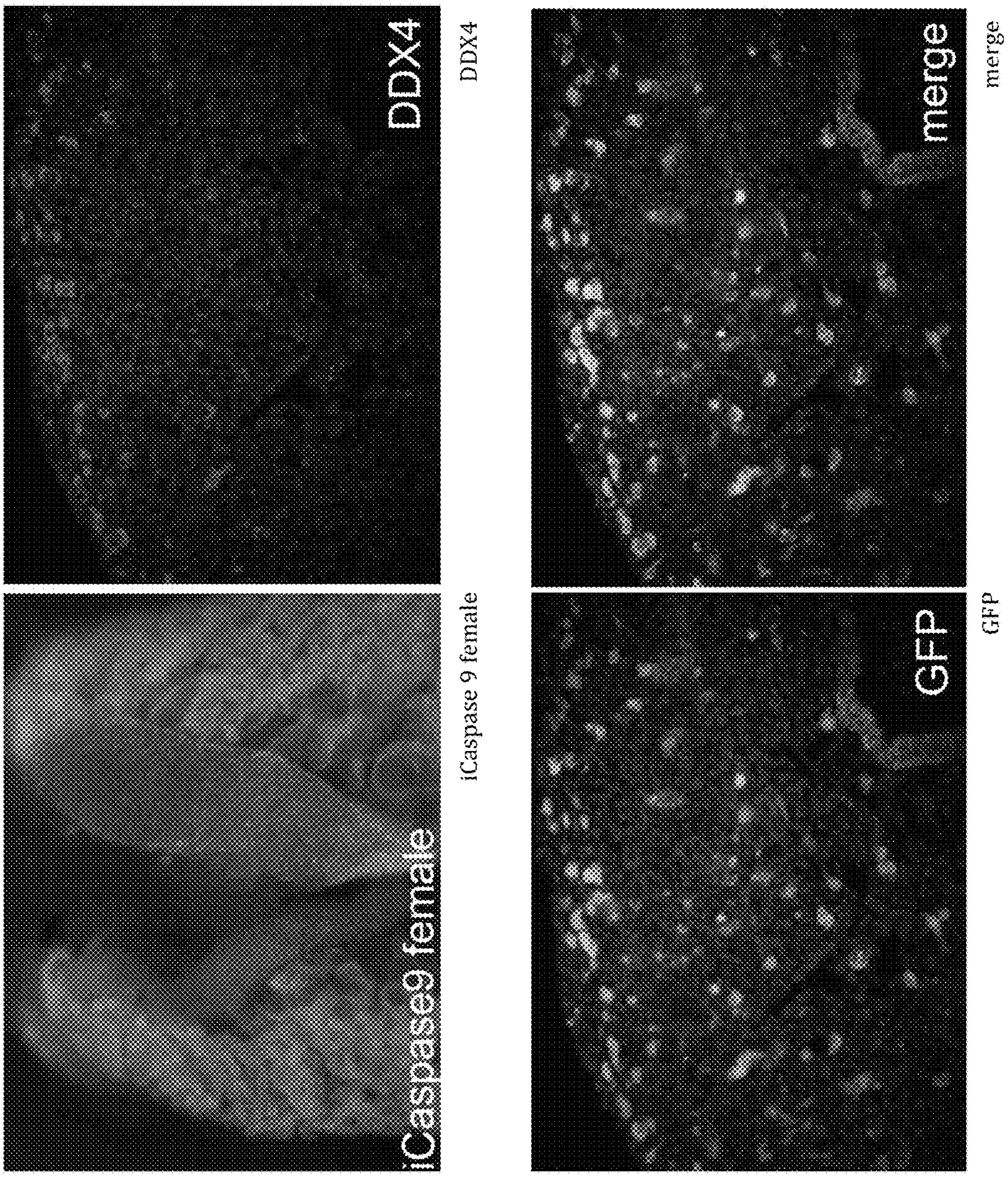
Figure 11A:
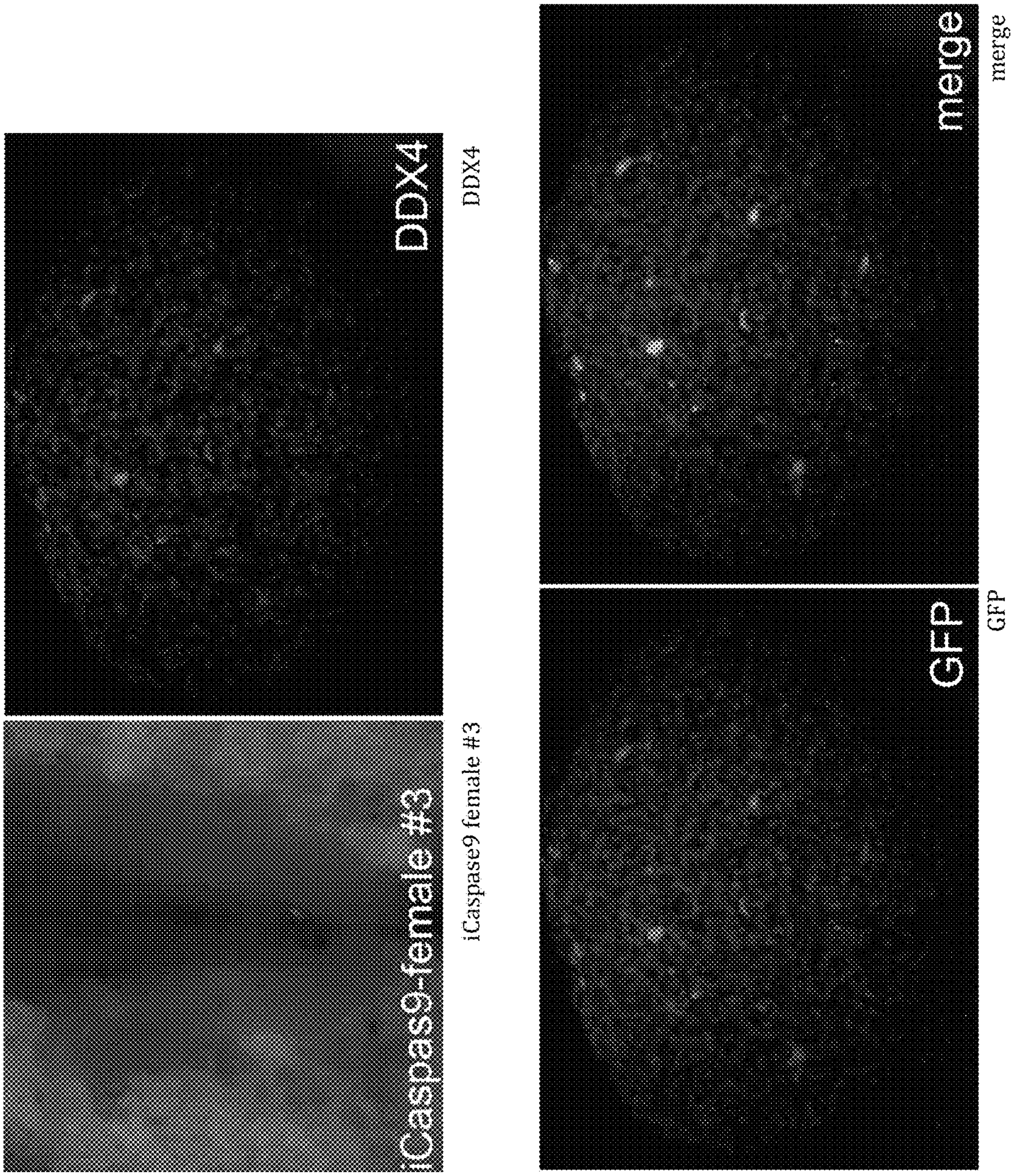
Figure 11B:
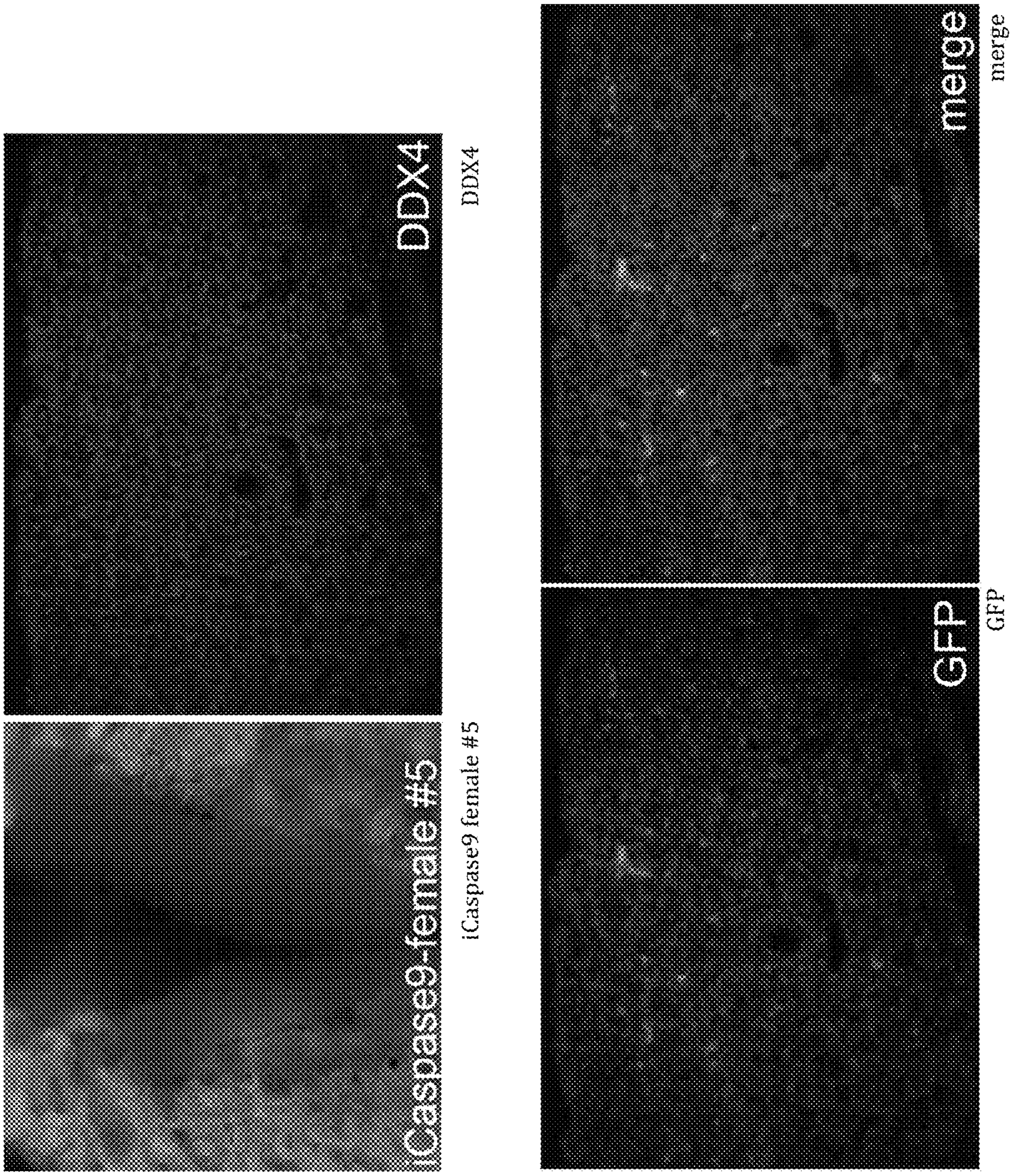
Figure 11C:
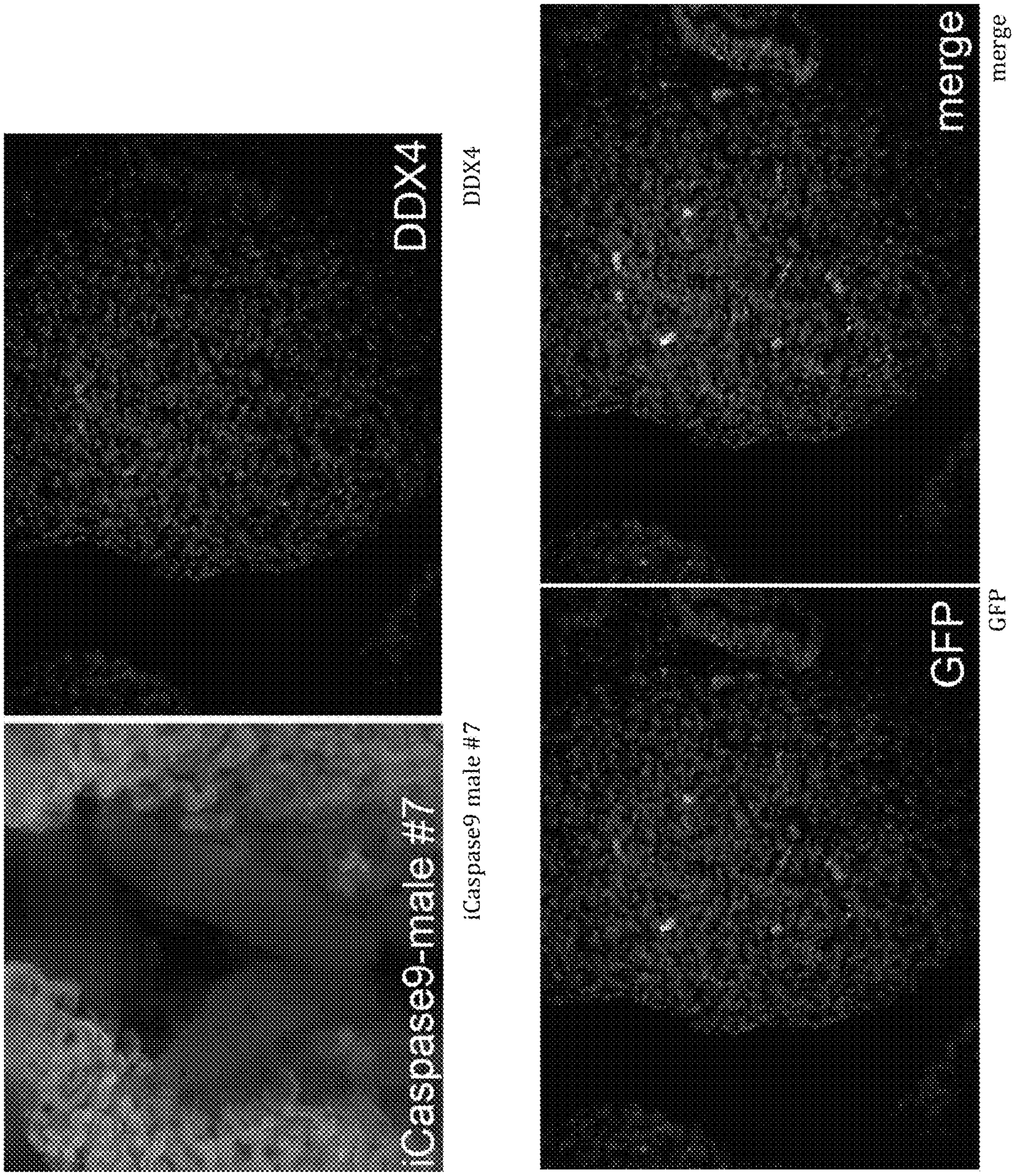
Figure 11D:
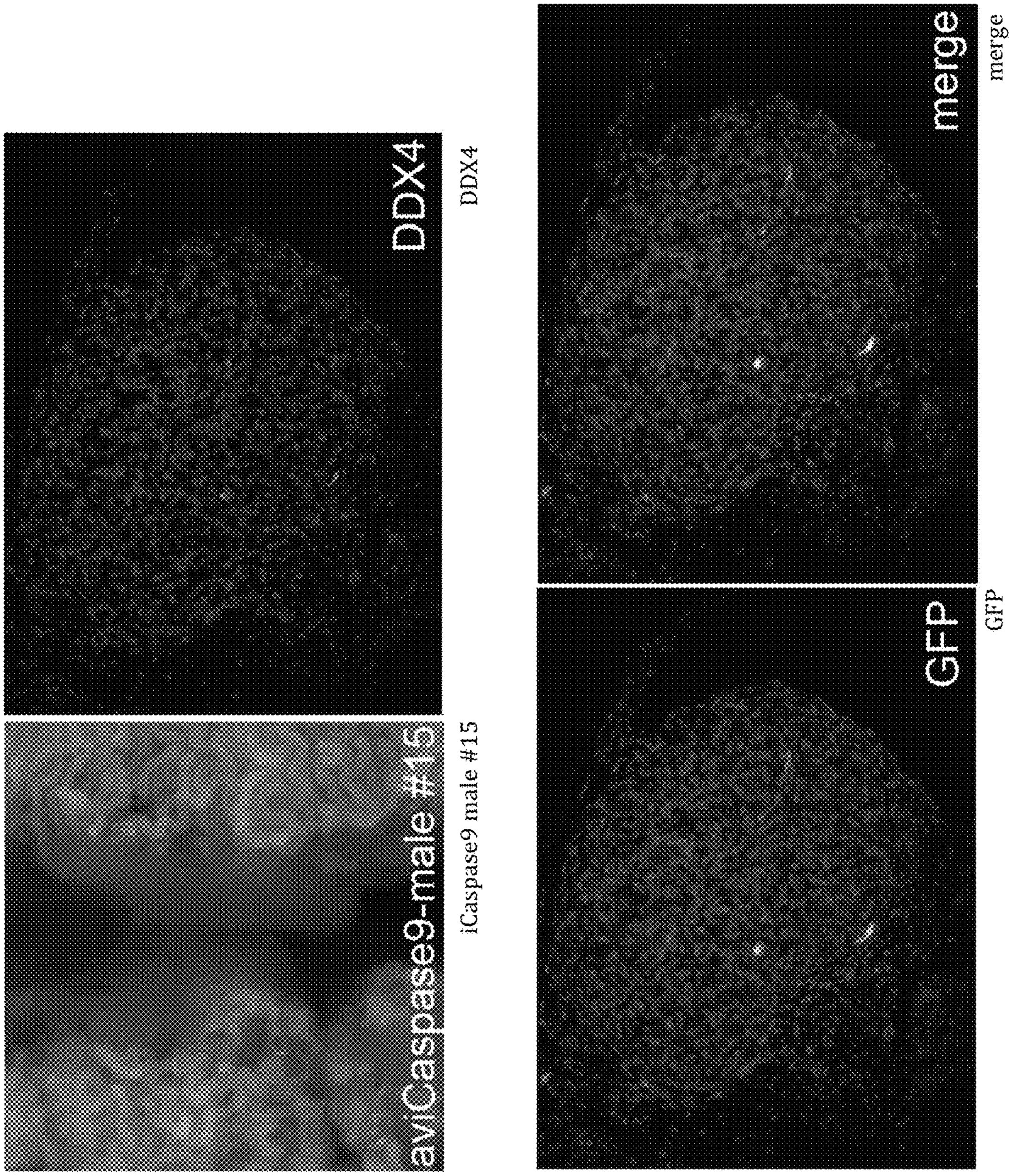
Figure 12A:
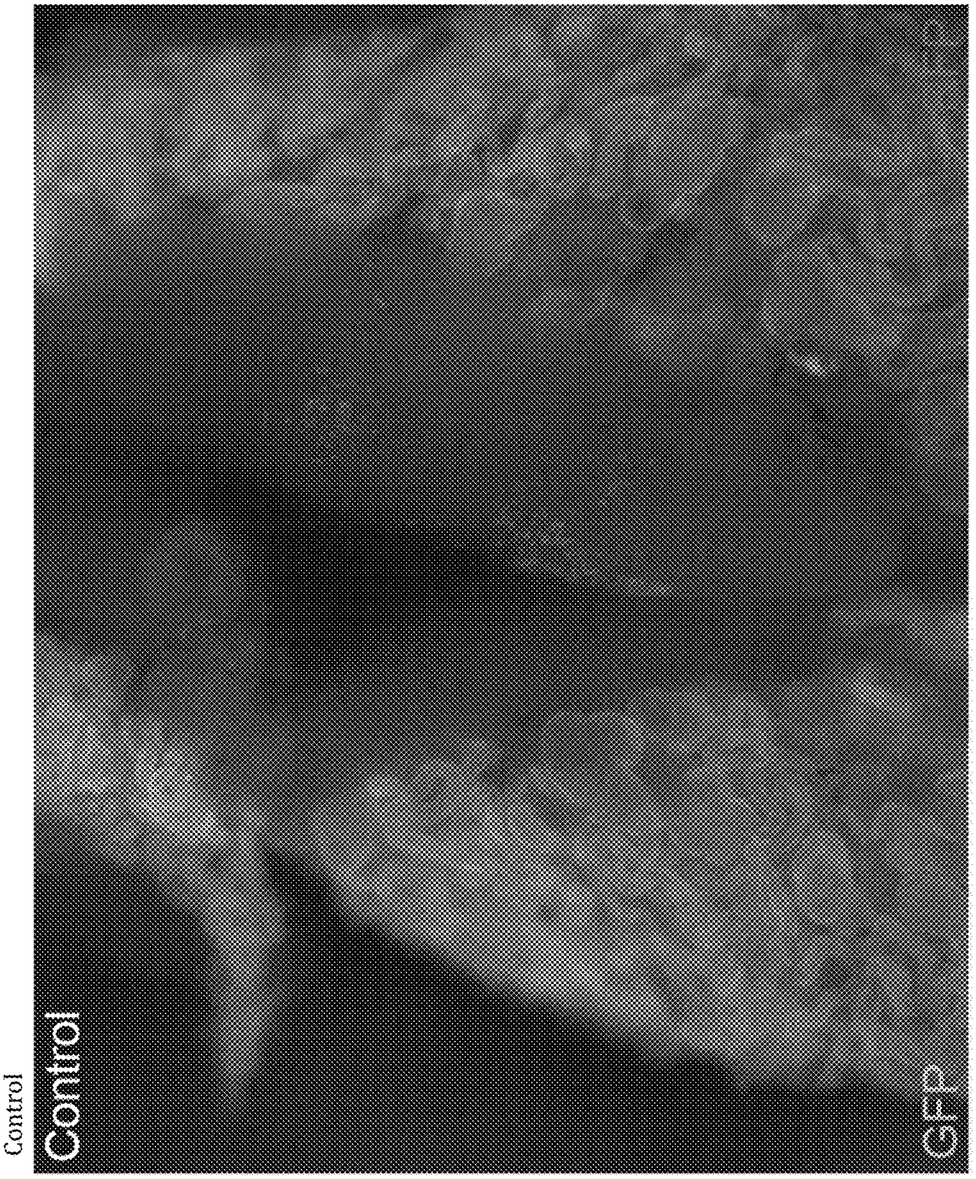
Figure 12B:
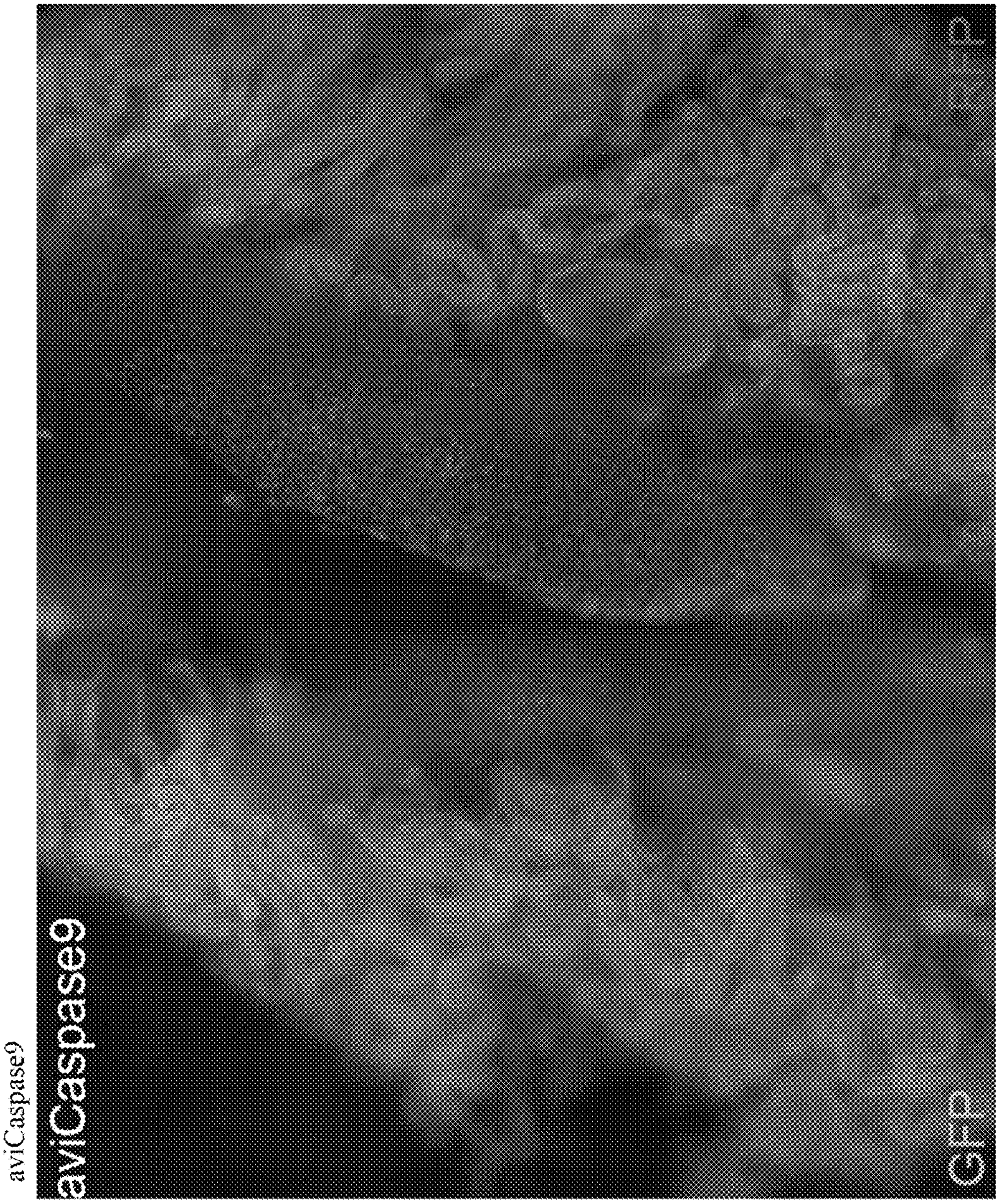
Figure 12C:
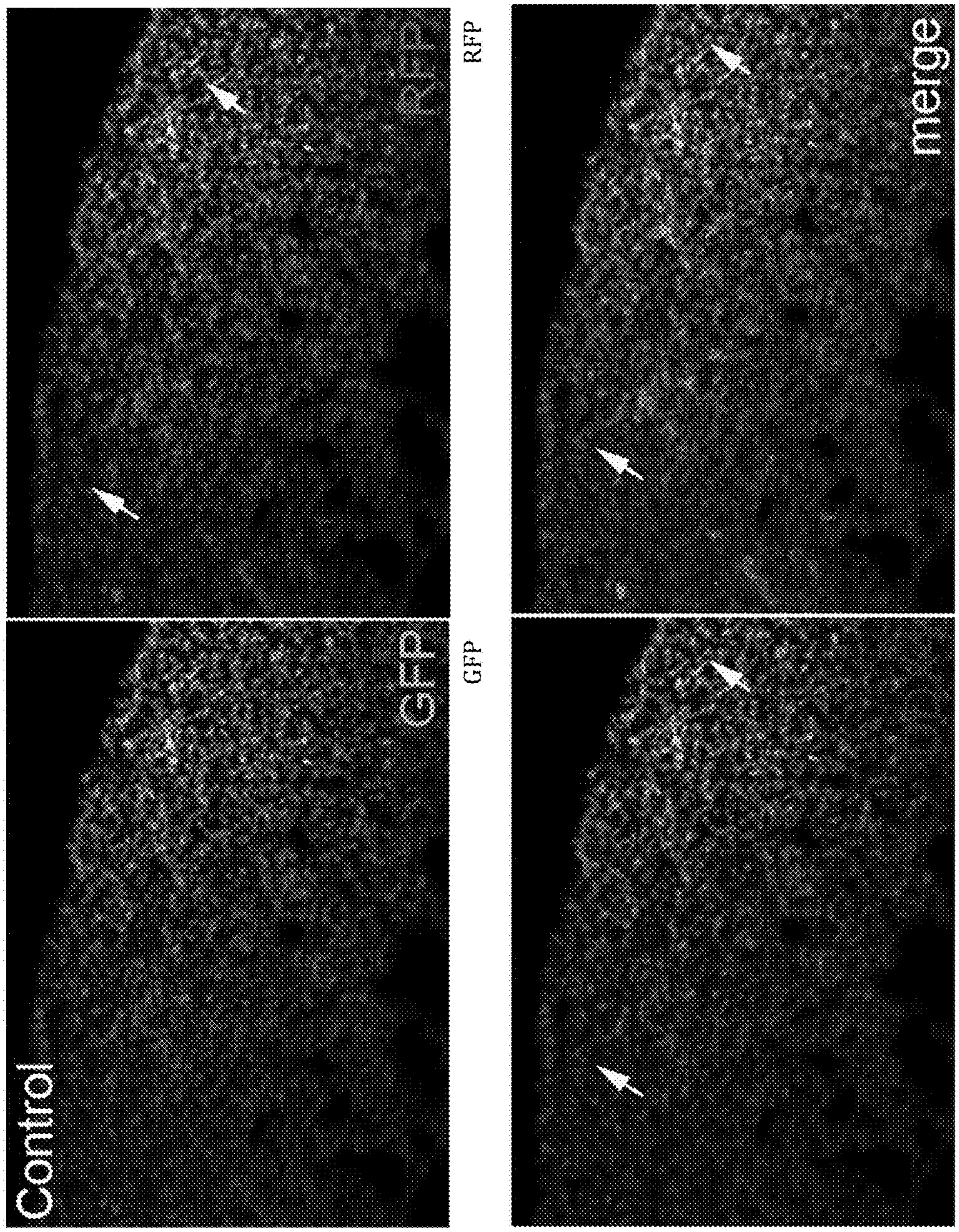
Figure 12D:
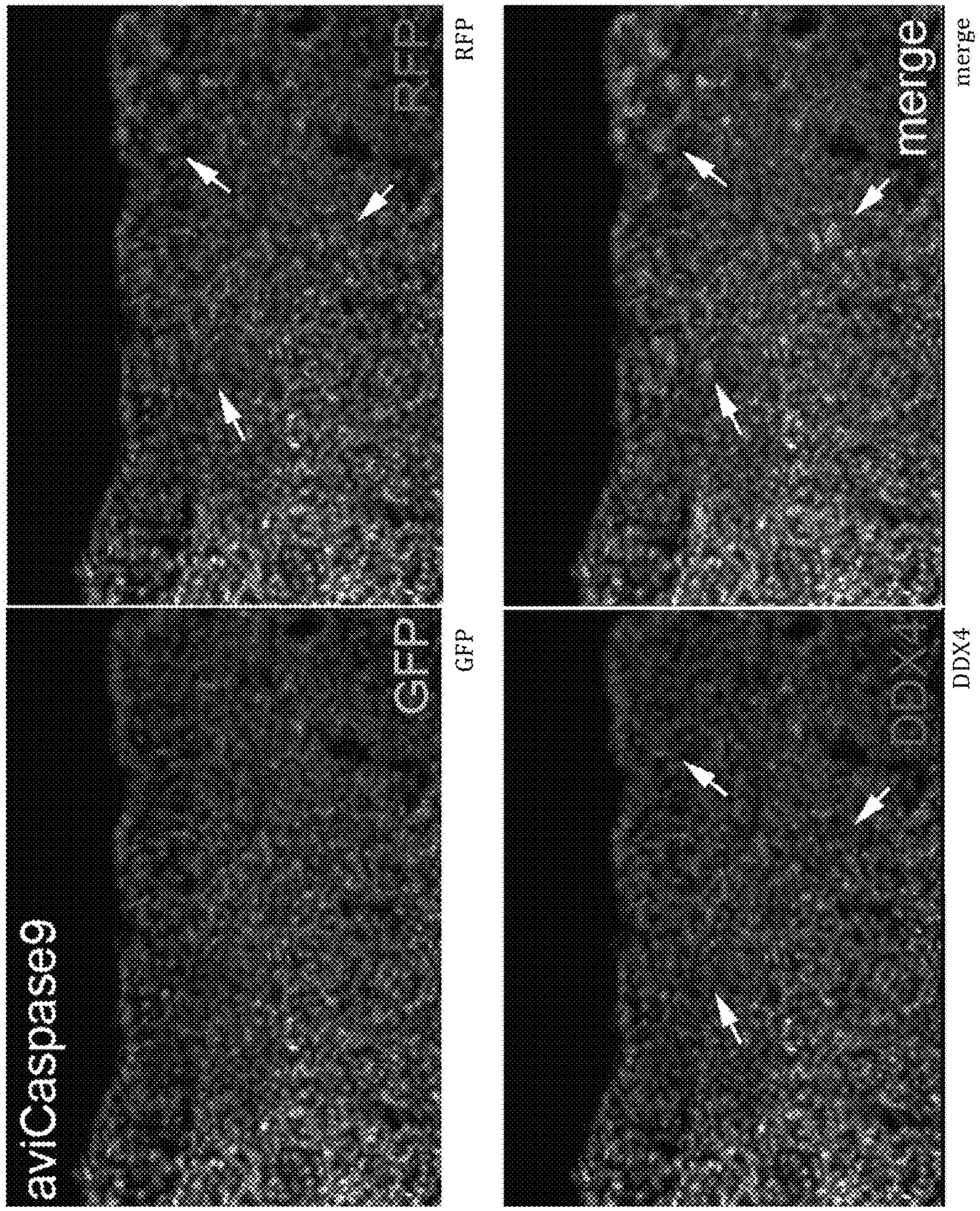

FIG. 9 GFP expression in day 6 and day 10 iCaspas9 and aviCaspase9 G2 embryos.

G2 embryos that PCR positive for the iCaspase9 and aviCaspase9 genes were imaged for GFP fluorescence.

FIG. 10 GFP expression is germ cell specific in day 10 iCaspas9 and aviCaspase9 G2 embryos. Left panels; GFP fluorescence in B/B injected iCaspase9 and aviCaspase9 embryos. Right panels: immunofluorescence for DDX4 protein (red).

FIG. 11 B/B treated iCaspase9 and aviCaspase9 G2 embryos have no germ cells.

B/B was injected into the dorsal aorta of stage 16 chicken embryos (day 2.5). Embryos were incubated and examined at day 10 for GFP fluorescence and DDX4 expression. Left panels; GFP fluorescence in B/B injected iCaspase9 and aviCaspase9 embryos. Right panels: immunofluorescence for DDX4 protein (red).

FIG. 12 B/B drug treatment of aviCaspase9 transgenic embryos ablates host germ cells and permits transplanted donor cells to populate the host gonad. Stage HH 16 embryos containing the aviCaspase9 transgene targeted to the DAZL locus, were injected with 200 donor PGCs transfected with a transposon to insert a cassette for TdTomato expression randomly in the genome. Injected cells were in 1 μl of solution containing 0.5 mM (final concentration) B/B dimerization drug. After injection, eggs were dosed with 50 μl of 1× Pen/Strep containing 15 μM (final concentration) B/B dimeriser drug and incubated for 8 days. At 10 days of development, gonads were dissected and viewed under fluorescence. All germ cells in the aviCaspase9 dimerisation drug treated embryo were from the TdTomato donor cells, no endogenous (host) germ cells were detected.

FIG. 13 DNA synthesised for human iCaspase9 transgene.

FIG. 14 DNA synthesised for chicken iCaspase9 transgene.

FIG. 15 DNA sequence for DDX repair template containing the chicken optimised nitroreductase gene.

FIG. 16 DNA sequence for DAZL repair template containing chicken aviCaspase9.

FIG. 17 DNA sequence for DAZL repair template containing human iCaspase9.

FIG. 18 DNA sequence for DDX4 repair template containing human iCaspase9.

FIG. 19 DNA for chicken optimised nitroreductase gene—The top row of this table states the one-letter amino acid code for each amino acid present in the *E. coli* Ntr and codon optimised Ntr sequences. The second row states the sequence of bases in the *E. coli* Ntr sequence and the third row of the table highlights the changes that have been carried out when optimising the Ntr gene for chicken. The highlighted columns indicate where the three mutations that have been carried out to generate the 3AAS Ntr construct: threonine at codon 41 has been mutated to glutamine (CAG); Asparagine at codon position 71 has been mutated to serine (AGC) and phenylalanine at codon position 124 has been mutated to threonine (ACC).

FIG. 20 illustrates a table of the RNA transcriptome of chicken primordial germ cells compared to other chicken embryonic tissues and pluripotent cells to identify genes that are only expressed in germ cells and at high levels in these embryonic stages. ESC are chicken embryonic stem cells, EGKX are cells from laid egg stage chicken embryos, Non-pluri are a compilation of 66 adult chicken non-pluripotent tissues and cell lines.

FIG. 21 Expression of germ cell-specific genes in avian PGCs. The graph shows the relative gene expression for gem cell-specific genes in chicken, goose and duck PGCs. The average of normalised expression values is obtained from the DESeq2 package. These expression values are normalised to the total number of reads for all samples. The expression of TDRD9 and TUBA1B are recorded higher expression in duck PGCs and GASZ and RNF17 are highly expressed in goose PGCs and remaining genes are expressed higher in chicken PGC.

Figure 22:
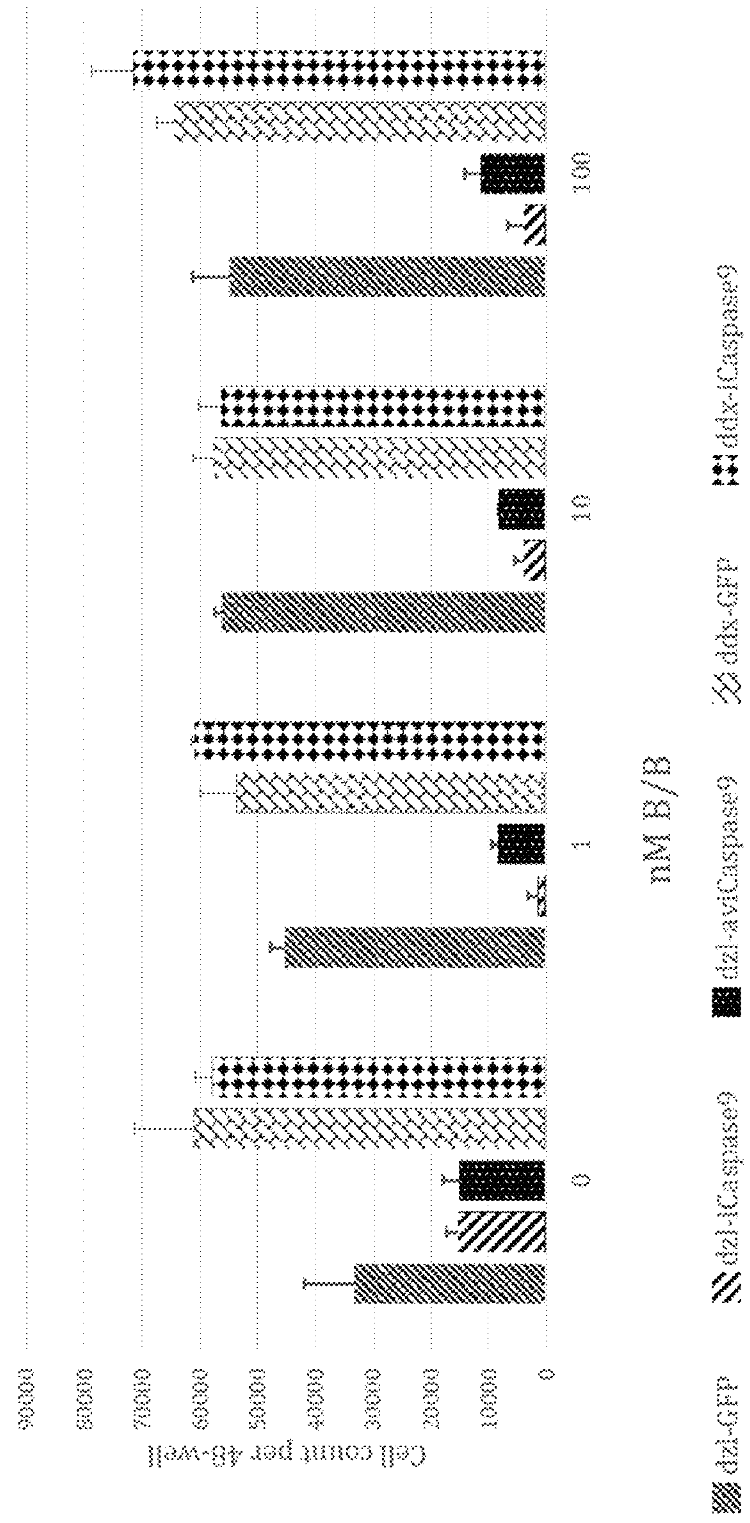

FIG. 22 500 PGCs (dazl-GFP, dazl-iCaspase, dazl-avi-Caspase, ddx4-iCaspase9) were cultured in the presence or absence of the dimerization molecule B/B. After 10 days the total cell number was counted for each well. N=2 for each data point.

FIG. 23 illustrates the use of caspase9 host ablation using black skinned silkie chicken donor PGCs injected into the iCaspase9 surrogate host embyros which are hatched and bred to produce pure offspring. A) The offspring (embryos) from the Dazl-iCaspase9 surrogate did not contain the GFP transgene indicating that most of the host germ cells did not produce offspring (50% of the offspring from the endogenous germ cells should be GFP+ if they were not ablated. Two offspring from the Dazl-aviCaspase9 surrogate contained the GFP transgene indicating that some of the offspring were derived from the endogenous germ cells. (A-C) The offspring (embryos and chicks) have black skins indicating they came from the donor germ cells.

DETAILED DESCRIPTION OF THE INVENTION

The FK-binding protein (FKBP) FKBP12 belongs to the immunophilin family of receptors, and its amino acid sequences are highly conserved between mammals and chicken (Yazawa et al (2003) *Comparative Biochem. Physiol: Mol. Integ. Physiol* 136(2):391-399). It is a cytosolic receptor for the immunosuppressive drug FK506, and is a target for selective control of cell signalling through protein dimerization.

Dimeric FKBP12 variants, FK1012s, have been synthesised by Spencer and colleagues to mediate control of cell signalling through dimerization or oligomerization of intracellular proteins (Spencer et al (1993) Science 262:1019-1024). Later, a specificity binding pocket in FKBP12 was created by substituting the bulky phenylalanine with the smaller valine residue ($FKBP12_{F36V}$). Redesigned FK1012 ligands, including AP1903 and the closely related AP20187, were devised with high affinity and selectivity for $FKBP12_{F36V}$ and minimal interaction with endogenous FKBPs (Clackson et al (1998) *PNAS* 95(18):10437-10442; Nör et al (2002) *Gene Ther* 9(7):444-51).

Caspase proteins, 2, 3, 4, 7, 8, 9 or 10 are naturally occurring proteins which are known to induce programmed cell death. Caspase 9 (Casp9) activates upon dimerization and results in cellular apoptosis. Casp9 can be truncated to remove its dimerization domain (CARD). By fusing $FKBP12_{F36V}$ dimerization domain to Casp9, cell ablation can be selectively induced upon ligand introduction. This system is called the inducible caspase9 (iCas9 (iC9)) system. AP20187 is marketed as B/B homodimerizer drug. This has been utilised to provide a system to induce cell ablation. The fusion protein has been used to eliminate cells in vitro (Carlotti et al (2005) *Cancer Gene Ther* 12(7):627-39). It also has been used to eliminate cells in vivo in mice, Xenopus, and Zebrafish (Mallet et al (2002) *Nat Biotechnol* 20(12):1234-1239; Pajvani et al (2005) *Nat Med* 11(7):797-803; Hamm et al (2009) Invest *Ophthalmol Vis Sci* 50(2):885-92; Weber et al (2016) *Development* 143(22):4279-4287; Shimokawa (2017) *Nature* 11; 545(7653):187-192).

EXAMPLE 1

Selective Ablation of Chicken Primordial Germ Cells (PGCs) Through Modification of the Chicken Genome with an Inducible-Caspase 9 (iC9) Transgene.

Preparation of DNA Constructs Used to Produce iCasp9-Transfected PGCs

To express inducible Casp9 specifically in PGCs, CRISPR/Cas9 gene editing was used to mediate a sequence insertion in the following loci that are specifically expressed in PGCs:

DDX4: Chicken vasa homolog, an RNA helicase, is expressed specifically in germ cells by the DDX4 locus. Targeted insertion of exogenous genes at the DDX4 start codon (ATG), was undertaken to achieve germ-cell specific expression of the corresponding proteins.

DAZL: The DAZL locus drives expression of the RNA-binding protein DAZL. DAZL expression is also germ-cell specific, and has been measured as at least 10-fold higher than DDX4 expression (Jean et al. 2014). Targeted insertion of exogenous cDNAs at the stop codon (TGA) of the DAZL locus was used to achieve germ-cell specific expression of the corresponding proteins.

A diagram of the targeting strategy is shown in FIG. 2 and FIG. 3.

Inducible Caspase 9

The plasmid pMSCV-F-del Casp9.IRES.GFP (https://www.addgene.org/15567/), deposited by the Spencer lab (Straathof et al (2005) *Blood* 105(11):4247-54), contains the cDNA sequence for $FKBP12_{F36V}$ fused to truncated human Casp9 (truncated such that its dimerization domain has been removed to lower basal activity), with an HA tag fused to the C-terminus of Casp9. This DNA sequence is referred to hereon as iCasp9.

The iCasp9 sequence was chemically synthesised with a proceeding P2A sequence, with flanking BamH1 restriction sites, and with a within-sequence BamH1 site removed by codon-swapping. The BamH1-site-flanked iCasp9 sequence (human_iCasp9) was synthesised in a pMA vector.

In addition, the Casp9 domain of human-iCasp9 (amino acids 135-417 of NP_001220.2) was exchanged for the homologous amino acid region for the chicken Casp9 protein sequence (amino acid 169-450 of XP_424580.6) to produce chicken_iCasp9 sequence. The chicken iCasp9 sequence was chemically synthesised with a preceding P2A sequence, with flanking BamH1 restriction sites, and with a within-sequence BamH1 site removed by codon-swapping.

The BamH1-site-flanked iCasp9 sequence (chicken_iCasp9) was synthesised in a pMA vector. This DNA sequence is referred to herein as aviCasp9.

Nitroreductase Transgene

Nitroreductase gene is present in certain bacterial species and reduces the nitro group of certain chemical compounds to cytotoxic metabolites. The nitroreductase gene from *E. coli* was codon optimised for chicken expression. Three amino acid substitutions were made which were shown to produce higher specific activity (see FIG. 19) in the presence of prodrug substrate CB1954.

DDX4-GFP Repair Template

The DDX4 repair template was initially constructed using Gibson cloning, which allows ligation of multiple overlapping double-stranded DNA fragments. The fragments for this plasmid were prepared by PCR (Invitrogen primers), or by restriction digest (NEB enzymes). 2A ribosomal skip sequences were included between genes to avoid translation of fusion proteins. These 2A peptides were designed with GSG linkers at their amino terminus, the sequence for which includes a BamH1 restriction cut site to allow insertion of additional 2A-linked genes.

The main fragment was prepared using sequence from the pGEM-T (Promega) vector, which contains ampicillin resistance and multiple cloning site (MCS) cassettes. The 3 kbp pGEM-T sequence, along with 3 kbp of homology up to the start codon of DDX4 (left targeting arm), was obtained from a previously constructed DDX4 targeting vector (HOMOL pGEM-T leftarm and right arm ddx4+GFPpuropolyA), using Xcm 1 and Nco1 to cut out the 6 kbp fragment, which was cleaned up using gel purification.

A right targeting arm consisting of 1.5 kbp of homology from the DDX4 start codon was synthesised by PCR using genomic DNA prepared from chicken PGCs (Y2 cells, derived from eggs obtained from NARF). The forward primer for this reaction (CGGTGACGTCGAGGAGAATCCTGGACCTATGGAGGAGGATTGGGATACCGAACTCGA GCAGGAGGCGGCAGCGGC, 75 bp) SEQ ID NO: 7 contained partial sequence for the T2A ribosomal skip and codon swaps at the CRISPR/Cas9 targeting site, so that the repair template would not be cut by Cas9 protein. The reverse primer for this reaction (GAAATCCAGCTTCCAGTTCCCACCTGGCCAGACAAGGGGCTGCTTGG, 47 bp) SEQ ID NO: 8 contained a 20 bp overhang to the pGEM-T vector sequence, along with nucleotides which reinserted the Xcm1 cut site after the overhang.

The final fragment (800 bp) for the DDX4 repair template contained sequence for eGFP, which was again synthesised by PCR from the previously constructed DDX4 targeting vector, HOMOL pGEM-T leftarm and right arm ddx4+GFPpuropolyA. The forward primer (GGTGGGCTGCTGGCATTCGCCATGGTGAGCAAGGGCGAGGA, 41 bp) SEQ ID NO: 9 for this reaction contained a 20 bp overhang to the left targeting arm along with nucleotides which reinserted the Nco1 cut site after the overhang. The reverse primer for this reaction (GATTCTCCTCGACGTCACCGCATGTTAGCAGACTTCCTCTGCCCTCTCCGGATCCCTT GTACAGCTCGTCCATGCC, 76 bp) SEQ ID NO: 10 contained the remaining T2A sequence plus 20 bp of overhang for the partial T2A sequence in the right arm fragment.

To ligate the fragments, a mix of 100 ng of the main fragment, along with equimolar quantities of the other fragments, were incubated with the Gibson HiFi DNA Assembly Master Mix enzyme (NEB) for 1 hour at 50° C. XL-10 Gold competent cells were transformed with 2 μl of ligated plasmid. Mini-preps prepared from transformed cells were verified by restriction digest, and a maxi-prep was prepared.

The DAZL repair template was initially constructed using Gibson cloning, with fragments for the plasmid prepared by PCR (IDT primers), or by restriction digest (NEB enzymes). IDT can synthesise primers >100 bp in length, which were necessary for this work. The repair template was also constructed to include the chicken optimised NTR gene, the product of which can be used to selectively ablate cells upon introduction of a prodrug.

The main fragment for the targeting template was the 3 kbp pGEM-T sequence, which was obtained from the DDX4-GFP repair template described above, using Xcm1 and Not1 to cut out the DNA.

A left targeting arm consisting of 1.5 kbp of homology up to (but not including) the DAZL stop codon was synthesised by PCR using genomic DNA prepared from chicken PGCs (Y2 cells). The forward primer for this reaction (TCTCCCATATGGTCGACCTGCAGGCGGCCGCGAATTCACTAGTGATTCTTCGTGGTT, 67 bp) SEQ ID NO: 11 contained a 25 bp overhang to the pGEM-T vector sequence, along with nucleotides which reinserted the Not1 cut site after the overhang. The reverse primer for this reaction (AGGCTGAAGTTAGTAGCTCCGGATCCAACACTTTTGAGCACTGCTCTT, 48 bp) SEQ ID NO: 12 contained a 25 bp overhang to the P2A ribosomal skip sequence.

The third fragment (600 bp) contained sequence for P2A, followed by NTR, which was cut using BamH1 from the DDX4-GFP-NTR repair template, which in turn had been constructed using the DDX4-GFP repair template (linearised with BamH1 and ligated with an insert contained the P2A-NTR sequence).

The fourth fragment (800 bp) contained sequence for eGFP, which was synthesised by PCR from the DDX4-GFP repair template. The forward primer (CAGAACATCACCCTGACCGAGGTGGGATCCGGAGAGGGCAGAGGAAGTCTGCTAACA TGCGGTGACGTCGAGGAGAATCCTGGACCTATGGTGAGCAAGGGCGAGGA, 107 bp) SEQ ID NO: 13 for this reaction contained a 25 bp overhang to the NTR gene and sequence for the T2A ribosomal skip. The reverse primer for this reaction (CTTGTACAGCTCGTCCATGCCG, 22 bp) SEQ ID NO: 14 contained no overhangs.

The fifth and final fragment for the DAZL-GFP targeting template was a right targeting arm consisting of 1.5 kbp of homology from (and including) the DAZL stop codon, synthesised by PCR using genomic DNA prepared from chicken PGCs (Y2 cells). The forward primer for this reaction (TCTCGGCATGGACGAGCTGTACAAGTGATGAACAAAGACTTTGAAGTACATAAATGTAT TACTTTGATGTTAATACAGTTCAGTTTAGTAAGAT, 94 bp) SEQ ID NO: 15 contained a 25 bp overhang into the eGFP gene and mutations at the PAM site for the corresponding CRISPR/Cas9 plasmid. The reverse primer for this reaction (CTCTTCGAAATCCAGCTTCCAGTTCCCACCTGGCAATACTATTAAAGCAATAGGT, 55 bp) SEQ ID NO: 16 contained a 25 bp overhang into the pGEM-T vector sequence, along with nucleotides which reinserted the Xcm1 cut site after the overhang.

To ligate the fragments, a mix of 100 ng of the main fragment, along with equimolar quantities of the other fragments, were incubated with the Gibson HiFi DNA Assembly Master Mix enzyme (NEB) for 2 hours at 50° C. XL-10 Gold competent cells were transformed with 2 μl of ligated plasmid. Mini-preps prepared from transformed cells were verified by restriction digest, and a maxi-prep was prepared.

BamH1 was used to cut out the chicken optimised NTR sequence from the DAZL-GFP repair template. The human and chicken 2A-iCasp9 sequences (iCasp9 and aviCasp9) were cut using BamH1 from their respective pMA vectors and inserted into the open DAZL-GFP repair template by T7 ligation. XL-10 Gold competent cells were transformed with 2 μl of ligated plasmid. Mini-preps prepared from transformed cells were verified by restriction digest, and a maxi-prep was prepared for the DAZL-aviCasp9-GFP (chicken) repair template and the DAZL-iCasp9-GFP (human) repair template.

Guide RNA (gRNA) sequences within 150 bp of the DAZL locus stop codon were queried using the CRISPR design tool available on crispr.mit.edu. Forward and reverse oligos (IDT) for the top 5 scoring guides (with the first two bases of the guide sequence replaced with GG) were synthesised with Bbs1 sticky ends. The oligos were annealed by PCR, and ligated into pSpCas9(BB)-2A-Puro (PX459) V2.0 (https://www.addgene.org/62988/), using a digestion/ligation PCR mix. Competent cells were transformed with 2 μl of ligated plasmid, and maxi-preps were prepared from transformed colonies. The DAZL-PX459 maxi-prep plasmids (#1-5) were verified by PCR, using the forward oligo and a reverse primer complimentary to the PX459 plasmid 400 bp downstream from the guide insertion cut site (Bpi1). All DNA Sequences are Shown in FIGS. 13-19.

Transfection Process

Approximately 150,000 PGCs were transfected with 1 μg of DAZL-iCasp9-GFP repair template (either chicken or human) and 1 μg of either DAZL-PX459-4 or -5, using Lipofectamine 3000. After 5 hours in Lipofectamine solution, PGCs were pelleted and resuspended in complete (FAOT) media. 24 hours later, PGCs were given fresh media and 2 μl of a 0.1 mg/ml solution of puromycin was added to each well (final concentration 0.04 μg/ml). PGCs were incubated with puromycin for 48 hours, washed once, and resuspended in fresh media. Cells were cultured 1-2 weeks to reach a population of 200,000-400,000 cells, and then sorted using FACS to collected successfully modified (GFP-positive) cells. GFP-positive cells were obtained from PGCs transfected with either DAZL-PX459-4or DAZL-PX459-5, though only PGCs transfected with DAZL-PX459-5 were used for making chickens.

DAZL-PX459-4, contains the following guide sequence: GGTCCTATTCCAGGAGAGGA SEQ ID NO: 17. The PAM site for this guide is on the forward strand of the genome, 44 bp upstream of the DAZL locus stop codon.

DAZL-PX459-5, contains as its guide sequence: GGCTTACTAAACTGAACTGT SEQ ID NO: 18. The PAM site for this guide is on the reverse strand of the genome, 46 bp downstream of the DAZL locus stop codon. While the PAM site sequence for the guide in DAZL-PX459-5 was mutated in the homology arm of the final DAZL-iCasp9-GFP repair template, it should be noted that the PAM site sequence for the guide in DAZL-PX459-4 was not mutated.

PGCs were cultured for three weeks to select for cells that were stably targeted with the GFP expressing constructs. Female PGCs targeted with ddx4_GFP and dazl_GFP were purified by flow cytometry by using a FACS-ARIA gated for GFP florescence. The purified cells were expanded in number in culture analysed by flow cytometry to quantify the level of GFP fluorescence. The cells with GFP targeted to the DAZL locus were 3.75× more fluorescent than the cells with GFP targeted to the DDX4 locus (FIG. 4).

Female PGCs targeted with DDX-Ntr, DDX-icaspase9, DAZL-Ntr, DAZL-icaspase9 (human), Dazl-icaspase9 (chicken) were purified in a similar manner.

PGCs containing the targeted nitroreductase gene were treated with the pro-drug CB1954. PGCs died when exposed to the drug. Cells containing NTR targeted to the dazl locus had a reduction in cell number in comparison to the control cells (FIG. 5).

PGCs containing the targeted icaspase9 gene were treated with the B/B dimerization compound. Control untargeted PGCs did not have reduced numbers of PGCs when treated with the drug. Cells containing the human and chicken caspase9 genes targeted to the dazl locus had severely reduced PGC numbers (FIG. 6). Cells containing iCaspase 9 targeted to the ddx4 locus had slightly less PGC number. These cells were mixed with control red fluorescent PGCs and injected into chicken embryos. The chicken embryos were treated with the B/B dimerization compound. Only red PGCs and control GFP PGCs were visible in the embryos. Dazl icaspase9 PGCs were killed (FIG. 7).

Production of Dazi icaspase9 Targeted Chicken

Dazl iCaspase9 (human) or Dazl aviCaspase9 (chicken) or both mixed together were injected into fertile eggs from DDX4 heterozygote ($Z^{-}Z$) males crossed to female wildtype chicken. 3000 PGCs were injected into windowed stage 16 HH embryos and the eggs were sealed and incubated to hatching. Breeding of the founder ($Z^{-}W$) female hatched chickens generated transgenic offspring containing the targeted transgene (FIG. 8).

Analysis of Dazl-iCaspase9 and Dazl-aviCaspase9 Targeted Chicken and Germ Cell Ablation Using BIB Dimerization Reagent The G1 Dazl-icaspase9 and Dazl-aviCaspase9 chickens were raised to sexual maturity and mated with wildtype chickens. Fertile eggs from the matings (G2 embryos) were incubated and examined for GFP expression in the gonads. The germ cells in the gonads of both Dazl-icaspase9 and Dazl-avicaspase9 G2 embryos contained GFP+ cells in the gonad (FIG. 9). Cryosections and immuno-staining with an antibody to the germ cell marker, DDX4, showed that the GFP-expressing cells are germ cells (FIG. 10). The G2 embryos were tested for germ cell ablation. 1.0 μl of 0.1 mM B/B dimerization reagent (Takara Bio, Inc) was injected into the bloodstream of day 2.5 (stage 16 Hamilton & Hamburger (HH)) chicken embryos. The embryos were incubated for 8 days, PCR-screened to identify iCaspase9 embryos and examined for GFP expression in the gonads. Drug treated G2 Dazl-iCaspase9 and Dazl-aviCaspase9 embryos have no visible GFP expression (FIG. 11). Cryosections and immuno-staining with an antibody to the germ cell marker, DDX4, shows that almost no identifiable DDX4 positive or GFP+ cells are present in the gonads of Dazl-icaspase9 and Dazl-aviCaspase9 embryos (FIG. 11). To show that exogenous (donor) PGCs can colonise the sterilised host Dazl-aviCaspase9 G2 embryos were injected with donor red fluorescent germ cells and B/B drug. Embryos were incubated for 8 days and examined for florescence and germ cells. The aviCaspase9 G2 embryo only had donor germ cells present in the gonad, no endogenous (host) germ cells were detected. (FIG. 12).

Ablation of Germ Cells in Transgenic Chicken

The iCaspase9 trasgene was targeted to either the DDX4 or the DAZL locus in PGCs and the cells were then exposed to the dimerisation drug. Cells containing the transgene inserted at the DAZL locus were determined to be inhibited/killed. Without wishing to be bound by theory, the inventors consider the expression levels at embryonic stages are important for ablating germ cells.

This detail is illustrated in FIG. 22.

Utilising caspase 9 expression targeted to the DAZL locus in PGCs, host germ cell ablation and producing offspring from a donor chicken breed were tested using chicken donor PGCs from a black skinned silkie chicken breed. Donor PGCs injected into the caspase host embryos which were then raised to sexual maturity and bred were tested. As indicated in FIG. 23, the offspring from Dazl-Caspase9 hosts injected with Silkie PGCs and treated with B/B drug were found to have black skin indicating they came from the donor germ cells.

In more detail, in this embodiment, black skinned Silkie PGCs were mixed with B/B dimerisation drug and injected into Dazl-Caspase host embryos whilst in the egg. The eggs were sealed and the embryos were hatched then crossed to each other when sexual mature.

50% of offspring should be GFP positive if derived from the endogenous GFP+ caspase9 host PGCs. Few of the Dazl-aviCaspase9 host offspring were GFP+ and none of the Dazl-iCaspase9 offspring were GFP+(indicated in table FIG. 23 A).

Further, embryonic offspring from Dazl-Caspase host showed black skin phenotype of donor Silkie PGCs (indicated in FIG. 23 B). Moreover hatched offspring from Dazl-Caspase host showing black skin phenotype of donor Silkie PGCs (indicated in FIG. 23 C).

Although the invention has been particularly shown and described with reference to particular examples, it will be understood by those skilled in the art that various changes in the form and details may be made therein without departing from the scope of the present invention.

The invention claimed is:

1. A transgene construct comprising:

(i) a first nucleotide sequence, wherein said first nucleotide sequence encodes an apoptosis inducing enzyme, wherein said apoptosis inducing enzyme is inducible Caspase9 (iCaspase9), wherein the activity of the protein encoded by said first nucleotide sequence causes death of germ cells in the presence of an exogenous induction agent; and (ii) a second nucleotide sequence which targets said construct to avian germ cells, wherein said second nucleotide sequence targets the genetic DAZL locus.

2. The transgene construct according to claim 1, wherein said first nucleotide sequence comprises an apoptosis inducing domain and wherein said exogenous induction agent is a dimerization agent capable of activating said apoptosis domain to cause apoptosis of the germ cells.

3. The transgene construct according to claim 2, wherein said exogenous induction agent is a dimerisation stability drug.

4. The transgene construct according to claim 1, wherein said exogenous induction agent is selected from the group consisting of AP20187 ligand, FK1012, AP1501, or AP1903.

5. The transgenic construct according to claim 1, wherein said second nucleotide sequence targets said construct to germ cells by homologous recombination into a genetic locus expressed only in avian germ cells.

6. The transgenic construct according to claim 1, wherein said second nucleotide sequence targets germ cells via CRISPR/Cas system, wherein said construct comprises a guide RNA which targets a germ cell specific sequence.

7. A method of modifying the germplasm of an avian, said method comprising administering a transgene construct into a fertilised egg or cultured germ cells of said avian and incubating said egg containing said transgene construct or injected with germ cells containing said transgene construct, wherein said transgene construct is the transgene construct according to claim 1 and wherein said transgene construct is integrated into germ cells of said embryo.

8. The method according to claim 7, wherein said method is a method of producing a surrogate host avian, said method comprising the step of administering said exogenous induction agent thereby causing death of said germ cells.

9. The method according to claim 7, wherein said method further comprises the step of transplanting germ cells from a donor avian into said fertilised egg and incubating to hatching to generate offspring avians having the genetic identity of the transplanted germ cells.

10. The method according to claim 9, further comprising crossing male and female offspring from said offspring avians to produce one or more further generations of offspring avians with germ cells having the genetic identity of the transplanted germ cells.

11. A transgenic avian comprising the transgene construct according to claim 1.

* * * * *

UNITED STATES PATENT AND TRADEMARK OFFICE

CERTIFICATE OF CORRECTION

PATENT NO. : 12,279,600 B2
APPLICATION NO. : 17/282846
DATED : April 22, 2025
INVENTOR(S) : McGrew et al.

It is certified that error appears in the above-identified patent and that said Letters Patent is hereby corrected as shown below:

In the Specification

Column 14, Line 32: Please correct “BIB” to read --B/B--

Signed and Sealed this
Second Day of September, 2025

Coke Morgan Stewart
*Acting Director of the United States Patent and Trademark Office*

SEQUENCE LISTING

<160> NUMBER OF SEQ ID NOS: 18

<210> SEQ ID NO 1
<211> LENGTH: 1317
<212> TYPE: DNA
<213> ORGANISM: Artificial Sequence
<220> FEATURE:
<223> OTHER INFORMATION: 2a-iCaspase9-Bam H1 site mutated

<400> SEQUENCE: 1
ggatccggag ctactaactt cagcctgctg aagcaggctg gagacgtgga ggagaaccct 60
ggacctatgc tcgagggagt gcaggtggag actatctccc caggagacgg gcgcaccttc 120
cccaagcgcg gccagacctg cgtggtgcac tacaccggga tgcttgaaga tggaaagaaa 180
gttgattcct cccgggacag aaacaagccc tttaagttta tgctaggcaa gcaggaggtg 240
atccgaggct gggaagaagg ggttgcccag atgagtgtgg gtcagagagc caaactgact 300
atatctccag attatgccta tggtgccact gggcacccag gcatcatccc accacatgcc 360
actctcgtct tcgatgtgga gcttctaaaa ctggaatctg gcggtggttc cggagtcgac 420
ggatttggtg atgtcggtgc tcttgagagt ttgaggggaa atgcagattt ggcttacatc 480
ctgagcatgg agccctgtgg ccactgcctc attatcaaca atgtgaactt ctgccgtgag 540
tccgggctcc gcacccgcac tggctccaac atcgactgtg agaagttgcg gcgtcgcttc 600
tcctcgctgc atttcatggt ggaggtgaag ggcgacctga ctgccaagaa aatggtgctg 660
gctttgctgg agctggcgcg gcaggaccac ggtgctctgg actgctgcgt ggtggtcatt 720
ctctctcacg gctgtcaggc cagccacctg cagttcccag gggctgtcta cggcacagat 780
ggatgccctg tgtcggtcga gaagattgtg aacatcttca atgggaccag ctgccccagc 840
ctgggaggga agcccaagct ctttttcatc caggcctgtg gtggggagca gaaagaccat 900
gggtttgagg tggcctccac ttcccctgaa gacgagtccc ctggcagtaa ccccgagcca 960
gatgccaccc cgttccagga aggtttgagg accttcgacc agctggacgc catatctagt 1020
ttgcccacac ccagtgacat ctttgtgtcc tactctactt tcccaggttt tgtttcctgg 1080
agggacccca agagtggctc ctggtacgtt gagaccctgg acgacatctt tgagcagtgg 1140
gctcactctg aagacctgca gtccctcctg cttagggtcg ctaatgctgt ttcggtgaaa 1200
gggatttata aacagatgcc tggttgcttt aatttcctcc ggaaaaaact tttctttaaa 1260
acatcagtcg actatccgta cgacgtacca gactacgcac tcgacctcga cggatcc 1317

<210> SEQ ID NO 2
<211> LENGTH: 1315
<212> TYPE: DNA
<213> ORGANISM: Artificial Sequence
<220> FEATURE:
<223> OTHER INFORMATION: 2a-aviCaspase9

<400> SEQUENCE: 2

```
agggatccgg agctactaac ttcagcctgc tgaagcaggc tggagacgtg gaggagaacc     60

ctggacctat gctcgaggga gtgcaggtgg agactatctc cccaggagac gggcgcacct    120

tccccaagcg cggccagacc tgcgtggtgc actacaccgg gatgcttgaa gatggaaaga    180

aagttgattc ctcccgggac agaaacaagc cctttaagtt tatgcttggc aagcaggagg    240

tgatccgagg ctgggaagaa ggggttgccc agatgagtgt gggtcagaga gccaaactga    300

ctatatctcc agattatgcc tatggtgcca ctgggcaccc aggcatcatc ccaccacatg    360

ccactctcgt cttcgatgtg gagcttctaa aactggaatc tggcggtggt tccggagtcg    420

acggtgtctc tgtgaattgc agaccagcta ggatgcatgc tagtgcatgc caggtgtacc    480

agctgcgagc agacccttgt gggcactgcc tgatcttcaa caatgtcagc ttcagcagag    540

actctgatct gtcgactcga gctggctctg acatagactg tgagaagctg gagaagcgtt    600

tcaggtccct gtgcttccac gtccggaccc tgcggaacct caaagctcag gaaattgatg    660

tggagctgcg gaagctggcg cggctcgacc acagtgccct ggactgctgc ctcgtggtca    720

tcctctccca tggttgccag acaagccata ttcagtttcc cggagggatt tatggaacag    780

atggcaaaat cattccaatc gaaaggattg tgaactattt caatgggtcc cagtgcccga    840

gtttgagagg aaaacccaaa ctcttcttca tccaggcctg tggaggagaa caaaaggacc    900

aaggatttga ggtggattgt gaatcacccc aagatgaaac ttgccgacgt tccatagagt    960

cggatgcgat tcctttccag gctccatcag ggaatgagga cgagccagac gccgtcgcca   1020

gtttgcccac tcctggtgac atcttggtgt cctattcaac ttttccaggt tttgtgtcct   1080

ggagggacaa ggtgagtggc tcgtggtacg tggaaacctt ggacagcgta ctggaacatt   1140

acgcccgttc tgaagacctg cttaccatgc tacttcgggt gtcagacatc gtatccacca   1200

aggggaggta caagcagatc ccgggctgtt tcaacttcct tcgtaaaaaa ttcttcttcc   1260

tgtgcaaggt cgactatccg tacgacgtac cagactacgc actcgacgga tccaa        1315
```

<210> SEQ ID NO 3
<211> LENGTH: 5985
<212> TYPE: DNA
<213> ORGANISM: Artificial Sequence
<220> FEATURE:
<223> OTHER INFORMATION: Leftarm-GFP-2a-Nitroreductase-T2a-Right arm

<400> SEQUENCE: 3

```
tttttttctt tgagatgagt atcttattgc agctctgtgc ataccccttg aaaatccgta     60

ggtgatgtat ttatgttgac tgaaaatgga gtcattcaaa aattgatgac ttcttccttt    120

tctcttttta atctcgaaac ctgttctcag attcctttat cagaacaaaa agcacggctg    180

catgtttttc accgttcaca cgactgtgtt tagccagcgt atctaaatgc ataacatgat    240

ttgccataac ttgagcctgc cataatcaga gcctcatttt gaaagctgtc atggtctgaa    300

acatagcatg ggtaagatga ttttcacctt gatgatgcat gtttaactca tttcaacgag    360

aggtcaaatc catccaaaaa tgctaaatct atcaaccagt tttcatgttc aagttctggc    420

acaaattttc gttctgactc catacgtgat tagatttcat tttgcaaatc atgaaaacta    480
```

-continued

```
ttgccaaaac atacaatttt aagtcagcag ttttactgcc caaatttgca caagcacatg    540
taacgtgaca gacaaaaacc cactggacag agacaaaata ctgggtttgg ccagtatggt    600
ttggctaagc cacgtttttc agggcaagaa ttgcctcacc tttttttata ttggaatcaa    660
attctcaagt gtaacagcct ggcgccatct cagctgccat taagtagcat gtgctgcaac    720
aagatgtcta ccacacactc tgctctgggt ggtgggggca caccagtgtg gacggcaacc    780
atgacacaag catagagtct tggcagaggt ccattgggtg catttatagt ggttcacact    840
ggggggttat cacagaatca tggaggttgg aaggtacctc cgggggtcat caaatccaac    900
cacttgacaa agcaggttcc ctaaagtaga ttgctcaaga acagtcacag cactgctgct    960
cacagaaaat ctctagttgg taaggttacc tttttttttg ttgtcgctcc cagttaaacc   1020
aaggtgggaa cacatccttt tcatagttgt attgtaggga tgtttatagc tattgctagg   1080
gaaaactgaa cagcgtgcaa ggaagtcagc actgacacag ctttcccacg tgagagagct   1140
atttcaaagc aagatcagca catatcccaa tctgtacttc ctcaaacaca gcccaaaacc   1200
gatagcaagg ccaagcagca gcactgctcc ttcaaggaaa ctgctgcata atctgaattt   1260
cagacggcag gaggaaacaa ggcagcagac tgatgaccta ccaccctgag tctcagctac   1320
atgcgatccg agccactcca actctgcttc ctgcagccct tccttcacgc tcatcttttg   1380
caccttaggc actcttataa ttcaagtact ttgtggcttt gggatatttg aagagcttgg   1440
tcagttagtc acaagtctgg ccacgtgcta tcatattagt ttgaaaagca atggagacac   1500
catctgctga tgctcaaagt ggttacaacc aaaacacaaa aaagcagagc tgtgggaaga   1560
attcaacatt ttgattatgc aagaagctag tcccagcctt gaaatccacc atctgcatca   1620
tgaaagacct aagtagttaa agccacagca gacatacagc ttctatttcc ttaccttctt   1680
catcattaac tacaggtctt ggaagatttt tgctgggaaa aagcttttat tgcaagaact   1740
gtaatttatt aacagggaaa catgaaataa atgtgtaaat tctcctgcac tcccactgtc   1800
attaaaaacg gctttaagaa agagtattca gtaactgcct gcattgtgtt gtgactttct   1860
actctgtgac acacagcctt ctgggcaaag cacatattct gccatgcatg tgggtcgtgc   1920
cttggaaaat gggaacccac attcactgag ggcctcttga tgagctttcc ccttgagaac   1980
agcgaggtct catggatatc ttctcttctc caagccaaat aagcccagat ccctcagctt   2040
tccttcatgg agaggctcca gccctctgat catgcctgca gcccttctct ggacctgctc   2100
cagcagcccc acacgctcct catgctggga ccccagatct gcacatggta ttgcacatgg   2160
ggcctcacaa cggcagagct gagagggaca attccctccc tcagccttta attctgcacg   2220
tacttaattt tgtctgtatt ttttttgcaa tagaatagcc tgcatgctag ttgctgtgtc   2280
gcacagctga attcactagg ttcctgtgaa acaaagggca atcccacagc cactgtagca   2340
cgtgaggagc cacacaggtg ctctaattcc tacaggacag gcctagggac agagcggccc   2400
taggactgcc ctcccgcacc tcctagcttc accttttgcc cgcgatcttt aagtaccctg   2460
aagcataaac agggaaagcg ccgcccgcag cctcaccctg cttcccgccc aacgcggcac   2520
cgcccaggcc gcagccgccc actaagagca ctagcgccac cttctcaccc cacccccacc   2580
acgcgttcct agcggccctg agagctgctg cgcatgcgcc gcctgacgat tcgccctccc   2640
attggctggc ggtcgaagca cggcgggggc acgcggtggc ggctatataa ggcgtctcgg   2700
aagacggcgc catgctattt ggagcggaga gtgaaagtta cagttcctgg tgctggtagg   2760
gagtgtggcg cggagcggag cgctgcggct catcggaacc acaatggagc catagcagag   2820
ccgggcgtgg gggcaagggc agtgcgtgct ggggagggct ccgtcgcgtg gccacgtcgc   2880
```

```
gagagccgtc gggatggtgg cgtcagggcg gggggtgctg ctaacgtgct cctggtcctg   2940
caggtgggct gctggcattc gccatggtga gcaagggcga ggagctgttc accggggtgg   3000
tgcccatcct ggtcgagctg gacggcgacg taaacggcca caagttcagc gtgtccggcg   3060
agggcgaggg cgatgccacc tacggcaagc tgaccctgaa gttcatctgc accaccggca   3120
agctgcccgt gccctggccc accctcgtga ccaccctgac ctacggcgtg cagtgcttca   3180
gccgctaccc cgaccacatg aagcagcacg acttcttcaa gtccgccatg cccgaaggct   3240
acgtccagga gcgcaccatc ttcttcaagg acgacggcaa ctacaagacc cgcgccgagg   3300
tgaagttcga gggcgacacc ctggtgaacc gcatcgagct gaagggcatc gacttcaagg   3360
aggacggcaa catcctgggg cacaagctgg agtacaacta caacagccac aacgtctata   3420
tcatggccga caagcagaag aacggcatca aggtgaactt caagatccgc cacaacatcg   3480
aggacggcag cgtgcagctc gccgaccact accagcagaa cacccccatc ggcgacggcc   3540
ccgtgctgct gcccgacaac cactacctga gcacccagtc cgccctgagc aaagacccca   3600
acgagaagcg cgatcacatg gtcctgctgg agttcgtgac cgccgccggg atcactctcg   3660
gcatggacga gctgtacaag ggatccggag ctactaactt cagcctgctg aagcaggctg   3720
gagacgtgga ggagaaccct ggacctatgg atatcatcag cgtggccctg aagagacaca   3780
gcaccaaggc cttcgatgcc agcaagaagc tgacccccga gcaggccgag cagatcaaga   3840
ccctgctgca gtacagcccc agcagccaga acagccagcc ctggcacttc atcgtggcca   3900
gcaccgagga aggcaaggcc agagtggcca agagcgccgc cggcaactac gtgttcagcg   3960
agagaaagat gctggatgcc agccacgtgg tggtgttctg cgccaagacc gctatggatg   4020
atgtgtggct gaagctggtg gtggatcagg aggatgccga tggcagattc gccacccccg   4080
aggccaaggc cgccaacgat aagggcagaa agttcaccgc cgatatgcac agaaaggatc   4140
tgcacgatga tgccgagtgg atggccaagc aggtgtacct gaacgtgggc aacttcctgc   4200
tcggcgtggc cgccctgggc ctggatgccg tgcccatcga gggcttcgat gccgccatcc   4260
tggatgccga gttcggcctg aaggagaagg gctacaccag cctggtggtg gtgcccgtgg   4320
gccaccacag cgtggaggat ttcaacgcca ccctccccaa gagcagactg ccccagaaca   4380
tcaccctgac cgaggtggga tccggagagg gcagaggaag tctgctaaca tgcggtgacg   4440
tcgaggagaa tcctggacct atggaggagg attgggatac cgaactcgag caggaggcgg   4500
cagcggcttc ccaggggcgt tctgaggagc aggcgtggat ggtgagctgt gtccagggga   4560
gggcggtgcg gcagggagcg gggcactggg atggcccggt ctgggaaggg gaggccgaga   4620
ggccttcgca gtgcttcctg cagctccccg agcagtgcga agaaggaggt gccgggctct   4680
gctgtgggag ccgaaggcac ggagctgcct ggggagggaa tggctgtgtg cctgaggtgc   4740
cagagaccgg caagggctgt acagagaggc aacggttttg tgtacaaatc atttgtatgg   4800
gaaaccacaa aatcttgaag ctttattaca tggcagcgaa atactttggt gtgaagtaaa   4860
ggataagata gaggagtgta atgagagaca gctaaataat attttactac ttgtgggatg   4920
agtgaatatc aggaggaact gctgtaaatt tcaggaggac ctgttgtgaa tcttcagtag   4980
ttggcgccgc tcttacacat cttacagatg ccccttgagc aaagggggat aaggagagat   5040
gaacgggtta tccaaacagg tgatgagcta aaagtacagt tgcctaaaga agtagtagca   5100
tgtgctatca gaatgataat tttgttagtt tggggttagt ttcctgtagt ggtagatagc   5160
cacaacaaga aaaccgctta agtttttgta aaacaaaaaa agcacgatcc agaagtaaaa   5220
```

-continued

```
aatatgggta gtttttttg atgttcctct ctcacctggt gctttggcat actaatatgt   5280

gtctaattgt attaaacagg agaaatttaa acctaggctt tgctggaaat aaaatgttac   5340

aatgctacaa tgtgaaaagt aggtgctatt ctgaactgtt ttgggtggag tatctgaatc   5400

tttgaataat ttaagaggga ctgacatatt taaaatactt aaggataatc tgtagccatg   5460

ctgtaaaaga acaacagaaa tgcagttggg aaggtgatgg aaatagtttt attcatgtta   5520

ctggtggtct gaaacctttc taagcttaaa ctgtagaaaa aaattgcttc aaaagattgc   5580

actattactt tgggcgacaa atgtttttaa ttggttttaa gtgtttgtta gcaaagtgaa   5640

gttgatgcca ccataagtct gacaggaggc aagataaact tgtcttcata ctgcttgtgt   5700

ataacttggt tttgatgaca tttgtgtgtg aacattatgc acttcagtgt agcgaagttt   5760

aagaaacttt gaacagaata acttgaaaga gtgtgcacat gggtgcagaa gtcactttat   5820

ttcagttggg agacttagca cctaaatgca ctgttagttc acatacactt tgcttggcct   5880

gaaggtaaca ttgtgatgtc gcttttttc cctgtaggct aactctggca gaccaaacag   5940

cccatccctc cgcttctcca gcagaccaag cagccccttg tctgg                  5985
```

<210> SEQ ID NO 4
<211> LENGTH: 5155
<212> TYPE: DNA
<213> ORGANISM: Artificial Sequence
<220> FEATURE:
<223> OTHER INFORMATION: Left arm-2a-aviCaspase9-T2a-GFP-Right arm

<400> SEQUENCE: 4

```
cttcgtggct tggtgaagag atcttctgac ctcttcatca ccccctagaa ttaaggctgt     60

aatcatcatt tcagccattg cttaatccac tataatttct gcatgatttc agaaggctat    120

cttgcttcct tgaaactaat aatacctagt ttgtagtgtt tagggatgtg taaaatgtgt    180

ttatgtcaag attttagtta gtctgataag aattgtggaa gaattgcagc tactaaaaag    240

gcagactggg tagcacttcc caccttactc agatttagga gtctcaagac atgtagatgg    300

gtgaaattta ttattctttt ctctgcttgc ttttctggaa agctacctct atttggccag    360

cagttggctc tgaattcctt tctttaaagg agacctgact gctctcctgt ctgcctctta    420

cacagctgta ctggtgtgtc actgatagaa acgtttacct tgaaagtgac aagtgggggc    480

gttgataccc attaacaaca ttaaagggaa aatttcagga aacaagaaaa ctgagaggag    540

ttcagaatga aatgtaagcc ctgtgacaga ctcacactga tggtagtagg gtaactgatg    600

gagatgcatc tataacaatt ctaactttta tttcagaagt ctgtggacag gagcatacaa    660

acagtagtat cttgtctgtt taaccctgaa aaccgtctga ggaacacctt tgtatcacaa    720

gaagactact tcagggtatg tagtgaaagc aaaactaaat ctctaaaacc agctgatctt    780

aactttgttc atatacagga tgccatgaag acaaaggttt atctgtactt gcttgagatt    840

ttactttttg tatgtgcatt gagatgaatg actggttagc tctcagttgg ttaatactca    900

atgaaaattg cagaaattga gttcagtgga tttaagtgca ttgatacaag gctgcataag    960

aactgctgag cagtcagcta ttggatattt agagctaatc atccctcagg agcaatctgc   1020

tgaaaggtaa gcagattgca tcttgtaaac gagagagcag agttaaacgt ttgtggtctt   1080

tgctccactt aagtacccac agtggatgtc tatctgtact tttggttaaa aaatagataa   1140

tttctacaac agactgtagt taggtcagta cctggtcatc aggtattaat ggaaagcttt   1200

ttgctgtgca ttcaatcttc atagaggtct gctttccaat tacattctct ttgttttaag   1260

tataactttg aaactcaaat ataaaagcct gctacttttt tttgttctaa aaagacagat   1320
```

```
gtggactagg cacctgtact gtgaaaccag aatagagaag ctgttgggca gatttgaaga   1380
ggattgagta atatagagaa tgtcttgaga tatttgtgaa gcttttattg ctttgttgca   1440
attgttgtct agaaacatgg gctttttctg ttttttctcc tattccagga gaggagggcg   1500
catcacttca gaaaaggaag agcagtgctc aaaagtgttg gatccggagc tactaacttc   1560
agcctgctga agcaggctgg agacgtggag gagaaccctg gacctatgct cgagggagtg   1620
caggtggaga ctatctcccc aggagacggg cgcaccttcc ccaagcgcgg ccagacctgc   1680
gtggtgcact acaccgggat gcttgaagat ggaaagaaag ttgattcctc ccgggacaga   1740
aacaagccct ttaagtttat gcttggcaag caggaggtga tccgaggctg ggaagaaggg   1800
gttgcccaga tgagtgtggg tcagagagcc aaactgacta tatctccaga ttatgcctat   1860
ggtgccactg ggcacccagg catcatccca ccacatgcca ctctcgtctt cgatgtggag   1920
cttctaaaac tggaatctgg cggtggttcc ggagtcgacg gtgtctctgt gaattgcaga   1980
ccagctagga tgcatgctag tgcatgccag gtgtaccagc tgcgagcaga cccttgtggg   2040
cactgcctga tcttcaacaa tgtcagcttc agcagagact ctgatctgtc gactcgagct   2100
ggctctgaca tagactgtga gaagctggag aagcgtttca ggtccctgtg cttccacgtc   2160
cggaccctgc ggaacctcaa agctcaggaa attgatgtgg agctgcggaa gctggcgcgg   2220
ctcgaccaca gtgccctgga ctgctgcctc gtggtcatcc tctcccatgg ttgccagaca   2280
agccatattc agtttcccgg agggatttat ggaacagatg gcaaaatcat tccaatcgaa   2340
aggattgtga actatttcaa tgggtcccag tgcccgagtt tgagaggaaa acccaaactc   2400
ttcttcatcc aggcctgtgg aggagaacaa aaggaccaag gatttgaggt ggattgtgaa   2460
tcaccccaag atgaaacttg ccgacgttcc atagagtcgg atgcgattcc tttccaggct   2520
ccatcaggga atgaggacga gccagacgcc gtcgccagtt tgcccactcc tggtgacatc   2580
ttggtgtcct attcaacttt tccaggtttt gtgtcctgga gggacaaggt gagtggctcg   2640
tggtacgtgg aaaccttgga cagcgtactg gaacattacg cccgttctga agacctgctt   2700
accatgctac ttcgggtgtc agacatcgta tccaccaagg ggaggtacaa gcagatcccg   2760
ggctgtttca acttccttcg taaaaaattc ttcttcctgt gcaaggtcga ctatccgtac   2820
gacgtaccag actacgcact cgacggatcc ggagagggca gaggaagtct gctaacatgc   2880
ggtgacgtcg aggagaatcc tggacctatg gtgagcaagg gcgaggagct gttcaccggg   2940
gtggtgccca tcctggtcga gctggacggc gacgtaaacg gccacaagtt cagcgtgtcc   3000
ggcgagggcg agggcgatgc cacctacggc aagctgaccc tgaagttcat ctgcaccacc   3060
ggcaagctgc ccgtgccctg gcccaccctc gtgaccaccc tgacctacgg cgtgcagtgc   3120
ttcagccgct accccgacca catgaagcag cacgacttct tcaagtccgc catgcccgaa   3180
ggctacgtcc aggagcgcac catcttcttc aaggacgacg gcaactacaa gacccgcgcc   3240
gaggtgaagt tcgagggcga caccctggtg aaccgcatcg agctgaaggg catcgacttc   3300
aaggaggacg gcaacatcct ggggcacaag ctggagtaca actacaacag ccacaacgtc   3360
tatatcatgg ccgacaagca gaagaacggc atcaaggtga acttcaagat ccgccacaac   3420
atcgaggacg gcagcgtgca gctcgccgac cactaccagc agaacacccc catcggcgac   3480
ggccccgtgc tgctgcccga caaccactac ctgagcaccc agtccgccct gagcaaagac   3540
cccaacgaga agcgcgatca catggtcctg ctggagttcg tgaccgccgc cgggatcact   3600
ctcggcatgg acgagctgta caagtgatga acaaagactt tgaagtacat aaatgtatta   3660
```

```
ctttgatgtt aatacagttc agtttagtaa gatgtgtagt aaaaagtgta accttgttca   3720

aaaagttgct tcaagttgat gtttgtgttc tgttttacct gttccagaat agctattttt   3780

gcttgagaag tttgaagttg taagagttga aatatttcca ggttttatta ctagcttgca   3840

tgcttttcct gctaactaac tgaaatgcta atcttaagga atttatatgg ggaaggggaa   3900

aaaagaaaaa cactttgttt ggtacgtgtg gatttttcttc tgagctttaa ggtacagttt   3960

gttgcatgtt aaaatttagt tcttattaaa ccacaacttt aagttactaa cgtcaaccag   4020

ttacctcttg cagttcaaaa gttgaagcag ttccttgtcc aagatggagt attttaaaac   4080

tgagctctta atcagtggaa cagaagacgt cacggtgtaa ctcaactgaa gccctttaag   4140

tcccggttct ctttagacta cctaatcaat gtctttgttt gctaacgaca gtttatctat   4200

gtgaatccta aaattcctat atgtaactta agatgcaaga atgtaattag ttacattggc   4260

tgctcagtgg agtatgactt tttttttac tggattaatt ttagcaatac ctgtatctta   4320

aaattgtgag aaaatactgc atttaaaata tgcctaactt tgtgatgcaa tatgttaatc   4380

aaagaataca tgtaagcata ttttaataat aattatgtag attttagtca tgtattttga   4440

aacaattaaa atttttaatt ttgacttacc ttcccagtgt gagtgacatc ctaatataat   4500

acttctaaat cttaagctgc tttgagaaag gcatgcagcg tatttattga aggaattgaa   4560

gatttcttac cctacataag aattccagtt aggacaagtt tatagcaaca aactttcaca   4620

tttgctgtta gttctacctg cgattttgaa ggagtacaac tgagaacagc actcagtctt   4680

gtatgtgtgt tgggtcctag tctgattcat ttttcttatt actaccctta tacctcagtc   4740

tccaagtaaa aaaggaaata actcctcctt tgtagacgtg tatatgtgaa tgaatagaat   4800

ggcatgtccc acttcaaatg tctagaagta gatgttggtg aaacatgcaa taagagctga   4860

gttgctctgt acctggatag tgggctgtaa gatgcagcac aggagtgtcc caggactgtt   4920

gttcaggagt aggagtcagg ggagggaggc agggcttggg ggatagcaat aatagttggt   4980

gccgttctcc ataaaattac tcagaagcaa tgttctggca gcataaatcg acctaaagtt   5040

gttaactttt tctctgctca gaccgttccc tagcactaaa gatgctgtgt ccttaagtgt   5100

gtttccatac tatccatcac catgtttttc ccaacctatt gctttaatag tattg        5155
```

<210> SEQ ID NO 5
<211> LENGTH: 5161
<212> TYPE: DNA
<213> ORGANISM: Artificial Sequence
<220> FEATURE:
<223> OTHER INFORMATION: Left arm-2a-iCaspase9-T2a-GFP-Right arm

<400> SEQUENCE: 5

```
cttcgtggct tggtgaagag atcttctgac ctcttcatca ccccctagaa ttaaggctgt     60

aatcatcatt tcagccattg cttaatccac tataatttct gcatgatttc agaaggctat    120

cttgcttcct tgaaactaat aatacctagt ttgtagtgtt tagggatgtg taaaatgtgt    180

ttatgtcaag attttagtta gtctgataag aattgtggaa gaattgcagc tactaaaaag    240

gcagactggg tagcacttcc caccttactc agatttagga gtctcaagac atgtagatgg    300

gtgaaattta ttattctttt ctctgcttgc ttttctggaa agctacctct atttggccag    360

cagttggctc tgaattcctt tctttaaagg agacctgact gctctcctgt ctgcctctta    420

cacagctgta ctggtgtgtc actgatagaa acgtttacct tgaaagtgac aagtgggggc    480

gttgataccc attaacaaca ttaaagggaa aatttcagga aacaagaaaa ctgagaggag    540

ttcagaatga aatgtaagcc ctgtgacaga ctcacactga tggtagtagg gtaactgatg    600
```

-continued

```
gagatgcatc tataacaatt ctaactttta tttcagaagt ctgtggacag gagcatacaa    660
acagtagtat cttgtctgtt taaccctgaa aaccgtctga ggaacacctt tgtatcacaa    720
gaagactact tcagggtatg tagtgaaagc aaaactaaat ctctaaaacc agctgatctt    780
aactttgttc atatacagga tgccatgaag acaaaggttt atctgtactt gcttgagatt    840
ttactttttg tatgtgcatt gagatgaatg actggttagc tctcagttgg ttaatactca    900
atgaaaattg cagaaattga gttcagtgga tttaagtgca ttgatacaag gctgcataag    960
aactgctgag cagtcagcta ttggatattt agagctaatc atccctcagg agcaatctgc   1020
tgaaaggtaa gcagattgca tcttgtaaac gagagagcag agttaaacgt ttgtggtctt   1080
tgctccactt aagtacccac agtggatgtc tatctgtact tttggttaaa aaatagataa   1140
tttctacaac agactgtagt taggtcagta cctggtcatc aggtattaat ggaaagcttt   1200
ttgctgtgca ttcaatcttc atagaggtct gctttccaat tacattctct ttgttttaag   1260
tataactttg aaactcaaat ataaaagcct gctacttttt tttgttctaa aaagacagat   1320
gtggactagg cacctgtact gtgaaaccag aatagagaag ctgttgggca gatttgaaga   1380
ggattgagta atatagagaa tgtcttgaga tatttgtgaa gcttttattg ctttgttgca   1440
attgttgtct agaaacatgg gctttttctg ttttttctcc tattccagga gaggagggcg   1500
catcacttca gaaaaggaag agcagtgctc aaaagtgttg gatccggagc tactaacttc   1560
agcctgctga agcaggctgg agacgtggag gagaaccctg gacctatgct cgagggagtg   1620
caggtggaga ctatctcccc aggagacggg cgcaccttcc ccaagcgcgg ccagacctgc   1680
gtggtgcact acaccgggat gcttgaagat ggaaagaaag ttgattcctc ccgggacaga   1740
aacaagccct ttaagtttat gctaggcaag caggaggtga tccgaggctg ggaagaaggg   1800
gttgcccaga tgagtgtggg tcagagagcc aaactgacta tatctccaga ttatgcctat   1860
ggtgccactg ggcacccagg catcatccca ccacatgcca ctctcgtctt cgatgtggag   1920
cttctaaaac tggaatctgg cggtggttcc ggagtcgacg gatttggtga tgtcggtgct   1980
cttgagagtt tgaggggaaa tgcagatttg gcttacatcc tgagcatgga gccctgtggc   2040
cactgcctca ttatcaacaa tgtgaacttc tgccgtgagt ccgggctccg cacccgcact   2100
ggctccaaca tcgactgtga gaagttgcgg cgtcgcttct cctcgctgca tttcatggtg   2160
gaggtgaagg gcgacctgac tgccaagaaa atggtgctgg ctttgctgga gctggcgcgg   2220
caggaccacg gtgctctgga ctgctgcgtg gtggtcattc tctctcacgg ctgtcaggcc   2280
agccacctgc agttcccagg ggctgtctac ggcacagatg gatgccctgt gtcggtcgag   2340
aagattgtga acatcttcaa tgggaccagc tgccccagcc tgggagggaa gcccaagctc   2400
tttttcatcc aggcctgtgg tggggagcag aaagaccatg ggtttgaggt ggcctccact   2460
tcccctgaag acgagtcccc tggcagtaac cccgagccag atgccacccc gttccaggaa   2520
ggtttgagga ccttcgacca gctggacgcc atatctagtt tgcccacacc cagtgacatc   2580
tttgtgtcct actctacttt cccaggtttt gtttcctgga gggaccccaa gagtggctcc   2640
tggtacgttg agaccctgga cgacatcttt gagcagtggg ctcactctga agacctgcag   2700
tccctcctgc ttagggtcgc taatgctgtt tcggtgaaag ggatttataa acagatgcct   2760
ggttgcttta atttcctccg gaaaaaactt ttctttaaaa catcagtcga ctatccgtac   2820
gacgtaccag actacgcact cgacctcgac ggatccggag agggcagagg aagtctgcta   2880
acatgcggtg acgtcgagga gaatcctgga cctatggtga gcaagggcga ggagctgttc   2940
```

-continued

```
accggggtgg tgcccatcct ggtcgagctg gacggcgacg taaacggcca caagttcagc   3000
gtgtccggcg agggcgaggg cgatgccacc tacggcaagc tgaccctgaa gttcatctgc   3060
accaccggca agctgcccgt gccctggccc accctcgtga ccaccctgac ctacggcgtg   3120
cagtgcttca gccgctaccc cgaccacatg aagcagcacg acttcttcaa gtccgccatg   3180
cccgaaggct acgtccagga gcgcaccatc ttcttcaagg acgacggcaa ctacaagacc   3240
cgcgccgagg tgaagttcga gggcgacacc ctggtgaacc gcatcgagct gaagggcatc   3300
gacttcaagg aggacggcaa catcctgggg cacaagctgg agtacaacta caacagccac   3360
aacgtctata tcatggccga caagcagaag aacggcatca aggtgaactt caagatccgc   3420
cacaacatcg aggacggcag cgtgcagctc gccgaccact accagcagaa cacccccatc   3480
ggcgacggcc ccgtgctgct gcccgacaac cactacctga gcacccagtc cgccctgagc   3540
aaagacccca acgagaagcg cgatcacatg gtcctgctgg agttcgtgac cgccgccggg   3600
atcactctcg gcatggacga gctgtacaag tgatgaacaa agactttgaa gtacataaat   3660
gtattacttt gatgttaata cagttcagtt tagtaagatg tgtagtaaaa agtgtaacct   3720
tgttcaaaaa gttgcttcaa gttgatgttt gtgttctgtt ttacctgttc cagaatagct   3780
atttttgctt gagaagtttg aagttgtaag agttgaaata tttccaggtt ttattactag   3840
cttgcatgct tttcctgcta actaactgaa atgctaatct taaggaattt atatggggaa   3900
ggggaaaaaa gaaaaacact ttgtttggta cgtgtggatt ttcttctgag ctttaaggta   3960
cagtttgttg catgttaaaa tttagttctt attaaaccac aactttaagt tactaacgtc   4020
aaccagttac ctcttgcagt tcaaaagttg aagcagttcc ttgtccaaga tggagtattt   4080
taaaactgag ctcttaatca gtggaacaga agacgtcacg gtgtaactca actgaagccc   4140
tttaagtccc ggttctcttt agactaccta atcaatgtct ttgtttgcta acgacagttt   4200
atctatgtga atcctaaaat tcctatatgt aacttaagat gcaagaatgt aattagttac   4260
attggctgct cagtggagta tgactttttt ttttactgga ttaattttag caatacctgt   4320
atcttaaaat tgtgagaaaa tactgcattt aaaatatgcc taactttgtg atgcaatatg   4380
ttaatcaaag aatacatgta agcatatttt aataataatt atgtagattt tagtcatgta   4440
ttttgaaaca attaaaattt ttaattttga cttaccttcc cagtgtgagt gacatcctaa   4500
tataatactt ctaaatctta agctgctttg agaaaggcat gcagcgtatt tattgaagga   4560
attgaagatt tcttacccta cataagaatt ccagttagga caagtttata gcaacaaact   4620
ttcacatttg ctgttagttc tacctgcgat tttgaaggag tacaactgag aacagcactc   4680
agtcttgtat gtgtgttggg tcctagtctg attcattttt cttattacta cccttatacc   4740
tcagtctcca agtaaaaaag gaaataactc ctcctttgta gacgtgtata tgtgaatgaa   4800
tagaatggca tgtcccactt caaatgtcta gaagtagatg ttggtgaaac atgcaataag   4860
agctgagttg ctctgtacct ggatagtggg ctgtaagatg cagcacagga gtgtcccagg   4920
actgttgttc aggagtagga gtcaggggag ggaggcaggg cttgggggat agcaataata   4980
gttggtgccg ttctccataa aattactcag aagcaatgtt ctggcagcat aaatcgacct   5040
aaagttgtta actttttctc tgctcagacc gttccctagc actaaagatg ctgtgtcctt   5100
aagtgtgttt ccatactatc catcaccatg tttttcccaa cctattgctt taatagtatt   5160
g                                                                   5161
```

<210> SEQ ID NO 6
<211> LENGTH: 6579

-continued

<212> TYPE: DNA
<213> ORGANISM: Artificial Sequence
<220> FEATURE:
<223> OTHER INFORMATION: Left arm-GFP-2a-iCaspase9-T2a-Right arm

<400> SEQUENCE: 6

```
tttttttctt tgagatgagt atcttattgc agctctgtgc ataccccttg aaaatccgta     60

ggtgatgtat ttatgttgac tgaaaatgga gtcattcaaa aattgatgac ttcttccttt    120

tctcttttta atctcgaaac ctgttctcag attcctttat cagaacaaaa agcacggctg    180

catgtttttc accgttcaca cgactgtgtt tagccagcgt atctaaatgc ataacatgat    240

ttgccataac ttgagcctgc cataatcaga gcctcatttt gaaagctgtc atggtctgaa    300

acatagcatg ggtaagatga ttttcacctt gatgatgcat gtttaactca tttcaacgag    360

aggtcaaatc catccaaaaa tgctaaatct atcaaccagt tttcatgttc aagttctggc    420

acaaattttc gttctgactc catacgtgat tagatttcat tttgcaaatc atgaaaacta    480

ttgccaaaac atacaatttt aagtcagcag ttttactgcc caaatttgca caagcacatg    540

taacgtgaca gacaaaaacc cactggacag agacaaaata ctgggtttgg ccagtatggt    600

ttggctaagc cacgtttttc agggcaagaa ttgcctcacc tttttttata ttggaatcaa    660

attctcaagt gtaacagcct ggcgccatct cagctgccat taagtagcat gtgctgcaac    720

aagatgtcta ccacacactc tgctctgggt ggtgggggca caccagtgtg gacggcaacc    780

atgacacaag catagagtct tggcagaggt ccattgggtg catttatagt ggttcacact    840

ggggggttat cacagaatca tggaggttgg aaggtacctc cgggggtcat caaatccaac    900

cacttgacaa agcaggttcc ctaaagtaga ttgctcaaga acagtcacag cactgctgct    960

cacagaaaat ctctagttgg taaggttacc tttttttttg ttgtcgctcc cagttaaacc   1020

aaggtgggaa cacatccttt tcatagttgt attgtaggga tgtttatagc tattgctagg   1080

gaaaactgaa cagcgtgcaa ggaagtcagc actgacacag ctttcccacg tgagagagct   1140

atttcaaagc aagatcagca catatcccaa tctgtacttc ctcaaacaca gcccaaaacc   1200

gatagcaagg ccaagcagca gcactgctcc ttcaaggaaa ctgctgcata atctgaattt   1260

cagacggcag gaggaaacaa ggcagcagac tgatgaccta ccaccctgag tctcagctac   1320

atgcgatccg agccactcca actctgcttc ctgcagccct tccttcacgc tcatcttttg   1380

caccttaggc actcttataa ttcaagtact ttgtggcttt gggatatttg aagagcttgg   1440

tcagttagtc acaagtctgg ccacgtgcta tcatattagt ttgaaaagca atggagacac   1500

catctgctga tgctcaaagt ggttacaacc aaaacacaaa aaagcagagc tgtgggaaga   1560

attcaacatt ttgattatgc aagaagctag tcccagcctt gaaatccacc atctgcatca   1620

tgaaagacct aagtagttaa agccacagca gacatacagc ttctatttcc ttaccttctt   1680

catcattaac tacaggtctt ggaagatttt tgctgggaaa aagcttttat tgcaagaact   1740

gtaatttatt aacagggaaa catgaaataa atgtgtaaat tctcctgcac tcccactgtc   1800

attaaaaacg gctttaagaa agagtattca gtaactgcct gcattgtgtt gtgactttct   1860

actctgtgac acacagcctt ctgggcaaag cacatattct gccatgcatg tgggtcgtgc   1920

cttggaaaat gggaacccac attcactgag ggcctcttga tgagctttcc ccttgagaac   1980

agcgaggtct catggatatc ttctcttctc caagccaaat aagcccagat ccctcagctt   2040

tccttcatgg agaggctcca gccctctgat catgcctgca gcccttctct ggacctgctc   2100

cagcagcccc acacgctcct catgctggga ccccagatct gcacatggta ttgcacatgg   2160
```

-continued

```
ggcctcacaa cggcagagct gagagggaca attccctccc tcagccttta attctgcacg   2220
tacttaattt tgtctgtatt ttttttgcaa tagaatagcc tgcatgctag ttgctgtgtc   2280
gcacagctga attcactagg ttcctgtgaa acaaagggca atcccacagc cactgtagca   2340
cgtgaggagc cacacaggtg ctctaattcc tacaggacag gcctagggac agagcggccc   2400
taggactgcc ctcccgcacc tcctagcttc accttttgcc cgcgatcttt aagtaccctg   2460
aagcataaac agggaaagcg ccgcccgcag cctcaccctg cttcccgccc aacgcggcac   2520
cgcccaggcc gcagccgccc actaagagca ctagcgccac cttctcaccc cacccccacc   2580
acgcgttcct agcggccctg agagctgctg cgcatgcgcc gcctgacgat tcgccctccc   2640
attggctggc ggtcgaagca cggcgggggc acgcggtggc ggctatataa ggcgtctcgg   2700
aagacggcgc catgctattt ggagcggaga gtgaaagtta cagttcctgg tgctggtagg   2760
gagtgtggcg cggagcggag cgctgcggct catcggaacc acaatggagc catagcagag   2820
ccgggcgtgg gggcaagggc agtgcgtgct ggggagggct ccgtcgcgtg gccacgtcgc   2880
gagagccgtc gggatggtgg cgtcagggcg gggggtgctg ctaacgtgct cctggtcctg   2940
caggtgggct gctggcattc gccatggtga gcaagggcga ggagctgttc accggggtgg   3000
tgcccatcct ggtcgagctg gacggcgacg taaacggcca caagttcagc gtgtccggcg   3060
agggcgaggg cgatgccacc tacggcaagc tgaccctgaa gttcatctgc accaccggca   3120
agctgcccgt gccctggccc accctcgtga ccaccctgac ctacggcgtg cagtgcttca   3180
gccgctaccc cgaccacatg aagcagcacg acttcttcaa gtccgccatg cccgaaggct   3240
acgtccagga gcgcaccatc ttcttcaagg acgacggcaa ctacaagacc cgcgccgagg   3300
tgaagttcga gggcgacacc ctggtgaacc gcatcgagct gaagggcatc gacttcaagg   3360
aggacggcaa catcctgggg cacaagctgg agtacaacta caacagccac aacgtctata   3420
tcatggccga caagcagaag aacggcatca aggtgaactt caagatccgc cacaacatcg   3480
aggacggcag cgtgcagctc gccgaccact accagcagaa cacccccatc ggcgacggcc   3540
ccgtgctgct gcccgacaac cactacctga gcacccagtc cgccctgagc aaagacccca   3600
acgagaagcg cgatcacatg gtcctgctgg agttcgtgac cgccgccggg atcactctcg   3660
gcatggacga gctgtacaag ggatccggag ctactaactt cagcctgctg aagcaggctg   3720
gagacgtgga ggagaaccct ggacctatgc tcgagggagt gcaggtggag actatctccc   3780
caggagacgg gcgcaccttc cccaagcgcg gccagacctg cgtggtgcac tacaccggga   3840
tgcttgaaga tggaaagaaa gttgattcct cccgggacag aaacaagccc tttaagttta   3900
tgctaggcaa gcaggaggtg atccgaggct gggaagaagg ggttgcccag atgagtgtgg   3960
gtcagagagc caaactgact atatctccag attatgccta tggtgccact gggcacccag   4020
gcatcatccc accacatgcc actctcgtct tcgatgtgga gcttctaaaa ctggaatctg   4080
gcggtggatc cggagtcgac ggatttggtg atgtcggtgc tcttgagagt ttgaggggaa   4140
atgcagattt ggcttacatc ctgagcatgg agccctgtgg ccactgcctc attatcaaca   4200
atgtgaactt ctgccgtgag tccgggctcc gcacccgcac tggctccaac atcgactgtg   4260
agaagttgcg gcgtcgcttc tcctcgctgc atttcatggt ggaggtgaag ggcgacctga   4320
ctgccaagaa aatggtgctg gctttgctgg agctggcgcg gcaggaccac ggtgctctgg   4380
actgctgcgt ggtggtcatt ctctctcacg gctgtcaggc cagccacctg cagttcccag   4440
gggctgtcta cggcacagat ggatgccctg tgtcggtcga gaagattgtg aacatcttca   4500
atgggaccag ctgccccagc ctgggaggga agcccaagct ctttttcatc caggcctgtg   4560
```

-continued

```
gtggggagca gaaagaccat gggtttgagg tggcctccac ttcccctgaa gacgagtccc   4620

ctggcagtaa ccccgagcca gatgccaccc cgttccagga aggtttgagg accttcgacc   4680

agctggacgc catatctagt ttgcccacac ccagtgacat ctttgtgtcc tactctactt   4740

tcccaggttt tgtttcctgg agggacccca agagtggctc ctggtacgtt gagaccctgg   4800

acgacatctt tgagcagtgg gctcactctg aagacctgca gtccctcctg cttagggtcg   4860

ctaatgctgt ttcggtgaaa gggatttata aacagatgcc tggttgcttt aatttcctcc   4920

ggaaaaaact tttctttaaa acatcagtcg actatccgta cgacgtacca gactacgcac   4980

tcgacctcga cggatccgga gagggcagag gaagtctgct aacatgcggt gacgtcgagg   5040

agaatcctgg acctatggag gaggattggg ataccgaact cgagcaggag gcggcagcgg   5100

cttcccaggg gcgttctgag gagcaggcgt ggatggtgag ctgtgtccag gggagggcgg   5160

tgcggcaggg agcggggcac tgggatggcc cggtctggga aggggaggcc gagaggcctt   5220

cgcagtgctt cctgcagctc cccgagcagt gcgaagaagg aggtgccggg ctctgctgtg   5280

ggagccgaag gcacggagct gcctggggag ggaatggctg tgtgcctgag gtgccagaga   5340

ccggcaaggg ctgtacagag aggcaacggt tttgtgtaca aatcatttgt atgggaaacc   5400

acaaaatctt gaagctttat tacatggcag cgaaatactt tggtgtgaag taaaggataa   5460

gatagaggag tgtaatgaga gacagctaaa taatatttta ctacttgtgg gatgagtgaa   5520

tatcaggagg aactgctgta aatttcagga ggacctgttg tgaatcttca gtagttggcg   5580

ccgctcttac acatcttaca gatgcccctt gagcaaaggg ggataaggag agatgaacgg   5640

gttatccaaa caggtgatga gctaaaagta cagttgccta aagaagtagt agcatgtgct   5700

atcagaatga taattttgtt agtttggggt tagtttcctg tagtggtaga tagccacaac   5760

aagaaaaccg cttaagtttt tgtaaaacaa aaaaagcacg atccagaagt aaaaaatatg   5820

ggtagttttt tttgatgttc ctctctcacc tggtgctttg gcatactaat atgtgtctaa   5880

ttgtattaaa caggagaaat ttaaacctag gctttgctgg aaataaaatg ttacaatgct   5940

acaatgtgaa aagtaggtgc tattctgaac tgttttgggt ggagtatctg aatctttgaa   6000

taatttaaga gggactgaca tatttaaaat acttaaggat aatctgtagc catgctgtaa   6060

aagaacaaca gaaatgcagt tgggaaggtg atggaaatag ttttattcat gttactggtg   6120

gtctgaaacc tttctaagct taaactgtag aaaaaaattg cttcaaaaga ttgcactatt   6180

actttgggcg acaaatgttt ttaattggtt ttaagtgttt gttagcaaag tgaagttgat   6240

gccaccataa gtctgacagg aggcaagata aacttgtctt catactgctt gtgtataact   6300

tggttttgat gacatttgtg tgtgaacatt atgcacttca gtgtagcgaa gtttaagaaa   6360

ctttgaacag aataacttga aagagtgtgc acatgggtgc agaagtcact ttatttcagt   6420

tgggagactt agcacctaaa tgcactgtta gttcacatac actttgcttg gcctgaaggt   6480

aacattgtga tgtcgctttt tttccctgta ggctaactct ggcagaccaa acagcccatc   6540

cctccgcttc tccagcagac caagcagccc cttgtctgg                          6579
```

<210> SEQ ID NO 7
<211> LENGTH: 75
<212> TYPE: DNA
<213> ORGANISM: Artificial Sequence
<220> FEATURE:
<223> OTHER INFORMATION: forward primer

<400> SEQUENCE: 7

-continued

```
cggtgacgtc gaggagaatc ctggacctat ggaggaggat tgggataccg aactcgagca     60

ggaggcggca gcggc                                                      75


<210> SEQ ID NO 8
<211> LENGTH: 47
<212> TYPE: DNA
<213> ORGANISM: Artificial Sequence
<220> FEATURE:
<223> OTHER INFORMATION: reverse primer

<400> SEQUENCE: 8

gaaatccagc ttccagttcc cacctggcca gacaaggggc tgcttgg                   47


<210> SEQ ID NO 9
<211> LENGTH: 41
<212> TYPE: DNA
<213> ORGANISM: Artificial Sequence
<220> FEATURE:
<223> OTHER INFORMATION: forward primer

<400> SEQUENCE: 9

ggtgggctgc tggcattcgc catggtgagc aagggcgagg a                         41


<210> SEQ ID NO 10
<211> LENGTH: 76
<212> TYPE: DNA
<213> ORGANISM: Artificial Sequence
<220> FEATURE:
<223> OTHER INFORMATION: reverse primer

<400> SEQUENCE: 10

gattctcctc gacgtcaccg catgttagca gacttcctct gccctctccg gatcccttgt     60

acagctcgtc catgcc                                                     76


<210> SEQ ID NO 11
<211> LENGTH: 57
<212> TYPE: DNA
<213> ORGANISM: Artificial Sequence
<220> FEATURE:
<223> OTHER INFORMATION: forward primer

<400> SEQUENCE: 11

tctcccatat ggtcgacctg caggcggccg cgaattcact agtgattctt cgtggtt        57


<210> SEQ ID NO 12
<211> LENGTH: 48
<212> TYPE: DNA
<213> ORGANISM: Artificial Sequence
<220> FEATURE:
<223> OTHER INFORMATION: reverse primer

<400> SEQUENCE: 12

aggctgaagt tagtagctcc ggatccaaca cttttgagca ctgctctt                  48


<210> SEQ ID NO 13
<211> LENGTH: 107
<212> TYPE: DNA
<213> ORGANISM: Artificial Sequence
<220> FEATURE:
<223> OTHER INFORMATION: forward primer

<400> SEQUENCE: 13

cagaacatca ccctgaccga ggtgggatcc ggagagggca gaggaagtct gctaacatgc     60

ggtgacgtcg aggagaatcc tggacctatg gtgagcaagg gcgagga                  107
```

-continued

```
<210> SEQ ID NO 14
<211> LENGTH: 22
<212> TYPE: DNA
<213> ORGANISM: Artificial Sequence
<220> FEATURE:
<223> OTHER INFORMATION: reverse primer

<400> SEQUENCE: 14

cttgtacagc tcgtccatgc cg                                            22


<210> SEQ ID NO 15
<211> LENGTH: 94
<212> TYPE: DNA
<213> ORGANISM: Artificial Sequence
<220> FEATURE:
<223> OTHER INFORMATION: forward primer

<400> SEQUENCE: 15

tctcggcatg gacgagctgt acaagtgatg aacaaagact ttgaagtaca taaatgtatt    60

actttgatgt taatacagtt cagtttagta agat                                94


<210> SEQ ID NO 16
<211> LENGTH: 55
<212> TYPE: DNA
<213> ORGANISM: Artificial Sequence
<220> FEATURE:
<223> OTHER INFORMATION: reverse primer

<400> SEQUENCE: 16

ctcttcgaaa tccagcttcc agttcccacc tggcaatact attaaagcaa taggt         55


<210> SEQ ID NO 17
<211> LENGTH: 20
<212> TYPE: DNA
<213> ORGANISM: Artificial Sequence
<220> FEATURE:
<223> OTHER INFORMATION: guide sequence

<400> SEQUENCE: 17

ggtcctattc caggagagga                                                20


<210> SEQ ID NO 18
<211> LENGTH: 20
<212> TYPE: DNA
<213> ORGANISM: Artificial Sequence
<220> FEATURE:
<223> OTHER INFORMATION: guide sequence

<400> SEQUENCE: 18

ggcttactaa actgaactgt                                                20
```